United States Patent
Degrace et al.

(10) Patent No.: US 9,901,631 B2
(45) Date of Patent: Feb. 27, 2018

(54) METHOD AND CELLS FOR THE PRODUCTION OF VIRAL VACCINES

(71) Applicants: The Broad Institute, Inc., Cambridge, MA (US); Massachusetts General Hospital, Boston, MA (US)

(72) Inventors: Marciela Degrace, Cambridge, MA (US); Nir Hacohen, Brookline, MA (US); Sagi Shapira, Boston, MA (US); Liguo Wu, Quincy, MA (US)

(73) Assignees: The Broad Institute, Inc., Cambridge, MA (US); The General Hospital Corporation, Boston, MA (US)

( * ) Notice: Subject to any disclaimer, the term of this patent is extended or adjusted under 35 U.S.C. 154(b) by 0 days.

(21) Appl. No.: 14/371,534

(22) PCT Filed: Jan. 10, 2013

(86) PCT No.: PCT/US2013/021002
§ 371 (c)(1),
(2) Date: Jul. 10, 2014

(87) PCT Pub. No.: WO2013/106548
PCT Pub. Date: Jul. 18, 2013

(65) Prior Publication Data
US 2015/0010593 A1 Jan. 8, 2015

Related U.S. Application Data

(60) Provisional application No. 61/585,006, filed on Jan. 10, 2012.

(51) Int. Cl.
| | | |
|---|---|---|
| *C12N 9/22* | (2006.01) | |
| *C12N 15/90* | (2006.01) | |
| *C12N 15/85* | (2006.01) | |
| *C12N 15/00* | (2006.01) | |
| *C12Q 1/68* | (2006.01) | |
| *A61K 39/145* | (2006.01) | |
| *A01K 67/027* | (2006.01) | |
| *C12N 7/00* | (2006.01) | |

(52) U.S. Cl.
CPC ........ *A61K 39/145* (2013.01); *A01K 67/0276* (2013.01); *C12N 7/00* (2013.01); *C12N 2760/16034* (2013.01); *C12N 2760/16051* (2013.01); *C12N 2760/16152* (2013.01)

(58) Field of Classification Search
CPC .... C07K 14/005; C12N 7/00; A01K 67/0276; A61K 38/00; A61K 47/48246
See application file for complete search history.

(56) References Cited

U.S. PATENT DOCUMENTS 8,735,371 B2 * 5/2014 Carthew .......... C07K 14/43581
514/44 A

FOREIGN PATENT DOCUMENTS

| WO | WO 2003/028537 A2 | | 4/2003 |
|---|---|---|---|
| WO | WO2001075655 | * | 7/2007 |
| WO | WO 2011/005765 A1 | | 1/2011 |
| WO | WO2011005765 | * | 1/2011 |
| WO | WO2011034996 | * | 3/2011 |
| WO | WO 2011/072247 A2 | | 6/2011 |
| WO | WO2011072247 | * | 6/2011 |

OTHER PUBLICATIONS

Kakugawa et al., "RuvB-like protein 2 is a suppressor of influenza A virus polymerases", 2009, 83(13):6429-6434.*
Health Sciences Authority (HSA), "www.hsa.gov.sg", HSA Consumer Guide, Nov. 2009:1-5.*
Oyston and Robinson, "The current challenges for vaccine development", Journal of Medical Microbiology, 2012, 61:889-894.*
Hao, L. et al., "Drosophila RNAi screen identifies host genes important for influenza virus replication", *Nature: International Weekly Journal of Science*, 454(7206):890-893 (2008).
Kakugawa, S. et al., "RuvB-Like Protein 2 is a Suppressor of Influenza A Virus Polymerases", *Journal of Virology*, 83(13):6429-6434 (2009).
Menard, L. et al., "In vivo silencing of Reptin blocks the progression of human hepatocellular carcinoma in xenografts and is associated with replicative senescence", *Journal of Hepatology*, 52(5):681-689 (2010).
Vester, D. et al., "Virus—host cell interactions in vaccine production cell lines infected with different human influenza A virus variants: A proteomic approach," *Journal of Proteomics*, 73(9):1656-1669 (2010).

* cited by examiner

*Primary Examiner* — Barry A Chestnut
(74) *Attorney, Agent, or Firm* — Melissa Hunter-Ensor; Leslie Serunian; Greenberg Traurig, LLP

(57) ABSTRACT

The present invention provides genetically modified cells useful for viral replication and the production of viral vaccines.

15 Claims, 34 Drawing Sheets

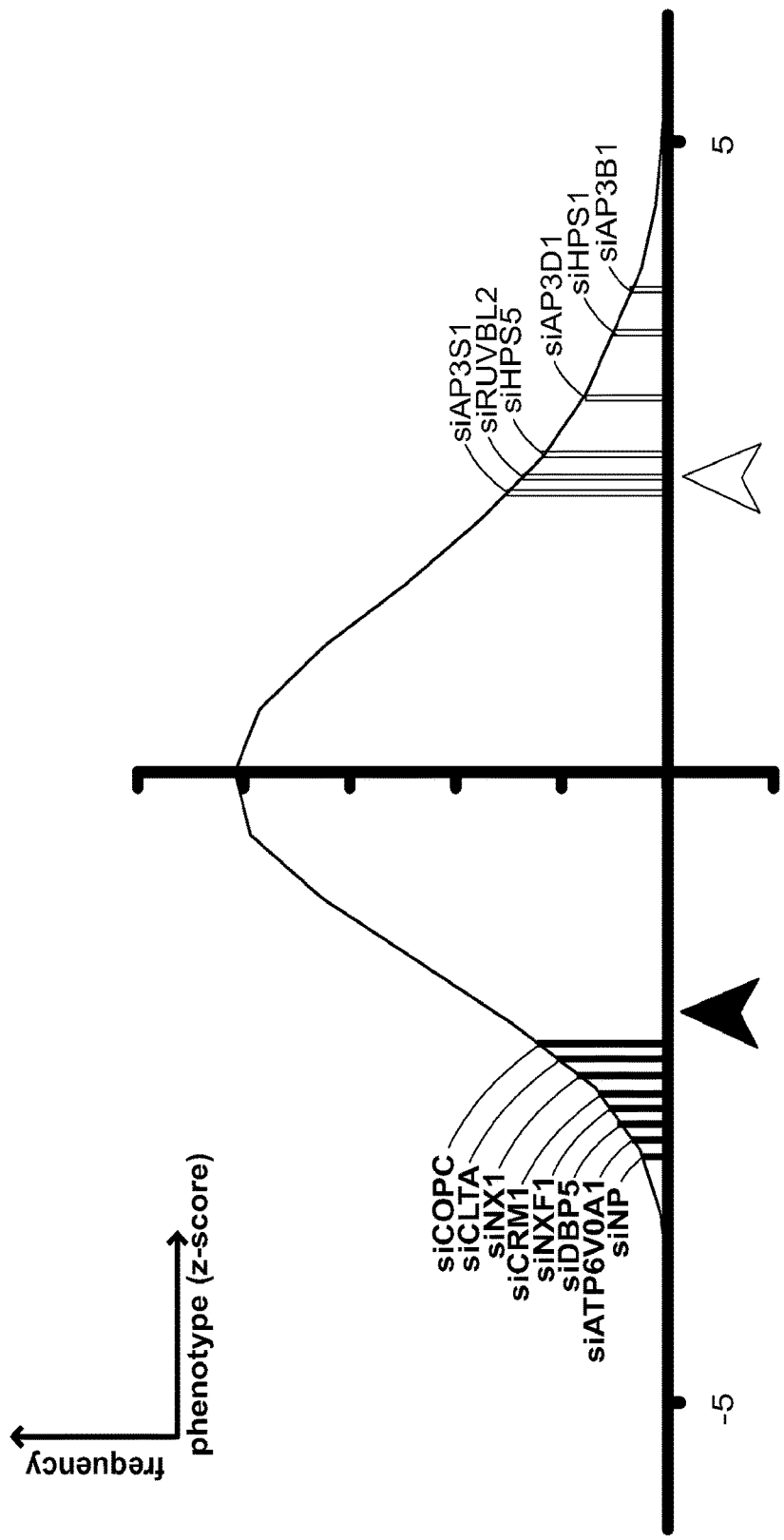

PR8 infection

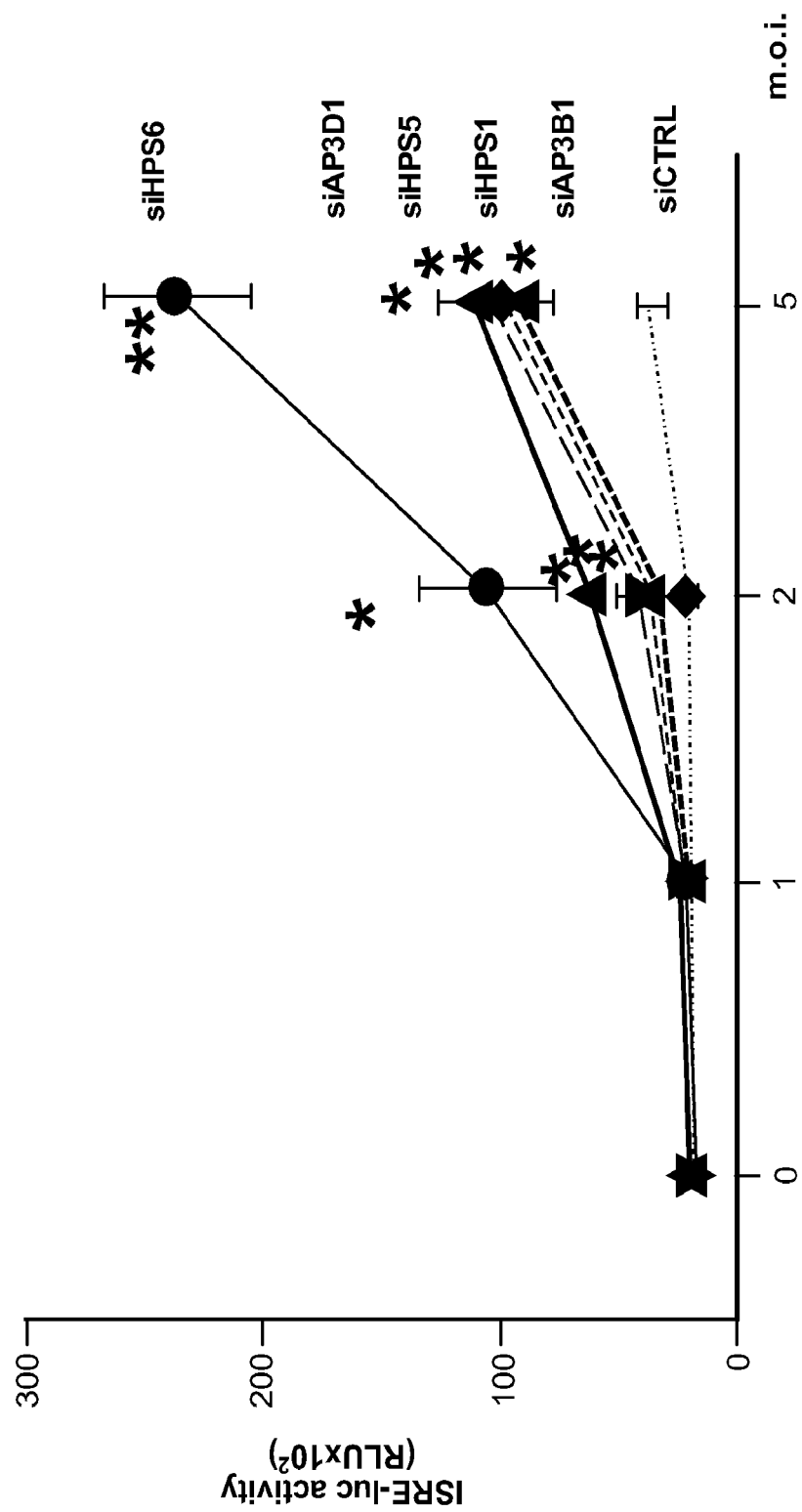

FIG. 5E

Red: influenza
Green: EEA1 (early endosome)

Control

HPS1 mutant

SEQUENCE LISTING

<160> NUMBER OF SEQ ID NOS: 108

<210> SEQ ID NO 1
<211> LENGTH: 21
<212> TYPE: DNA
<213> ORGANISM: Homo sapiens

<400> SEQUENCE: 1
gcaagctgtt ggctttctac t                                        21

<210> SEQ ID NO 2
<211> LENGTH: 21
<212> TYPE: DNA
<213> ORGANISM: Homo sapiens

<400> SEQUENCE: 2
gcaagctgtt ggctttctac t                                        21

<210> SEQ ID NO 3
<211> LENGTH: 21
<212> TYPE: DNA
<213> ORGANISM: Homo sapiens

<400> SEQUENCE: 3
gccagaagat ggacaagttt a                                        21

<210> SEQ ID NO 4
<211> LENGTH: 21
<212> TYPE: DNA
<213> ORGANISM: Homo sapiens

<400> SEQUENCE: 4
gccagaagat ggacaagttt a                                        21

<210> SEQ ID NO 5
<211> LENGTH: 21
<212> TYPE: DNA
<213> ORGANISM: Homo sapiens

<400> SEQUENCE: 5
tacgtttacc ttgtccgata t                                        21

<210> SEQ ID NO 6
<211> LENGTH: 21
<212> TYPE: DNA
<213> ORGANISM: Homo sapiens

<400> SEQUENCE: 6
caagcatcct ttggctaatt g                                        21

<210> SEQ ID NO 7
<211> LENGTH: 21
<212> TYPE: DNA
<213> ORGANISM: Homo sapiens

<400> SEQUENCE: 7
gcatctgttt ggagagtacc t                                        21

<210> SEQ ID NO 8
<211> LENGTH: 21
<212> TYPE: DNA
<213> ORGANISM: Homo sapiens

<400> SEQUENCE: 8

```
ttggtgaaga gccggagaaa t                                              21

<210> SEQ ID NO 9
<211> LENGTH: 21
<212> TYPE: DNA
<213> ORGANISM: Homo sapiens

<400> SEQUENCE: 9
gcatctgttt ggagagtacc t                                              21

<210> SEQ ID NO 10
<211> LENGTH: 21
<212> TYPE: DNA
<213> ORGANISM: Homo sapiens

<400> SEQUENCE: 10
acagatcacc ctgactaata c                                              21

<210> SEQ ID NO 11
<211> LENGTH: 21
<212> TYPE: DNA
<213> ORGANISM: Homo sapiens

<400> SEQUENCE: 11
tggctgtcgc tcagctatat t                                              21

<210> SEQ ID NO 12
<211> LENGTH: 21
<212> TYPE: DNA
<213> ORGANISM: Homo sapiens

<400> SEQUENCE: 12
gcttggcaat cgtccttctt a                                              21

<210> SEQ ID NO 13
<211> LENGTH: 21
<212> TYPE: DNA
<213> ORGANISM: Homo sapiens

<400> SEQUENCE: 13
gcttggcaat cgtccttctt a                                              21

<210> SEQ ID NO 14
<211> LENGTH: 21
<212> TYPE: DNA
<213> ORGANISM: Homo sapiens

<400> SEQUENCE: 14
accacatagt ccatcgaaga a                                              21

<210> SEQ ID NO 15
<211> LENGTH: 21
<212> TYPE: DNA
<213> ORGANISM: Homo sapiens

<400> SEQUENCE: 15
catagtccat cgaagaagag t                                              21

<210> SEQ ID NO 16
<211> LENGTH: 21
<212> TYPE: DNA
<213> ORGANISM: Homo sapiens
```

```
<400> SEQUENCE: 16
gtatcggcaa gcagtgtaaa c                                              21

<210> SEQ ID NO 17
<211> LENGTH: 21
<212> TYPE: DNA
<213> ORGANISM: Homo sapiens

<400> SEQUENCE: 17
cagttgtgta gcagttgagt a                                              21

<210> SEQ ID NO 18
<211> LENGTH: 21
<212> TYPE: DNA
<213> ORGANISM: Homo sapiens

<400> SEQUENCE: 18
agttgtgtag cagttgagta a                                              21

<210> SEQ ID NO 19
<211> LENGTH: 21
<212> TYPE: DNA
<213> ORGANISM: Homo sapiens

<400> SEQUENCE: 19
tctcccgatt gctcctgtgt a                                              21

<210> SEQ ID NO 20
<211> LENGTH: 21
<212> TYPE: DNA
<213> ORGANISM: Homo sapiens

<400> SEQUENCE: 20
gagtgcttgg ctgtttcctg t                                              21

<210> SEQ ID NO 21
<211> LENGTH: 21
<212> TYPE: DNA
<213> ORGANISM: Homo sapiens

<400> SEQUENCE: 21
gcaagtattc tttggctaat t                                              21

<210> SEQ ID NO 22
<211> LENGTH: 21
<212> TYPE: DNA
<213> ORGANISM: Homo sapiens

<400> SEQUENCE: 22
gcaagtattc tttggctaat t                                              21

<210> SEQ ID NO 23
<211> LENGTH: 21
<212> TYPE: DNA
<213> ORGANISM: Homo sapiens

<400> SEQUENCE: 23
cacatagtcc atcgaagaag a                                              21

<210> SEQ ID NO 24
<211> LENGTH: 21
<212> TYPE: DNA
<213> ORGANISM: Homo sapiens
```

<400> SEQUENCE: 24
gtcgtgcaga aacaaatggc t                                    21

<210> SEQ ID NO 25
<211> LENGTH: 21
<212> TYPE: DNA
<213> ORGANISM: Homo sapiens

<400> SEQUENCE: 25
aggactagct gcccattatt t                                    21

<210> SEQ ID NO 26
<211> LENGTH: 21
<212> TYPE: DNA
<213> ORGANISM: Homo sapiens

<400> SEQUENCE: 26
ccacatagtc catcgaagaa g                                    21

<210> SEQ ID NO 27
<211> LENGTH: 21
<212> TYPE: DNA
<213> ORGANISM: Homo sapiens

<400> SEQUENCE: 27
ttgctcctgt gtaaagatgc c                                    21

<210> SEQ ID NO 28
<211> LENGTH: 21
<212> TYPE: DNA
<213> ORGANISM: Homo sapiens

<400> SEQUENCE: 28
cctgcatttg taccaacgaa a                                    21

<210> SEQ ID NO 29
<211> LENGTH: 21
<212> TYPE: DNA
<213> ORGANISM: Homo sapiens

<400> SEQUENCE: 29
gcagccacta ttcagactat a                                    21

<210> SEQ ID NO 30
<211> LENGTH: 21
<212> TYPE: DNA
<213> ORGANISM: Homo sapiens

<400> SEQUENCE: 30
gcagccacta ttcagactat a                                    21

<210> SEQ ID NO 31
<211> LENGTH: 21
<212> TYPE: DNA
<213> ORGANISM: Homo sapiens

<400> SEQUENCE: 31
cctgcatttg taccaacgaa a                                    21

<210> SEQ ID NO 32
<211> LENGTH: 21
<212> TYPE: DNA

<213> ORGANISM: Homo sapiens

<400> SEQUENCE: 32
atgtatcggc aagcagtgta a                                      21

<210> SEQ ID NO 33
<211> LENGTH: 21
<212> TYPE: DNA
<213> ORGANISM: Homo sapiens

<400> SEQUENCE: 33
acatagtcca tcgaagaaga g                                      21

<210> SEQ ID NO 34
<211> LENGTH: 21
<212> TYPE: DNA
<213> ORGANISM: Homo sapiens

<400> SEQUENCE: 34
tatcggcaag cagtgtaaac g                                      21

<210> SEQ ID NO 35
<211> LENGTH: 21
<212> TYPE: DNA
<213> ORGANISM: Homo sapiens

<400> SEQUENCE: 35
tgctaaccaa agagcatata t                                      21

<210> SEQ ID NO 36
<211> LENGTH: 21
<212> TYPE: DNA
<213> ORGANISM: Homo sapiens

<400> SEQUENCE: 36
ggcaagcagt gtaaacggag g                                      21

<210> SEQ ID NO 37
<211> LENGTH: 58
<212> TYPE: DNA
<213> ORGANISM: Artificial Sequence
<220> FEATURE:
<223> OTHER INFORMATION: chemically synthesized oligonucleotide

<400> SEQUENCE: 37
ccgggcaagc tgttggcttt ctactctcga gagtagaaag ccaacagctt gcttttg      58

<210> SEQ ID NO 38
<211> LENGTH: 58
<212> TYPE: DNA
<213> ORGANISM: Artificial Sequence
<220> FEATURE:
<223> OTHER INFORMATION: chemically synthesized oligonucleotide

<400> SEQUENCE: 38
ccgggcaagc tgttggcttt ctactctcga gagtagaaag ccaacagctt gcttttg      58

<210> SEQ ID NO 39
<211> LENGTH: 58
<212> TYPE: DNA
<213> ORGANISM: Artificial Sequence
<220> FEATURE:
<223> OTHER INFORMATION: chemically synthesized oligonucleotide

<400> SEQUENCE: 39
ccgggccaga agatggacaa gtttactcga gtaaacttgt ccatcttctg gctttttg    58

<210> SEQ ID NO 40
<211> LENGTH: 58
<212> TYPE: DNA
<213> ORGANISM: Artificial Sequence
<220> FEATURE:
<223> OTHER INFORMATION: chemically synthesized oligonucleotide

<400> SEQUENCE: 40
ccgggccaga agatggacaa gtttactcga gtaaacttgt ccatcttctg gctttttg    58

<210> SEQ ID NO 41
<211> LENGTH: 58
<212> TYPE: DNA
<213> ORGANISM: Artificial Sequence
<220> FEATURE:
<223> OTHER INFORMATION: chemically synthesized oligonucleotide

<400> SEQUENCE: 41
ccggtacgtt taccttgtcc gatatctcga gatatcggac aaggtaaacg tatttttg    58

<210> SEQ ID NO 42
<211> LENGTH: 58
<212> TYPE: DNA
<213> ORGANISM: Artificial Sequence
<220> FEATURE:
<223> OTHER INFORMATION: chemically synthesized oligonucleotide

<400> SEQUENCE: 42
ccggcaagca tcctttggct aattgctcga gcaattagcc aaaggatgct tgtttttg    58

<210> SEQ ID NO 43
<211> LENGTH: 58
<212> TYPE: DNA
<213> ORGANISM: Artificial Sequence
<220> FEATURE:
<223> OTHER INFORMATION: chemically synthesized oligonucleotide

<400> SEQUENCE: 43
ccgggcatct gtttggagag tacctctcga gaggtactct ccaaacagat gctttttg    58

<210> SEQ ID NO 44
<211> LENGTH: 58
<212> TYPE: DNA
<213> ORGANISM: Artificial Sequence
<220> FEATURE:
<223> OTHER INFORMATION: Chemically synthesized oligonucleotide

<400> SEQUENCE: 44
ccggttggtg aagagccgga gaaatctcga gatttctccg gctcttcacc aattttg    58

<210> SEQ ID NO 45
<211> LENGTH: 58
<212> TYPE: DNA
<213> ORGANISM: Artificial Sequence
<220> FEATURE:
<223> OTHER INFORMATION: Chemically synthesized oligonucleotide

<400> SEQUENCE: 45
ccgggcatct gtttggagag tacctctcga gaggtactct ccaaacagat gctttttg    58

<210> SEQ ID NO 46
<211> LENGTH: 58
<212> TYPE: DNA

<213> ORGANISM: Artificial Sequence
<220> FEATURE:
<223> OTHER INFORMATION: Chemically synthesized oligonucleotide

<400> SEQUENCE: 46
ccggacagat caccctgact aatacctcga ggtattagtc agggtgatct gttttttg        58

<210> SEQ ID NO 47
<211> LENGTH: 58
<212> TYPE: DNA
<213> ORGANISM: Artificial Sequence
<220> FEATURE:
<223> OTHER INFORMATION: Chemically synthesized oligonucleotide

<400> SEQUENCE: 47
ccggtggctg tcgctcagct atattctcga gaatatagct gagcgacagc cattttttg       58

<210> SEQ ID NO 48
<211> LENGTH: 58
<212> TYPE: DNA
<213> ORGANISM: Artificial Sequence
<220> FEATURE:
<223> OTHER INFORMATION: Chemically synthesized oligonucleotide

<400> SEQUENCE: 48
ccgggcttgg caatcgtcct tcttactcga gtaagaagga cgattgccaa gctttttg        58

<210> SEQ ID NO 49
<211> LENGTH: 58
<212> TYPE: DNA
<213> ORGANISM: Artificial Sequence
<220> FEATURE:
<223> OTHER INFORMATION: Chemically synthesized oligonucleotide

<400> SEQUENCE: 49
ccgggcttgg caatcgtcct tcttactcga gtaagaagga cgattgccaa gctttttg        58

<210> SEQ ID NO 50
<211> LENGTH: 58
<212> TYPE: DNA
<213> ORGANISM: Artificial Sequence
<220> FEATURE:
<223> OTHER INFORMATION: Chemically synthesized oligonucleotide

<400> SEQUENCE: 50
ccggaccaca tagtccatcg aagaactcga gttcttcgat ggactatgtg gttttttg       58

<210> SEQ ID NO 51
<211> LENGTH: 58
<212> TYPE: DNA
<213> ORGANISM: Artificial Sequence
<220> FEATURE:
<223> OTHER INFORMATION: Chemically synthesized oligonucleotide

<400> SEQUENCE: 51
ccggcatagt ccatcgaaga agagtctcga gactcttctt cgatggacta tgttttttg      58

<210> SEQ ID NO 52
<211> LENGTH: 58
<212> TYPE: DNA
<213> ORGANISM: Artificial Sequence
<220> FEATURE:
<223> OTHER INFORMATION: Chemically synthesized oligonucleotide

<400> SEQUENCE: 52
ccgggtatcg gcaagcagtg taaacctcga ggtttacact gcttgccgat acttttttg      58

<210> SEQ ID NO 53
<211> LENGTH: 58
<212> TYPE: DNA
<213> ORGANISM: Artificial Sequence
<220> FEATURE:
<223> OTHER INFORMATION: Chemically synthesized oligonucleotide

<400> SEQUENCE: 53
ccggcagttg tgtagcagtt gagtactcga gtactcaact gctacacaac tgttttttg    58

<210> SEQ ID NO 54
<211> LENGTH: 58
<212> TYPE: DNA
<213> ORGANISM: Artificial Sequence
<220> FEATURE:
<223> OTHER INFORMATION: Chemically synthesized oligonucleotide

<400> SEQUENCE: 54
ccggagttgt gtagcagttg agtaactcga gttactcaac tgctacacaa ctttttttg    58

<210> SEQ ID NO 55
<211> LENGTH: 58
<212> TYPE: DNA
<213> ORGANISM: Artificial Sequence
<220> FEATURE:
<223> OTHER INFORMATION: Chemically synthesized oligonucleotide

<400> SEQUENCE: 55
ccggtctccc gattgctcct gtgtactcga gtacacagga gcaatcggga gatttttttg    58

<210> SEQ ID NO 56
<211> LENGTH: 58
<212> TYPE: DNA
<213> ORGANISM: Artificial Sequence
<220> FEATURE:
<223> OTHER INFORMATION: Chemically synthesized oligonucleotide

<400> SEQUENCE: 56
ccgggagtgc ttggctgttt cctgtctcga gacaggaaac agccaagcac tctttttg    58

<210> SEQ ID NO 57
<211> LENGTH: 58
<212> TYPE: DNA
<213> ORGANISM: Artificial Sequence
<220> FEATURE:
<223> OTHER INFORMATION: Chemically synthesized oligonucleotide

<400> SEQUENCE: 57
ccgggcaagt attctttggc taattctcga gaattagcca agaatactt gctttttg    58

<210> SEQ ID NO 58
<211> LENGTH: 58
<212> TYPE: DNA
<213> ORGANISM: Artificial Sequence
<220> FEATURE:
<223> OTHER INFORMATION: Chemically synthesized oligonucleotide

<400> SEQUENCE: 58
ccgggcaagt attctttggc taattctcga gaattagcca agaatactt gctttttg    58

<210> SEQ ID NO 59
<211> LENGTH: 58
<212> TYPE: DNA
<213> ORGANISM: Artificial Sequence
<220> FEATURE:

<223> OTHER INFORMATION: Chemically synthesized oligonucleotide

<400> SEQUENCE: 59
ccggcacata gtccatcgaa gaagactcga gtcttcttcg atggactatg tgttttttg    58

<210> SEQ ID NO 60
<211> LENGTH: 58
<212> TYPE: DNA
<213> ORGANISM: Artificial Sequence
<220> FEATURE:
<223> OTHER INFORMATION: Chemically synthesized oligonucleotide

<400> SEQUENCE: 60
ccgggtcgtg cagaaacaaa tggctctcga gagccatttg tttctgcacg acttttttg    58

<210> SEQ ID NO 61
<211> LENGTH: 58
<212> TYPE: DNA
<213> ORGANISM: Artificial Sequence
<220> FEATURE:
<223> OTHER INFORMATION: Chemically synthesized oligonucleotide

<400> SEQUENCE: 61
ccggaggact agctgcccat tatttctcga gaaataatgg gcagctagtc cttttttg     58

<210> SEQ ID NO 62
<211> LENGTH: 58
<212> TYPE: DNA
<213> ORGANISM: Artificial Sequence
<220> FEATURE:
<223> OTHER INFORMATION: Chemically synthesized oligonucleotide

<400> SEQUENCE: 62
ccggccacat agtccatcga agaagctcga gcttcttcga tggactatgt ggtttttg     58

<210> SEQ ID NO 63
<211> LENGTH: 58
<212> TYPE: DNA
<213> ORGANISM: Artificial Sequence
<220> FEATURE:
<223> OTHER INFORMATION: Chemically synthesized oligonucleotide

<400> SEQUENCE: 63
ccggttgctc ctgtgtaaag atgccctcga gggcatcttt acacaggagc aatttttg    58

<210> SEQ ID NO 64
<211> LENGTH: 58
<212> TYPE: DNA
<213> ORGANISM: Artificial Sequence
<220> FEATURE:
<223> OTHER INFORMATION: Chemically synthesized oligonucleotide

<400> SEQUENCE: 64
ccggcctgca tttgtaccaa cgaaactcga gtttcgttgg tacaaatgca ggtttttg    58

<210> SEQ ID NO 65
<211> LENGTH: 58
<212> TYPE: DNA
<213> ORGANISM: Artificial Sequence
<220> FEATURE:
<223> OTHER INFORMATION: Chemically synthesized oligonucleotide

<400> SEQUENCE: 65
ccgggcagcc actattcaga ctatactcga gtatagtctg aatagtggct gcttttttg   58

```
<210> SEQ ID NO 66
<211> LENGTH: 58
<212> TYPE: DNA
<213> ORGANISM: Artificial Sequence
<220> FEATURE:
<223> OTHER INFORMATION: Chemically synthesized oligonucleotide

<400> SEQUENCE: 66
ccgggcagcc actattcaga ctatactcga gtatagtctg aatagtggct gcttttg          58

<210> SEQ ID NO 67
<211> LENGTH: 58
<212> TYPE: DNA
<213> ORGANISM: Artificial Sequence
<220> FEATURE:
<223> OTHER INFORMATION: Chemically synthesized oligonucleotide

<400> SEQUENCE: 67
ccggcctgca tttgtaccaa cgaaactcga gtttcgttgg tacaaatgca ggttttg          58

<210> SEQ ID NO 68
<211> LENGTH: 58
<212> TYPE: DNA
<213> ORGANISM: Artificial Sequence
<220> FEATURE:
<223> OTHER INFORMATION: Chemically synthesized oligonucleotide

<400> SEQUENCE: 68
ccggatgtat cggcaagcag tgtaactcga gttacactgc ttgccgatac attttg          58

<210> SEQ ID NO 69
<211> LENGTH: 58
<212> TYPE: DNA
<213> ORGANISM: Artificial Sequence
<220> FEATURE:
<223> OTHER INFORMATION: Chemically synthesized oligonucleotide

<400> SEQUENCE: 69
ccggacatag tccatcgaag aagagctcga gctcttcttc gatggactat gttttg          58

<210> SEQ ID NO 70
<211> LENGTH: 58
<212> TYPE: DNA
<213> ORGANISM: Artificial Sequence
<220> FEATURE:
<223> OTHER INFORMATION: Chemically synthesized oligonucleotide

<400> SEQUENCE: 70
ccggtatcgg caagcagtgt aaacgctcga gcgtttacac tgcttgccga tattttg          58

<210> SEQ ID NO 71
<211> LENGTH: 58
<212> TYPE: DNA
<213> ORGANISM: Artificial Sequence
<220> FEATURE:
<223> OTHER INFORMATION: Chemically synthesized oligonucleotide

<400> SEQUENCE: 71
ccggtgctaa ccaaagagca tatatctcga gatatatgct ctttggttag cattttg          58

<210> SEQ ID NO 72
<211> LENGTH: 58
<212> TYPE: DNA
<213> ORGANISM: Artificial Sequence
<220> FEATURE:
<223> OTHER INFORMATION: Chemically synthesized oligonucleotide
```

<400> SEQUENCE: 72
ccggggcaag cagtgtaaac ggaggctcga gcctccgttt acactgcttg ccttttttg    58

<210> SEQ ID NO 73
<211> LENGTH: 58
<212> TYPE: DNA
<213> ORGANISM: Artificial Sequence
<220> FEATURE:
<223> OTHER INFORMATION: Chemically synthesized oligonucleotide

<400> SEQUENCE: 73
aattcaaaaa gcaagctgtt ggctttctac tctcgagagt agaaagccaa cagcttgc    58

<210> SEQ ID NO 74
<211> LENGTH: 58
<212> TYPE: DNA
<213> ORGANISM: Artificial Sequence
<220> FEATURE:
<223> OTHER INFORMATION: Chemically synthesized oligonucleotide

<400> SEQUENCE: 74
aattcaaaaa gcaagctgtt ggctttctac tctcgagagt agaaagccaa cagcttgc    58

<210> SEQ ID NO 75
<211> LENGTH: 58
<212> TYPE: DNA
<213> ORGANISM: Artificial Sequence
<220> FEATURE:
<223> OTHER INFORMATION: Chemically synthesized oligonucleotide

<400> SEQUENCE: 75
aattcaaaaa gccagaagat ggacaagttt actcgagtaa acttgtccat cttctggc    58

<210> SEQ ID NO 76
<211> LENGTH: 58
<212> TYPE: DNA
<213> ORGANISM: Artificial Sequence
<220> FEATURE:
<223> OTHER INFORMATION: Chemically synthesized oligonucleotide

<400> SEQUENCE: 76
aattcaaaaa gccagaagat ggacaagttt actcgagtaa acttgtccat cttctggc    58

<210> SEQ ID NO 77
<211> LENGTH: 58
<212> TYPE: DNA
<213> ORGANISM: Artificial Sequence
<220> FEATURE:
<223> OTHER INFORMATION: Chemically synthesized oligonucleotide

<400> SEQUENCE: 77
aattcaaaaa tacgtttacc ttgtccgata tctcgagata tcggacaagg taaacgta    58

<210> SEQ ID NO 78
<211> LENGTH: 58
<212> TYPE: DNA
<213> ORGANISM: Artificial Sequence
<220> FEATURE:
<223> OTHER INFORMATION: Chemically synthesized oligonucleotide

<400> SEQUENCE: 78
aattcaaaaa caagcatcct ttggctaatt gctcgagcaa ttagccaaag gatgcttg    58

<210> SEQ ID NO 79
<211> LENGTH: 58

<212> TYPE: DNA
<213> ORGANISM: Artificial Sequence
<220> FEATURE:
<223> OTHER INFORMATION: Chemically synthesized oligonucleotide

<400> SEQUENCE: 79
aattcaaaaa gcatctgttt ggagagtacc tctcgagagg tactctccaa acagatgc        58

<210> SEQ ID NO 80
<211> LENGTH: 58
<212> TYPE: DNA
<213> ORGANISM: Artificial Sequence
<220> FEATURE:
<223> OTHER INFORMATION: Chemically synthesized oligonucleotide

<400> SEQUENCE: 80
aattcaaaaa ttggtgaaga gccggagaaa tctcgagatt tctccggctc ttcaccaa        58

<210> SEQ ID NO 81
<211> LENGTH: 58
<212> TYPE: DNA
<213> ORGANISM: Artificial Sequence
<220> FEATURE:
<223> OTHER INFORMATION: Chemically synthesized oligonucleotide

<400> SEQUENCE: 81
aattcaaaaa gcatctgttt ggagagtacc tctcgagagg tactctccaa acagatgc        58

<210> SEQ ID NO 82
<211> LENGTH: 58
<212> TYPE: DNA
<213> ORGANISM: Artificial Sequence
<220> FEATURE:
<223> OTHER INFORMATION: Chemically synthesized oligonucleotide

<400> SEQUENCE: 82
aattcaaaaa acagatcacc ctgactaata cctcgaggta ttagtcaggg tgatctgt        58

<210> SEQ ID NO 83
<211> LENGTH: 58
<212> TYPE: DNA
<213> ORGANISM: Artificial Sequence
<220> FEATURE:
<223> OTHER INFORMATION: Chemically synthesized oligonucleotide

<400> SEQUENCE: 83
aattcaaaaa tggctgtcgc tcagctatat tctcgagaat atagctgagc gacagcca        58

<210> SEQ ID NO 84
<211> LENGTH: 58
<212> TYPE: DNA
<213> ORGANISM: Artificial Sequence
<220> FEATURE:
<223> OTHER INFORMATION: Chemically synthesized oligonucleotide

<400> SEQUENCE: 84
aattcaaaaa gcttggcaat cgtccttctt actcgagtaa gaaggacgat tgccaagc        58

<210> SEQ ID NO 85
<211> LENGTH: 58
<212> TYPE: DNA
<213> ORGANISM: Artificial Sequence
<220> FEATURE:
<223> OTHER INFORMATION: Chemically synthesized oligonucleotide

<400> SEQUENCE: 85
aattcaaaaa gcttggcaat cgtccttctt actcgagtaa gaaggacgat tgccaagc        58

<210> SEQ ID NO 86
<211> LENGTH: 58
<212> TYPE: DNA
<213> ORGANISM: Artificial Sequence
<220> FEATURE:
<223> OTHER INFORMATION: Chemically synthesized oligonucleotide

<400> SEQUENCE: 86
aattcaaaaa accacatagt ccatcgaaga actcgagttc ttcgatggac tatgtggt        58

<210> SEQ ID NO 87
<211> LENGTH: 58
<212> TYPE: DNA
<213> ORGANISM: Artificial Sequence
<220> FEATURE:
<223> OTHER INFORMATION: Chemically synthesized oligonucleotide

<400> SEQUENCE: 87
aattcaaaaa catagtccat cgaagaagag tctcgagact cttcttcgat ggactatg        58

<210> SEQ ID NO 88
<211> LENGTH: 58
<212> TYPE: DNA
<213> ORGANISM: Artificial Sequence
<220> FEATURE:
<223> OTHER INFORMATION: Chemically synthesized oligonucleotide

<400> SEQUENCE: 88
aattcaaaaa gtatcggcaa gcagtgtaaa cctcgaggtt tacactgctt gccgatac        58

<210> SEQ ID NO 89
<211> LENGTH: 58
<212> TYPE: DNA
<213> ORGANISM: Artificial Sequence
<220> FEATURE:
<223> OTHER INFORMATION: Chemically synthesized oligonucleotide

<400> SEQUENCE: 89
aattcaaaaa cagttgtgta gcagttgagt actcgagtac tcaactgcta cacaactg        58

<210> SEQ ID NO 90
<211> LENGTH: 58
<212> TYPE: DNA
<213> ORGANISM: Artificial Sequence
<220> FEATURE:
<223> OTHER INFORMATION: Chemically synthesized oligonucleotide

<400> SEQUENCE: 90
aattcaaaaa agttgtgtag cagttgagta actcgagtta ctcaactgct acacaact        58

<210> SEQ ID NO 91
<211> LENGTH: 58
<212> TYPE: DNA
<213> ORGANISM: Artificial Sequence
<220> FEATURE:
<223> OTHER INFORMATION: Chemically synthesized oligonucleotide

<400> SEQUENCE: 91
aattcaaaaa tctcccgatt gctcctgtgt actcgagtac acaggagcaa tcgggaga        58

<210> SEQ ID NO 92
<211> LENGTH: 58
<212> TYPE: DNA
<213> ORGANISM: Artificial Sequence

```
<220> FEATURE:
<223> OTHER INFORMATION: Chemically synthesized oligonucleotide

<400> SEQUENCE: 92
aattcaaaaa gagtgcttgg ctgtttcctg tctcgagaca ggaaacagcc aagcactc        58

<210> SEQ ID NO 93
<211> LENGTH: 58
<212> TYPE: DNA
<213> ORGANISM: Artificial Sequence
<220> FEATURE:
<223> OTHER INFORMATION: Chemically synthesized oligonucleotide

<400> SEQUENCE: 93
aattcaaaaa gcaagtattc tttggctaat tctcgagaat tagccaaaga atacttgc        58

<210> SEQ ID NO 94
<211> LENGTH: 58
<212> TYPE: DNA
<213> ORGANISM: Artificial Sequence
<220> FEATURE:
<223> OTHER INFORMATION: Chemically synthesized oligonucleotide

<400> SEQUENCE: 94
aattcaaaaa gcaagtattc tttggctaat tctcgagaat tagccaaaga atacttgc        58

<210> SEQ ID NO 95
<211> LENGTH: 58
<212> TYPE: DNA
<213> ORGANISM: Artificial Sequence
<220> FEATURE:
<223> OTHER INFORMATION: Chemically synthesized oligonucleotide

<400> SEQUENCE: 95
aattcaaaaa cacatagtcc atcgaagaag actcgagtct tcttcgatgg actatgtg        58

<210> SEQ ID NO 96
<211> LENGTH: 58
<212> TYPE: DNA
<213> ORGANISM: Artificial Sequence
<220> FEATURE:
<223> OTHER INFORMATION: Chemically synthesized oligonucleotide

<400> SEQUENCE: 96
aattcaaaaa gtcgtgcaga aacaaatggc tctcgagagc catttgtttc tgcacgac        58

<210> SEQ ID NO 97
<211> LENGTH: 58
<212> TYPE: DNA
<213> ORGANISM: Artificial Sequence
<220> FEATURE:
<223> OTHER INFORMATION: Chemically synthesized oligonucleotide

<400> SEQUENCE: 97
aattcaaaaa aggactagct gcccattatt tctcgagaaa taatgggcag ctagtcct        58

<210> SEQ ID NO 98
<211> LENGTH: 58
<212> TYPE: DNA
<213> ORGANISM: Artificial Sequence
<220> FEATURE:
<223> OTHER INFORMATION: Chemically synthesized oligonucleotide

<400> SEQUENCE: 98
aattcaaaaa ccacatagtc catcgaagaa gctcgagctt cttcgatgga ctatgtgg        58
```

<210> SEQ ID NO 99
<211> LENGTH: 58
<212> TYPE: DNA
<213> ORGANISM: Artificial Sequence
<220> FEATURE:
<223> OTHER INFORMATION: Chemically synthesized oligonucleotide

<400> SEQUENCE: 99
aattcaaaaa ttgctcctgt gtaaagatgc cctcgagggc atctttacac aggagcaa         58

<210> SEQ ID NO 100
<211> LENGTH: 58
<212> TYPE: DNA
<213> ORGANISM: Artificial Sequence
<220> FEATURE:
<223> OTHER INFORMATION: Chemically synthesized oligonucleotide

<400> SEQUENCE: 100
aattcaaaaa cctgcatttg taccaacgaa actcgagttt cgttggtaca aatgcagg         58

<210> SEQ ID NO 101
<211> LENGTH: 58
<212> TYPE: DNA
<213> ORGANISM: Artificial Sequence
<220> FEATURE:
<223> OTHER INFORMATION: Chemically synthesized oligonucleotide

<400> SEQUENCE: 101
aattcaaaaa gcagccacta ttcagactat actcgagtat agtctgaata gtggctgc         58

<210> SEQ ID NO 102
<211> LENGTH: 58
<212> TYPE: DNA
<213> ORGANISM: Artificial Sequence
<220> FEATURE:
<223> OTHER INFORMATION: Chemically synthesized oligonucleotide

<400> SEQUENCE: 102
aattcaaaaa gcagccacta ttcagactat actcgagtat agtctgaata gtggctgc         58

<210> SEQ ID NO 103
<211> LENGTH: 58
<212> TYPE: DNA
<213> ORGANISM: Artificial Sequence
<220> FEATURE:
<223> OTHER INFORMATION: Chemically synthesized oligonucleotide

<400> SEQUENCE: 103
aattcaaaaa cctgcatttg taccaacgaa actcgagttt cgttggtaca aatgcagg         58

<210> SEQ ID NO 104
<211> LENGTH: 58
<212> TYPE: DNA
<213> ORGANISM: Artificial Sequence
<220> FEATURE:
<223> OTHER INFORMATION: Chemically synthesized oligonucleotide

<400> SEQUENCE: 104
aattcaaaaa atgtatcggc aagcagtgta actcgagtta cactgcttgc cgatacat         58

<210> SEQ ID NO 105
<211> LENGTH: 58
<212> TYPE: DNA
<213> ORGANISM: Artificial Sequence
<220> FEATURE:
<223> OTHER INFORMATION: Chemically synthesized oligonucleotide

```
<400> SEQUENCE: 105
aattcaaaaa acatagtcca tcgaagaaga gctcgagctc ttcttcgatg gactatgt        58

<210> SEQ ID NO 106
<211> LENGTH: 58
<212> TYPE: DNA
<213> ORGANISM: Artificial Sequence
<220> FEATURE:
<223> OTHER INFORMATION: Chemically synthesized oligonucleotide

<400> SEQUENCE: 106
aattcaaaaa tatcggcaag cagtgtaaac gctcgagcgt ttacactgct tgccgata        58

<210> SEQ ID NO 107
<211> LENGTH: 58
<212> TYPE: DNA
<213> ORGANISM: Artificial Sequence
<220> FEATURE:
<223> OTHER INFORMATION: Chemically synthesized oligonucleotide

<400> SEQUENCE: 107
aattcaaaaa tgctaaccaa agagcatata tctcgagata tatgctcttt ggttagca        58

<210> SEQ ID NO 108
<211> LENGTH: 58
<212> TYPE: DNA
<213> ORGANISM: Artificial Sequence
<220> FEATURE:
<223> OTHER INFORMATION: Chemically synthesized oligonucleotide

<400> SEQUENCE: 108
aattcaaaaa ggcaagcagt gtaaacggag gctcgagcct ccgtttacac tgcttgcc        58
```

METHOD AND CELLS FOR THE PRODUCTION OF VIRAL VACCINES

RELATED APPLICATIONS

This application is a national stage application, filed under 35 U.S.C. § 371, of International Application No. PCT/US2013/021002, filed Jan. 10, 2013, which claims priority to and benefit of provisional application U.S. Ser. No. 61/585,006 filed on Jan. 10, 2012, the contents of which are herein incorporated by reference in their entireties.

STATEMENT OF RIGHTS TO INVENTIONS MADE UNDER FEDERALLY SPONSORED RESEARCH

This invention was made with government support under Grant No. U01 AI074575 awarded by the National Institutes of Health. The government has certain rights in the invention.

INCORPORATION OF SEQUENCE LISTING

The contents of the text file named "39564-514001WO_ST25.txt," which was created on Jan. 4, 2013 and is 20.3 KB in size, are hereby incorporated by reference in their entirety.

FIELD OF THE INVENTION

The present invention relates to vaccine products for the treatment or prevention of viral infections. Specifically, the invention provides genetically modified cells that when virally infected have increased viral production.

BACKGROUND OF THE INVENTION

Immunization to protect against communicable disease is one of the most successful and cost-effective practices of modern medicine. Smallpox has been completely eliminated by vaccination, and the incidence of many other diseases such as polio and diphtheria has been drastically reduced through immunization programs.

Most existing licensed vaccines and vaccines in development, whether based on inactivated viruses or recombinant DNA technology, rely primarily on immune responses to the mature virus, or, in a few examples of experimental, recombinant DNA-based vaccines, immune responses to antigens found in the cell-associated form of the virus, or virus-infected cells. Both the killed virus and attenuated virus approaches on the one hand and the recombinant DNA approaches on the other hand have their advantages and their limitations. While the cell culture and embryonated egg methods are used to grow whole virus very inexpensively, they are not very efficient methods for the commercial production of the viral precursor proteins found in the infected cells and the cell-associated forms of the virus. Production of viral vaccine proteins in insect or mammalian cells by recombinant methods is generally more expensive on a per milligram protein basis than cell culture and egg production methods.

Adverse reactions from vaccines may arise from impurities or from biologic properties of the vaccine proteins (antigens) responsible for conferring protective immunity. For example, the contaminating egg protein present in the licensed influenza vaccines may be largely responsible for the adverse reactions associated with these products.

Current production of human influenza vaccine takes place primarily in fertile chicken eggs. Several hundred million of eggs worldwide are used each year to produce vaccine for the influenza season. The current production cycle (beginning with identification of the anticipated virus strains expected to be present in the forthcoming influenza season) is many months long. The current production processes that use fertile eggs is labor intensive, expensive and fraught with variables, such as the seasonal availability and variation of properties of the eggs.

It would therefore be desirable to provide improved virus vaccine preparations that do not exhibit as many of the limitations and drawbacks observed with the use of currently available vaccines.

SUMMARY OF THE INVENTION

In one aspect, the invention provides a cell having a disruption of a gene where the disruption results in decreased expression or activity of the gene. The gene is for example on or more genes selected from Tables 1a or 1b. In one embodiment, the one or more genes are selected from the group consisting of HPS5, HPS1, AP3B1, AP3D, SC35, APPBP1, CEBPB, NFE2L2, NUP98, PDGFRL, PPP1R1c, SFRS2, SNAI2, TAF5L, TJP2, TMEM14C, ZNFF331 and ZNF498. The cell is infected with a virus of interest. The cell when infected with a virus exhibits increased viral replication relative to a wild-type cell. The virus is for example an influenza virus, an Ebola virus, or a Marburg virus. The cell is a vertebrate cell, such as a mammalian cell. The mammalian cell is from a human, hamster, cattle, monkey, dog or human.

In another aspect, the invention provides a method for replicating a virus by providing a culture of the cells having a disruption of a gene where the disruption results in decreased expression or activity of the gene; infecting the culture with a virus; and culturing the infected cell culture to replicate the virus. Optionally, the method further includes isolating the virus.

In yet another aspect, the invention provides a process of making a vaccine by providing a culture of the cells having a disruption of a gene where the disruption results in decreased expression or activity of the gene; infecting the culture with a virus; culturing the infected cell culture to replicate the virus; isolating the virus replicated in the previous step and formulating the virus to provide the vaccine. In some embodiments the vaccine contains disintegrated virus.

In another aspect, the present invention provides a process of replicating a virus comprising injecting a fertilized egg with a virus and a compound that inhibits the expression or activity of one or more genes listed in Tables 1a or 1b; and incubating the egg for a predetermined period of time to replicate the virus. In one aspect, the fertilized egg is a fertilized chicken egg.

In another aspect, the present invention provides a process of replicating a virus comprising injecting a cell with a virus and a compound that inhibits the expression or activity of one or more genes listed in Tables 1a or 1b; and incubating the cell for a predetermined period of time to replicate the virus. In some aspects, the cell comprises a disruption of one or more genes listed in Tables 1a or 1b, wherein the disruption results in decreased expression or activity of the one or more genes in the cell. The cell is a vertebrate cell. In some embodiments, the cell is a mammalian cell. For example, the cell is from a human, hamster, cattle, monkey, dog or human.

In some embodiments, the process of replicating a virus further comprises isolating the replicated virus. The compound is a nucleic acid, for example, the nucleic acid is a siRNA.

In yet another aspect, the present invention provides a method of making a vaccine comprising formulating the replicated virus into a vaccine.

Also included in the invention is a transgenic non-human animal whose genome contains a homozygous disruption of one or more genes listed on Tables 1a or 1b. The transgenic non-human animal is for example a bird, such as a chicken.

Unless otherwise defined, all technical and scientific terms used herein have the same meaning as commonly understood by one of ordinary skill in the art to which this invention pertains. Although methods and materials similar or equivalent to those described herein can be used in the practice of the present invention, suitable methods and materials are described below. All publications, patent applications, patents, and other references mentioned herein are expressly incorporated by reference in their entirety. In cases of conflict, the present specification, including definitions, will control. In addition, the materials, methods, and examples described herein are illustrative only and are not intended to be limiting.

Other features and advantages of the invention will be apparent from and encompassed by the following detailed description and claims.

C. and unbound virus was removed by vigorous washes. Flow cytometry was used to quantify virus based on DiD fluorescence intensity. (C) Virus internalization is unchanged in NHLF and HPS1-mutant cells. Cells were inoculated with Alexa 647-labeled X31 virus for 45 minutes. Cells were then fixed and anti-Alexa 647 antibody was used to probe non-internalized virus. Data is shown as mean+/−SD. (D) Absence of HPS1 enhances an envelope-dependent stage of influenza entry. Primary fibroblasts from three control patients and an HPS1 patient were incubated with MLV-eGFP virus pseudotyped with the PR8 HA and NA proteins. 48 hours after infection, GFP was quantified by flow cytometry. Relative infection of HPS1-mutant cells by GFP-expressing pseudovirus is expressed as the ratio of the number of GFP+ cells in HPS1-mutant cells to the number of GFP+ cells in control cells (average of three independent controls). Values represent mean+/−SEM, n=3. (E) HPS1 restricts entry of multiple influenza subtypes. NHLF and HPS1-mutant cells were incubated with the following MLV-eGFP pseudotypes: H3 (A/Udorn/72), H5 (A/Thailand2(SP-33)/2004), H7 (FPV): A/FPV/Rostock/34). MLV-env was used as a negative control. Values represent mean+/−SEM, n=3.

Figure 5D:
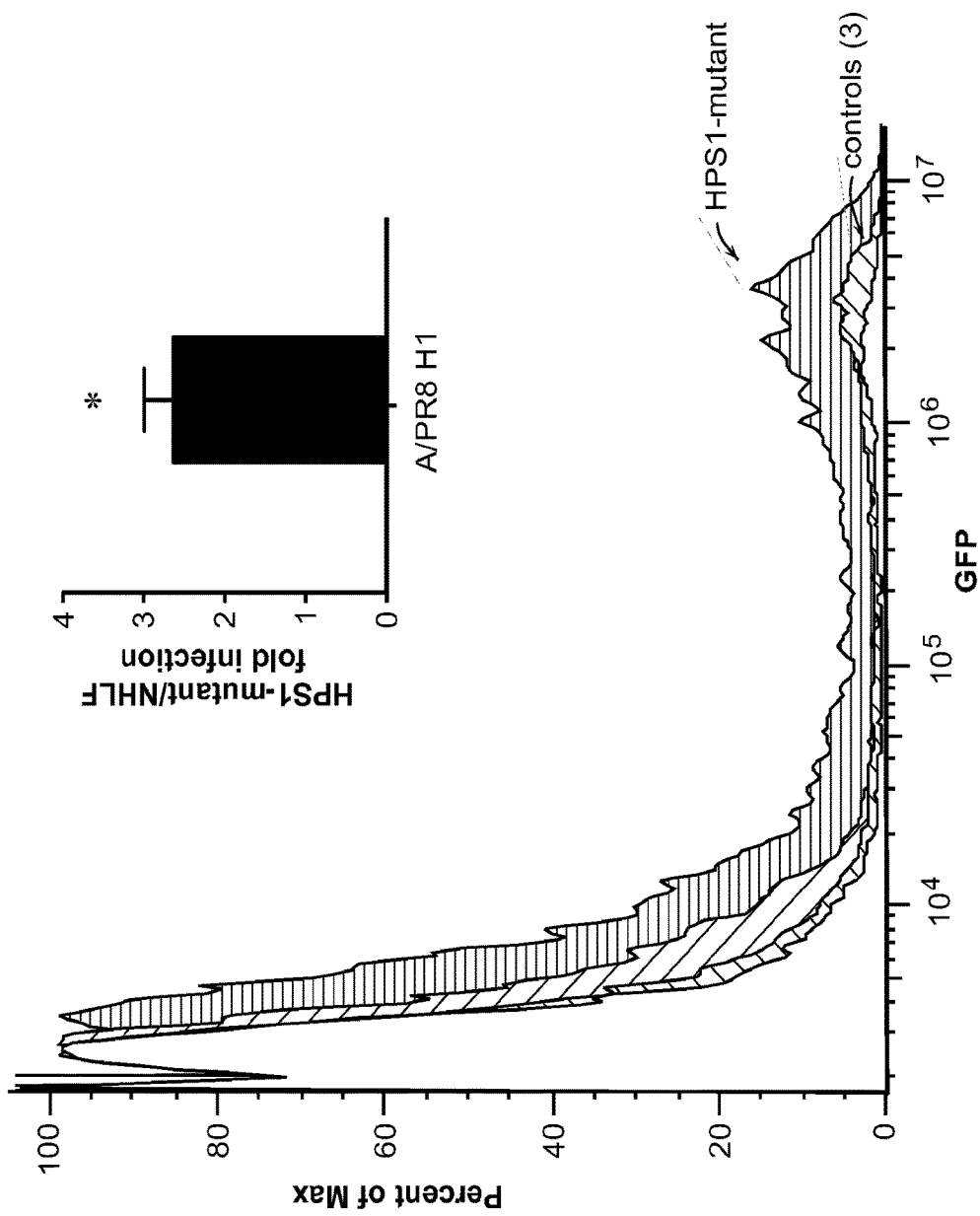
Figure 6A:
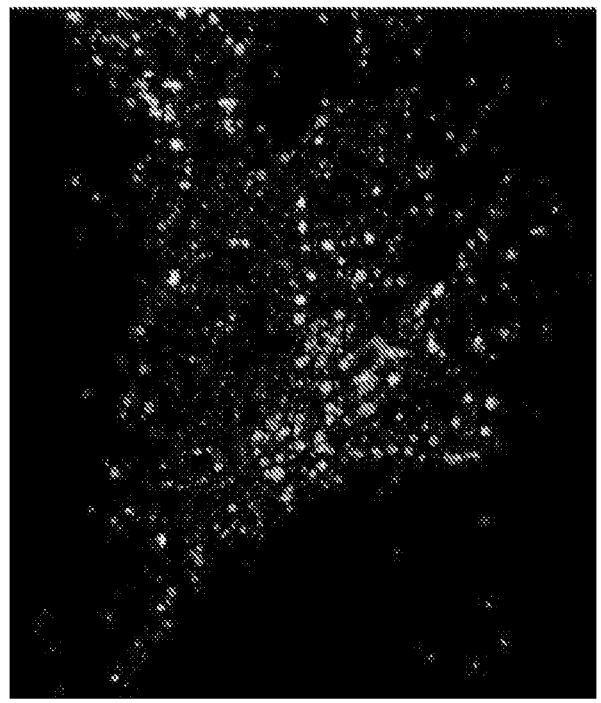
Figure 6A:

FIG. 6. Loss of HPS1 leads to increased viral fusion. (A) HPS1 does not affect influenza co-localization with early endosomes. HPS1-mutant and wild-type cells were infected with Alexa 647-labeled X31 virus. Cells were fixed and stained with anti-EEA1 antibody at 20 mins post-infection. Co-localization was determined using ImageJ. (B) HPS1-mutant cells permit higher levels of viral fusion with endosomal compartments. DiD-labeled X31 virus was incubated with NHLF or HPS1 patient cells on ice and then placed at 37° C. At the indicated times, cells were washed, fixed, and analyzed using flow cytometry (left panel) or confocal microscopy (right panel, representative of over 30 images in 2 experiments). Viral fusion is expressed as the percentage of DiD+ cells relative to the average of the control cells. Values represent mean+/−SEM, n=3. (C) HPS1-mutant cells permit increased entry of filovirus pseudotypes but not arenavirus pseudotypes. NHLF and HPS1-mut cells were incubated with the following MLV-eGFP pseudotypes: EBOV glycoprotein (Ebola virus), MARV glycoprotein (Marburg virus), MLV envelope (moloney leukemia virus), MACH (Machupo virus glycoprotein), LASV (Lassa virus glycoprotein) and LCMV (lymphchoriomeningitis glycoprotein). Relative infection calculated as in FIG. 5D. Values represent mean+/−SEM, n=3. P<0.05. (D) Schematic diagram of entry pathways of distinct viruses. FLU, EBOV and MARV pass through early endosomes to late endosomes, while LASV and LCMV enter late endosomes independent of early endosomes. MACV utilizes transferrin as a receptor, and passes from recycling endosomes to late endosomes through an unknown mechanism.

Figure 7A:
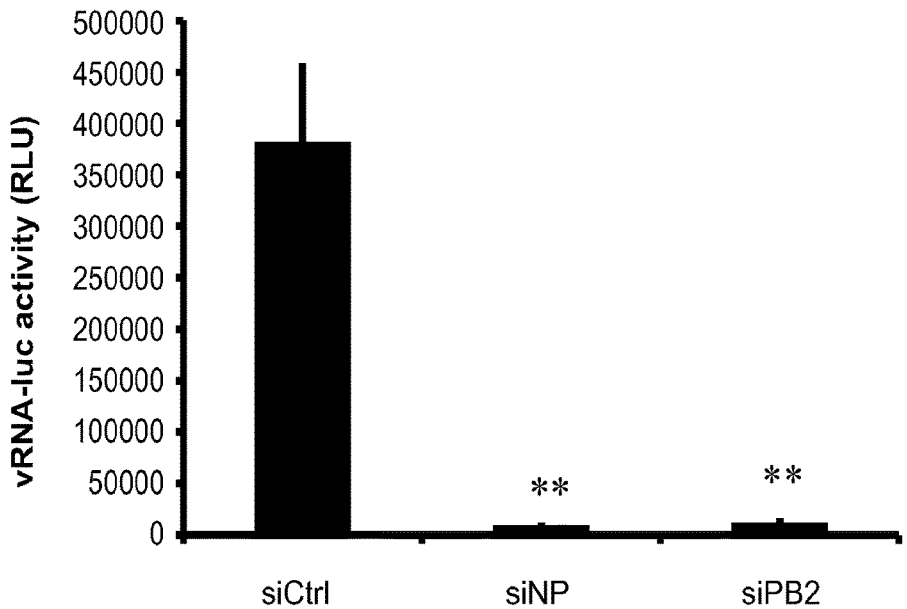
Figure 7B:
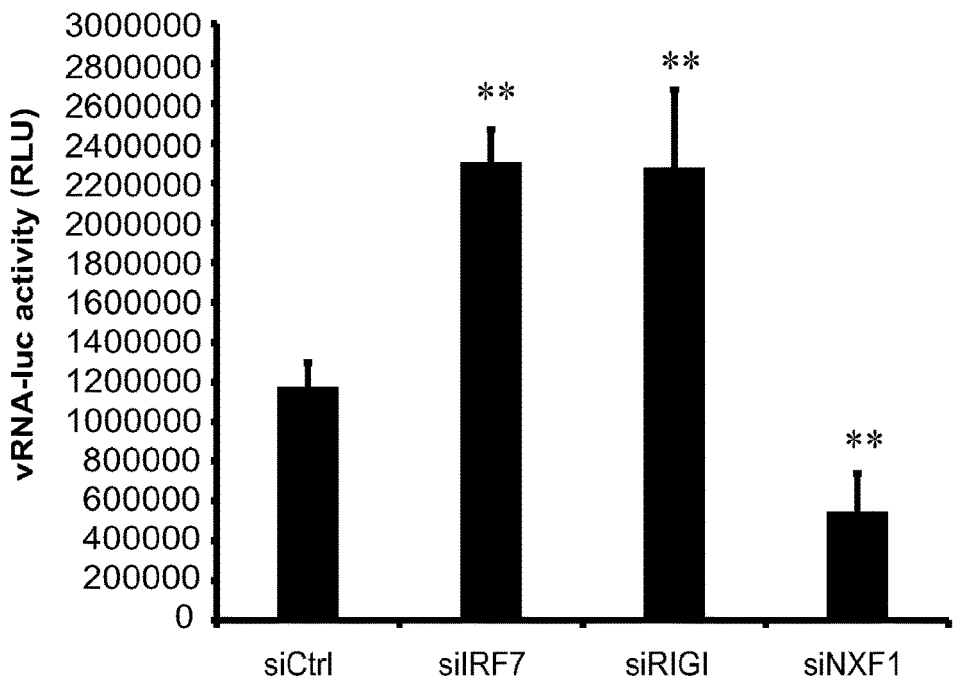

FIG. 7. The vRNA-luc reporter system allows high-throughput screening of influenza virus replication. Human bronchial epithelial cells (HBECs) were transfected with control siRNA or siRNA targeting the NP and PB2 genes of A/PR/8/34 influenza (A) or known cellular pro- and anti-viral factors (B). 72 hours later, cells were infected with A/PR8, and supernatants were harvested 48 hours post-infection. Supernatants were placed on 293Ts transfected 48 hours prior with the NP-vRNA-luc plasmid. Cells were lysed with SteadyGlo (Promega) 24 hours later and luciferase was measured using the Envision system.

Figure 8A:
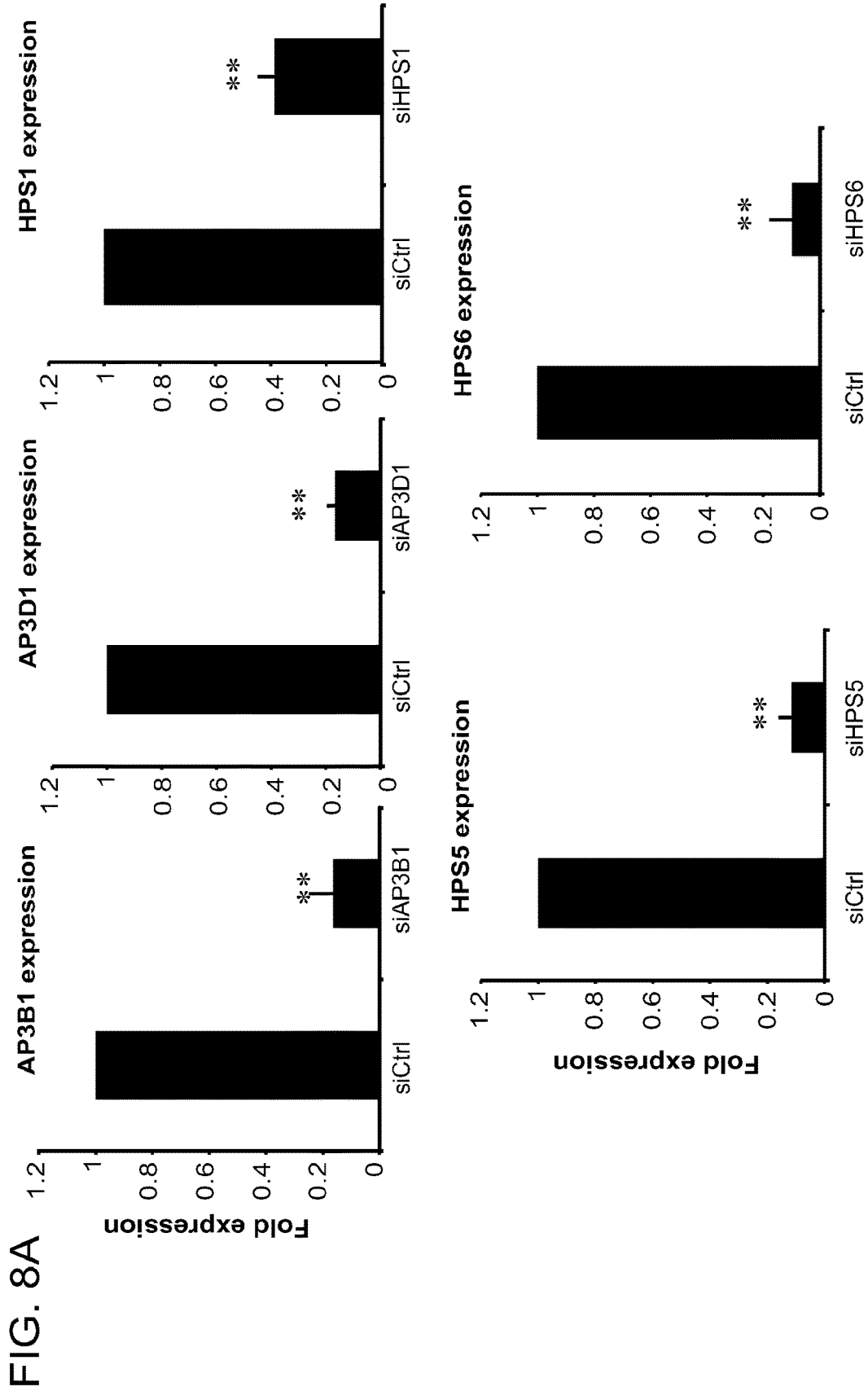
Figure 8B:
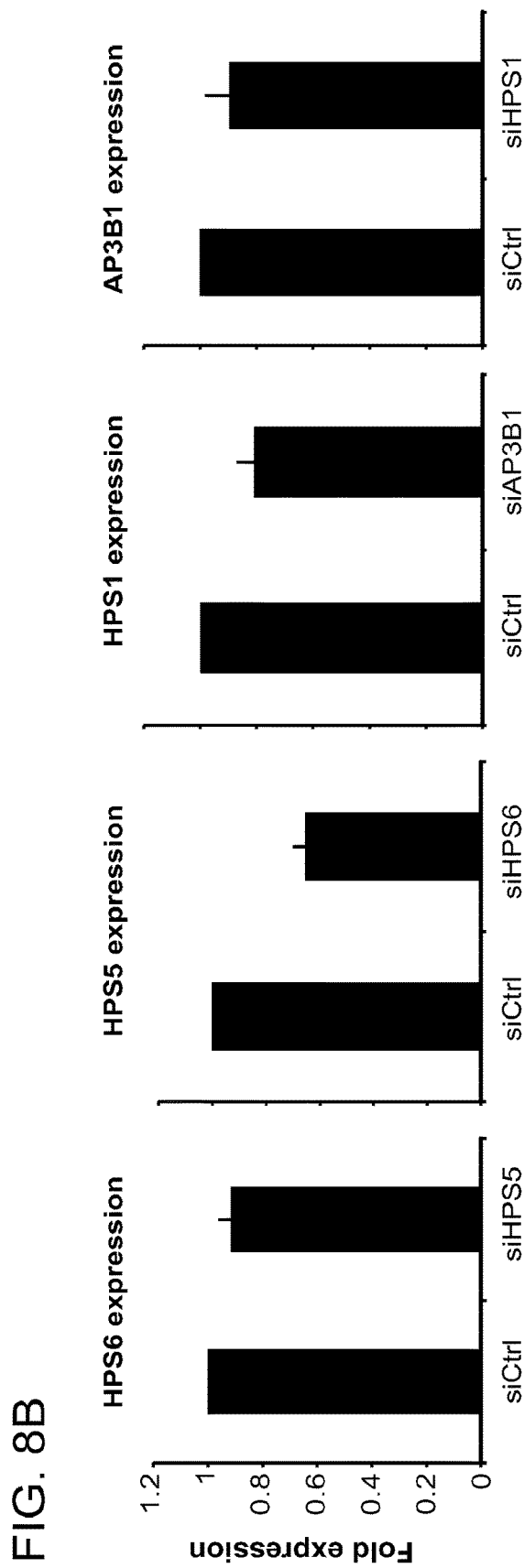
Figure 8C:
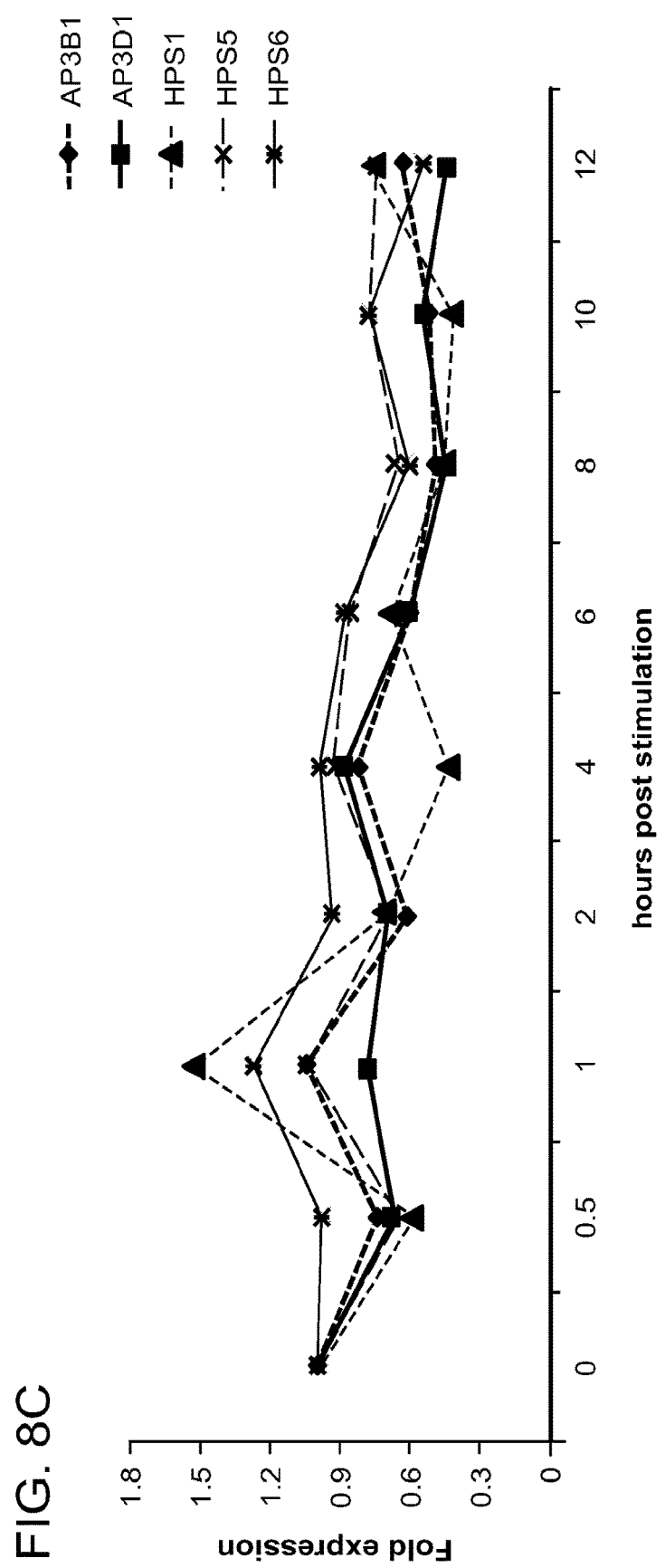

FIG. 8. Knockdown of Hermansky-Pudlak syndrome (HPS) associated proteins is specific in HBECs. (A) Knockdown efficiency was assessed by qPCR in HBECs treated with AllStar Negative Control siRNA or the Dharmacon siGENOME siRNA pool against the specified gene. (B) Expression levels of HPS-associated proteins is unaffected by treatment with siRNA of a related protein. Knockdown efficiency in HBECs was assessed by qPCR. (C) Expression levels of HPS-associated proteins were not changed upon stimulation with A/PR/8/34. HBECs were stimulated with PR8 for the indicated intervals of time, and cells were then lysed with TCL buffer. RNA was prepared using Qiagen TurboCapture, and cDNA was then produced. Expression of the indicated genes was determined using qPCR. Normalization was performed to the no stimulation timepoint, and b-actin was used as a housekeeping control.

Figure 9A:
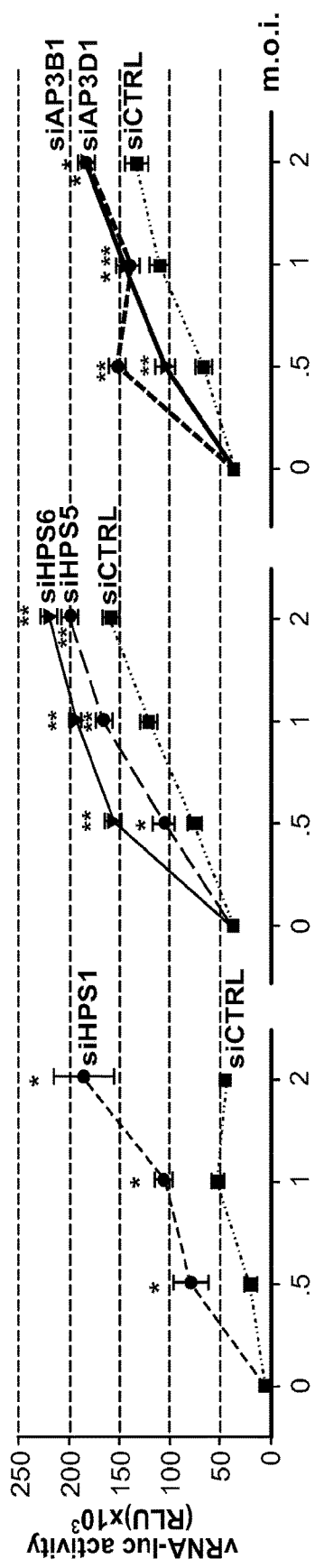
Figure 9B:
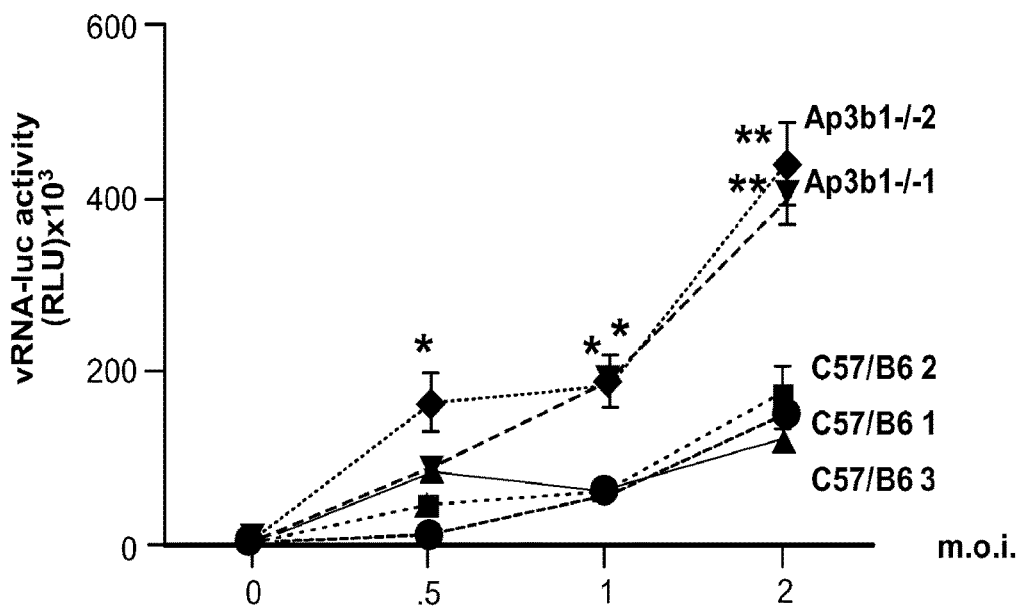
Figure 9C:
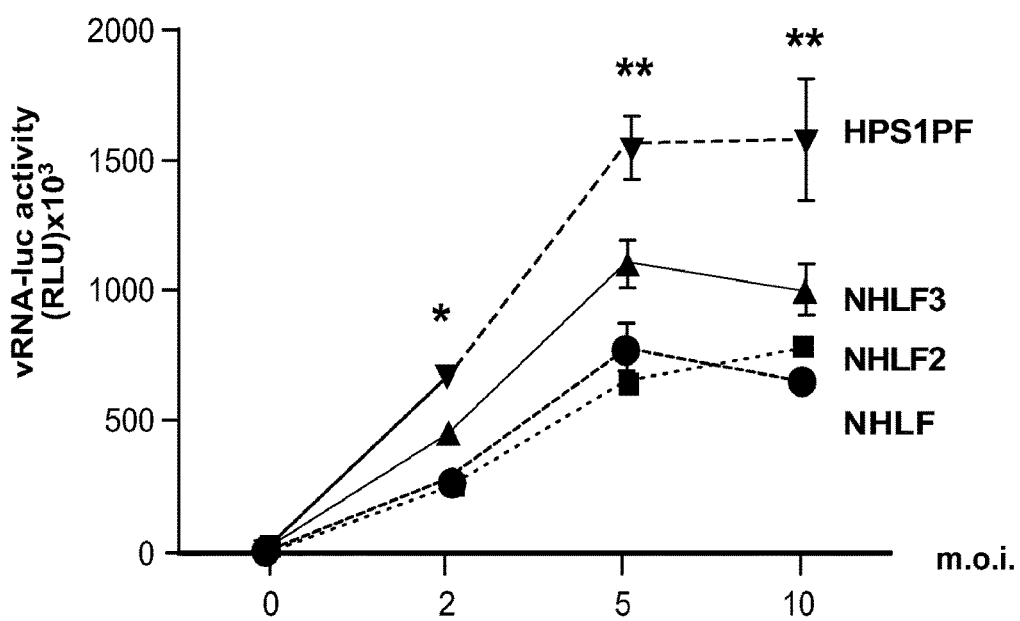

FIG. 9. (A) HBECs were transfected with the indicated siRNAs and then infected with PR8. Infection was allowed to proceed for 48 hours. Viral titer from supernatants was assessed using a vRNA reporter transfected into 293Ts. Values represent mean+/−SEM, n=5 throughout. (B) Primary mouse lung fibroblasts from C57BL/6 mice and Ap3b1−/− mice were infected with PR8 and supernatants were harvested 48 hours later. Supernatants were titered using the vRNA reporter. (C) NHLF cells from 3 normal patients and one HPS1 patient were infected with PR8, and supernatants were collected 48 hours later. Supernatants were titered using the vRNA reporter.

FIG. 10. (A) HPS1 expression levels in the human HPS1-mutant fibroblasts were assessed by qPCR. NHLF cells from 3 normal patients and one HPS1 patient were lysed with RLT buffer, and RNA and cDNA was made from these lysates. HPS1 levels were assessed by qPCR with gapdh used as a housekeeping control. (B) Overexpression of HPS1. HPS1 expression in NHLF cells leads to lower production of influenza. (C) Expression of a truncated HPS1 protein that cannot form the BLOC3 complex with HPS4 shows a dominant-negative phenotype in NHLF cells by qPCR (top panel) and vRNA reporter (bottom panel)

FIG. 11. SC35 restricts replication of RNA and DNA viruses. (A) Influenza A virus PR8 replication in SC35-KD HBE cells with or without IFNβ treatment assessed by PR8 surface HA immunostaining (upper panel, HA intensity; middle panel, frequency of HA positive cells) or by a vRNA luciferase reporter assay (lower panel). SC35 protein knockdown shown in the immunoblot. (B) Viral mRNAs quantified by qRT-PCR in SC35-KD HBE cells. (C and D) Viral protein levels (C) and titers (D) measured in SC35-overexpressed A549 cells. (E) NDV, VSV and MCMV replication in SC35-KD cells; left, GFP reporters for NDV, MCMV; right, luciferase reporter for VSV.

DETAILED DESCRIPTION OF THE INVENTION

The invention is based in part upon the surprising discovery of genes that are important for viral replication in a host cell. Studies were performed to identify factors or genes that inhibit or reduce viral replication in host cells. Specifically, in a first study, sixty genes were identified that significantly impacted viral replication. When silenced, thirty-six (36) of the genes led to an increase in viral replication and twenty-four (24) genes led to a decrease in viral replication. In a second study, one hundred (100) genes were identified whose knockdown resulted in increased viral replication.

Genes that Affect Viral Replication

The 36 and 100 genes that when silenced led to an increase in viral replication are listed in Tables 1a and 1b, and the 24 genes that when silenced led to a decrease in viral replication are listed in Table 2.

TABLE 1

| Gene Name | NCBI Gene ID |
|---|---|
| RUVBL2 | 10856 |
| SNX8 | 29886 |
| Rab35 | 11021 |
| Rab37 | 326624 |
| CHMP2a | 27243 |
| VAMP2 | 6844 |
| Oligophrenin 1 | 4983 |
| Complexin IV | 339302 |
| Drosha | 29102 |
| Hps5 | 11234 |
| UAP56 | 7919 |
| VPS18 | 57617 |
| SEC23IP | 11196 |
| VPS35 | 55737 |
| TM4SF6 | 7105 |
| Arf3 | 377 |
| ITSN1 | 6453 |
| PETA-3 | 977 |
| SNX21 | 90203 |
| NET5 | 10867 |
| Ap3d | 8943 |
| SYT9 | 143425 |
| VPS4b | 9525 |
| DEGS1 | 8560 |
| Arl5a | 26225 |
| SMARCE1 | 6605 |
| SAF-B | 6294 |
| Rab7 | 7879 |
| HPS1 | 3257 |
| Annexin A3 | 306 |
| PCDH15 | 387683 |
| VPS37b | 79720 |
| ap3b1 | 8546 |
| L6 | 4071 |
| Syntaxin11 | 8676 |
| RAD21 | 5885 |

TABLE 1b

| Gene Name | Gene ID | |
|---|---|---|
| APPBP1 | 8883 | V |
| CEBPB | 1051 | V |
| NFE2L2 | 4780 | V |
| NUP98 | 4928 | V |
| PDGFRL | 5157 | V |
| PPP1R1C | 151242 | V |
| SFRS2 | 6427 | V |
| SNAI2 | 6591 | V |
| TAF5L | 27097 | V |
| TJP2 | 9414 | V |
| TMEM14C | 51522 | V |
| ZNF331 | 55422 | V |
| ZNF498 | 221785 | V |
| A2M | 2 | |
| ADAM10 | 102 | |
| ADH1B | 124125126 | |
| ADH5 | 128642443 | |
| AK2 | 204 | |
| ALPK3 | 57538 | |
| ANUBL1 | 93550 | |
| ARSD | 414 | |
| B3GALT1 | 8708 | |
| BRDT | 643486676 | |
| CACNB1 | 782 | |
| CD96 | 10225 | |
| CDC14A | 8556 | |
| CDCA4 | 55038 | |
| CEBPA | 1050 | |
| CINP | 51550 | |
| CITED1 | 4435 | |
| CLCN4 | 1183 | |

TABLE 1b-continued

| Gene Name | Gene ID |
|---|---|
| COG2 | 22796 |
| CUL7 | 9820 |
| DGKD | 8527 |
| DHRS7 | 51635 |
| DMTF1 | 9988 |
| DUSP27 | 92235 |
| ETS1 | 2113 |
| EVX1 | 2128 |
| F11 | 2160 |
| FGFR1OP | 11116 |
| FLT1 | 2321 |
| GPRC5B | 51704 |
| H2AFZ | 3015 |
| HDAC10 | 83933 |
| HHEX | 3087 |
| HK1 | 3098 |
| HMGCR | 3156 |
| HTR2B | 3357 |
| IARS | 3376 |
| IL12B | 3593 |
| KIAA0226 | 9711 |
| MC2R | 4158 |
| MTMR6 | 9107 |
| MYCN | 4613 |
| NF2 | 4771 |
| NHLRC1 | 378884 |
| OBSCN | 84033 |
| OR10R2 | 343406 |
| PAK3 | 5063 |
| POU2AF1 | 5450 |
| PRTFDC1 | 56952 |
| RAB11FIP5 | 26056 |
| RABL3 | 285282 |
| RNF25 | 64320 |
| RPS6KA3 | 6197 |
| RXRG | 6258 |
| RYR3 | 6263 |
| SDHC | 6391 |
| SFRS6 | 6431644422 |
| SLC2A12 | 154091 |
| SQSTM1 | 8878 |
| SRPK2 | 6733 |
| STARD8 | 9754 |
| STAT5B | 6777 |
| STK4 | 6789 |
| THRA | 7067 |
| TIMP1 | 7076 |
| TLL1 | 7092 |
| TLR3 | 7098 |
| TMEM130 | 222865 |
| TREM1 | 54210 |
| UBE2E3 | 10477 |
| UST | 10090 |
| YEATS4 | 8089 |
| YY1 | 7528 |
| ZBTB25 | 7597 |
| ZIM2 | 100169890236 195000 |
| ZNF483 | 158399 |
| ZNF682 | 91120 |
| ZNFX1 | 57169 |

TABLE 2

| Gene name | NCBI GeneID |
|---|---|
| SH3GLB2 | 56904 |
| SYTL5 | 94122 |
| EPN1 | 29924 |
| ATP6V0A1 | 535 |
| Dbp5 | 11269 |
| Rab1b | 81876 |
| rRp41 | 54512 |
| NXF1 | 10482 |
| Crm1 | 7514 |

TABLE 2-continued

| Gene name | NCBI GeneID |
| --- | --- |
| sumo-1 | 7341 |
| SNX13 | 23161 |
| CLTA | 1211 |
| Fig | 57120 |
| Arl16 | 339231 |
| Tho2 | 57187 |
| Munc18-2 | 6813 |
| ARPC2 | 10109 |
| CAV1 | 857 |
| CLTB | 1212 |
| Snapin | 23557 |
| CHMP4c | 92421 |
| Munc18-3 | 6814 |
| SYT16 | 83851 |
| RAE1 | 8480 |

The present invention relates to disruption of one or more genes listed in Tables 1a or 1b (genes marked with 'V' have been validated with independent siRNAs), in a cell such that viral replication is increased. Preferably, the one or more genes are selected from the group consisting of HPS5, HPS1, AP3B1, AP3D, SC35, APPBP1, CEBPB, NFE2L2, NUP98, PDGFRL, PPP1R1c, SFRS2, SNAI2, TAF5L, TJP2, TMEM14C, ZNFF331 and ZNF498. The present invention further relates to the viruses obtainable by the process described and to vaccines that contain viruses of this type or constituents thereof. In addition to vaccine preparation, viruses obtained from the methods described also have significant use in virus surveillance, where the viruses produced can be sequenced by standard methods known in the art and identified.

The present invention further relates to disruption of one or more of the genes listed in Table 2 in a cell such that viral replication is reduced. In some aspects the cell is infected with a virus. These methods are useful in treating or alleviating a symptom of a disorder in which decreasing viral production is desirable. For example, chronic viral infections such as hepatitis B, hepatitis C, herpes, or HIV.

By increase in viral replication it is meant that the cells of the invention at produce least 1-fold, 2-fold, 3-fold, 4-fold 5-fold or more virus than cells in which do not have one or more of the genes listed in Table 1a or 1b disrupted. Alternatively, an increase in viral replication is meant that the cells of the invention produce at least 10%, 15%, 20%, 25%, 50%, 60%, 70%, 80%, 90% or 100% or more virus than cells in which do not have one or more of the genes listed in Table 1a or 1b disrupted.

Methods for Virus Replication

The present invention is thus based on the object of making available cells and processes that make possible simple and economical virus replication in cell culture. This object is achieved by the provision of the embodiments indicated in the patent claims.

The viruses produced from the processes and cell lines described herein can be used in viral vaccine preparations.

The viruses produced can also be used in epidemiological surveillance, wherein the viruses are sequenced, for example by PCR-based methods known in the art, for identification. The epidemiological information obtained from such surveillance methods are invaluable to efforts to monitor changes in antigenicity of influenza viruses; to guide the selection of strains for the annual influenza vaccine; and to provide virus samples for use in vaccine production.

The cells according to the invention comprise a disruption of one or more genes listed in Tables 1a or 1b, wherein the disruption results in decreased expression or activity of the one or more genes in the cell.

Disruption of one or more genes according to the present invention can be achieved by methods known in the art and described herein. For example, RNA silencing agents that target one or more genes in Tables 1a or 1b can be delivered to cells to decrease the expression or activity of the one or more genes in Tables 1a or 1b and increase viral replication. RNAi silencing agents are any compounds, small molecules, nucleotides or enzymes that disrupt, reduce or inhibit expression of a particular gene of interest. For example, RNAi silencing agents include any nucleotide sequence that inhibits or reduces expression of a gene, and including but not limited to siRNAs, shRNAs, morpholinos or aptamers. Preferred RNAi agents include siRNA and shRNA sequences that specifically target one or more genes in Table 1a or 1b. Particularly preferred shRNA sequences are listed in Table 3. Other siRNA or shRNA sequences targeting one or more genes of Tables 1a and 1b can be readily designed by the ordinarily skilled artisan, for example, by using readily available online design tools and programs.

Delivery of the RNAi silencing agent to the cells can be achieved by any means known to one skilled in the art, and include transfection, infection, electroporation and microinjection. SiRNA sequences may be delivered to the cell by transfection using liposomal delivery systems and transfection reagents (i.e., Hiperfect, Lipofectamine) known in the art. ShRNA sequences may be cloned into viral delivery vectors known in the art (i.e., retroviral or lentiviral vectors). The virus containing said shRNA sequences can be produced using methods known in the art, for example by transfecting the shRNA-containing viral delivery vector in combination with viral packaging constructs into a cell, and collecting the supernatant that contains the virus. Cells of the present invention are infected by the shRNA-containing virus and those cells containing the viral shRNA vector can be selected for by a selection marker present on the viral vector, such as GFP or an antibiotic selection.

Efficiency of knockdown of expression of the one or more target genes by any RNAi silencing agent can be determined through gene expression assays, for example, quantitative real-time PCR, microarray, immunoassay, or western blot.

In some aspects, a stable cell line with knockdown of the one or more target genes may be preferred. Stable cell lines can be produced by methods known in the art and disclosed herein. Particularly, cells infected with virus containing shRNAs, in which the shRNA has successfully integrated into the genome, can be selected for and clonally expanded to produce a stable cell line with knockdown of the one or more target gene. Mammalian cell lines with stable knockdown of the one or more target genes that increase viral replication are advantageous to the mammalian cell lines currently used for production of virus with low viral output.

In some aspects, transient disruption or knockdown of the one or more target genes is preferred. For example, for replicating virus for vaccines in embryonated eggs from hens, transient disruption of the one or more target genes may be preferred. Briefly, replicating virus for vaccine preparations in hen's embryos comprises the following steps: (i) fertilizing and incubating embryonated eggs for a first predetermined amount of time (i.e., 12 days); (ii) infecting the one or more fertilized eggs by introducing into the allantoic cavity of the fertilized eggs with the virus to be replicated (i.e., by injection); (iii) incubating the one or more infected fertilized eggs under temperature and humidity conditions that allow replication of the virus for a second predetermined amount of time (i.e. 2-3 days); and (iv)

harvesting the allantoic fluid containing the virus of the one or more incubated eggs (i.e. by aspiration). The eggs may be infected with one or more strains of virus. In some aspects, the eggs are infected with 1-3, or more than 3 viral strains. In some aspects, the process includes an additional step of purifying or isolating the virus produced which is optionally followed or preceded by a viral inactivation step using methods well known to those skilled in the art such as those described in FR 2201079 or in FR 1538322. The purification may be brief and may be limited to a step of concentrating the virus by centrifugation after having generally clarified the infected allantoic fluids. The purification or isolation may be supplemented with a zonal centrifugation step carried out for example by means of sucrose density gradients. Chromatographic methods may also be carried out in order to purify the virus. The inactivation of the viral suspension can be carried out by conventional means, using beta-propiolactone, ethyleneimine, formaldehyde or derivatives thereof.

SiRNAs targeting one or more target genes can be easily delivered to embryonated, or fertilized eggs through methods known in the art, for example, injection, electroporation or microinjection. The optimal time of siRNA delivery to the eggs for the purpose of replicating virus is such that the one or more targets genes are sufficiently downregulated to increase viral replication in the eggs, for example, the target genes are downregulated at the time of infection. The time of siRNA delivery can be determined by one of the skill in the art. In some embodiments, the siRNA is delivered to the embryonated eggs before injection of the virus to be replicated. Alternatively, the siRNA may be delivered simultaneously with the virus to be replicated to the embryonated eggs. In yet another alternative, the siRNA is delivered to the embryonated eggs after injection of the virus to be replicated.

The present invention further provides non-human transgenic knockout animals that do not express a functional protein of one ore more genes listed in Table 1a or 1b. These animals can be used to produce virus for the production of viral vaccines. For example, the non-human animal is a chicken. Alternatively, cells isolated or obtained from these animals can be used for the production of viral vaccines.

The cells according to the invention are preferably vertebrate cells, e.g. avian cells, in particular hens' embryo cells. In a particularly preferred embodiment, the cells according to the invention are mammalian cells, e.g. from hamsters, cattle, monkeys or dogs, in particular kidney cells or cell lines derived from these. They are preferably cells which are derived from MDCK cells (ATCC CCL34 MDCK (NBL-2)), and particularly preferably cells of the cell line MDCK 33016.

The cells according to the invention can be cultured in the course of the process in various serum-free media known to the person skilled in the art (e.g. Iscove's medium, ultra CHO medium (BioWhittaker), EX-CELL (JRH Biosciences)). Otherwise, the cells for replication can also be cultured in the customary serum-containing media (e.g. MEM or DMEM medium with 0.5% to 10%, preferably 1.5% to 5%, of fetal calf serum) or protein-free media (e.g. PF-CHO (JRH Biosciences)). Suitable culture vessels which can be employed in the course of the process according to the invention are all vessels known to the person skilled in the art, such as, for example, spinner bottles, roller bottles or fermenters.

The temperature for the proliferation of the cells before infection with viruses, such as influenza, is preferably 37° C. Culturing for proliferation of the cells is carried out in a preferred embodiment of the process in a perfusion system, e.g. in a stirred vessel fermenter, using cell retention systems known to the person skilled in the art, such as, for example, centrifugation, filtration, spin filters and the like.

The cells are in this case preferably proliferated for 2 to 18 days, particularly preferably for 3 to 11 days. Exchange of the medium is carried out in the course of this, increasing from 0 to approximately 1 to 3 fermenter volumes per day. The cells are proliferated up to very high cell densities in this manner, preferably up to approximately $2\times10^7$ cells/ml. The perfusion rates during culture in the perfusion system can be regulated both via the cell count, the content of glucose, glutamine or lactate in the medium and via other parameters known to the person skilled in the art. For infection with influenza viruses, about 85% to 99%, preferably 93 to 97%, of the fermenter volume is transferred with cells to a further fermenter. The cells remaining in the first fermenter can in turn be mixed with medium and replicated further in the perfusion system. In this manner, continuous cell culture for virus replication is available.

Alternatively to the perfusion system, the cells in the process according to the invention can preferably also be cultured in a batch process. The cells according to the invention proliferate here at 37° C.

In a preferred embodiment of the process according to the invention, the pH of the culture medium used to culture the cells is regulated during culturing and is in the range from pH 6.6 to pH 7.8, preferably in the range from pH 6.8 to pH 7.3.

Furthermore, the $pO_2$ value (partial pressure of oxygen) is advantageously regulated in this step of the process and is preferably between 25% and 95%, in particular between 35% and 60% (based on the air saturation).

In a further preferred embodiment, the infection of the cells with influenza viruses is carried out at an m.o.i. (multiplicity of infection) of about 0.0001 to 10, preferably of 0.002 to 0.5. The addition of the protease which brings about the cleavage of the precursor protein of hemagglutinin and thus the adsorption of the viruses on the cells, can be carried out according to the invention shortly before, simultaneously to or shortly after the infection of the cells with influenza viruses. If the addition is carried out simultaneously to the infection, the protease can either be added directly to the cell culture to be infected or, for example, as a concentrate together with the virus inoculate. The protease is preferably a serine protease, and particularly preferably trypsin.

In a preferred embodiment, trypsin is added to the cell culture to be infected up to a final concentration of 1 to 200 μg/ml, preferably 5 to 50 μg/ml, and particularly preferably 5 to 30 μg/ml in the culture medium. During the further culturing of the infected cells according to the process according to the invention, trypsin reactivation can be carried out by fresh addition of trypsin in the case of the batch process or in the case of the perfusion system by continuous addition of a trypsin solution or by intermittent addition.

After infection, the infected cell culture is cultured further to replicate the viruses, in particular until a maximum cytopathic effect or a maximum amount of virus antigen can be detected. Preferably, the culturing of the cells is carried out for 2 to 10 days, in particular for 3 to 7 days. The culturing can in turn preferably be carried out in the perfusion system or in the batch process.

In a further preferred embodiment, the cells are cultured at a temperature of 30° C. to 36° C., preferably of 32° C. to 34° C. after infection with influenza viruses. The culturing of the infected cells at temperatures below 37° C. in particular in the temperature ranges indicated above, leads to the production of influenza viruses which after inactivation have an appreciably higher activity as vaccine, in comparison with influenza viruses which have been replicated at 37° C. in cell culture.

The culturing of the cells after infection with influenza viruses is in turn preferably carried out at regulated pH and $pO_2$. The pH in this case is preferably in the range from 6.6 to 7.8, particularly preferably from 6.8 to 7.2, and the $pO_2$ in the range from 25% to 150%, preferably from 30% to 75%, and particularly preferably in the range from 35% to 60% (based on the air saturation).

During the culturing of the cells or virus replication according to the process, a substitution of the cell culture medium with freshly prepared medium, medium concentrate or with defined constituents such as amino acids, vitamins, lipid fractions, phosphates etc. for optimizing the antigen yield is also possible.

After infection with influenza viruses, the cells can either be slowly diluted by further addition of medium or medium concentrate over several days or can be incubated during further perfusion with medium or medium concentrate decreasing from approximately 1 to 3 to 10 fermenter volumes/day. The perfusion rates can in this case in turn be regulated by means of the cell count, the content of glucose, glutamine, lactate or lactate dehydrogenase in the medium or other parameters known to the person skilled in the art.

A combination of the perfusion system with a fed-batch process is further possible. In a preferred embodiment of the process, the harvesting and isolation of the replicated influenza viruses is carried out 2 to 10 days, preferably 3 to 7 days, after infection. To do this, for example, the cells or cell residues are separated from the culture medium by means of methods known to the person skilled in the art, for example by separators or filters. Following this the concentration of the influenza viruses present in the culture medium is carried out by methods known to the person skilled in the art, such as, for example, gradient centrifugation, filtration, precipitation and the like.

The present invention also provides a process for replicating virus in cells infecting the cell with a virus and a compound that inhibits the expression or activity of one or more genes listed in Tables 1a or 1b; and incubating the cell for a predetermined period of time to allow replication of the virus. The process further comprises isolating the replicated virus. The virus can then be used for vaccine preparation or for viral surveillance. Exemplary cells of the present invention are vertebrate or mammalians cells. For example, the mammalian cells are from a human, hamster, cattle, monkey, dog or human. In some instances, the cells may be from a tissue of an infected animal. The compound that inhibits the expression or activity of the one or more genes listed in Tables 1a or 1b can be an RNA silencing agent, such as a nucleic acid. Preferred RNA silencing agents are siRNAs or short hairpin RNAs that target one or more genes listed in Tables 1a or 1b.

Viral Vaccines

The present invention also relates to a method of making a vaccine comprising formulating the virus replicated in any of the present invention into a vaccine. The virus is an influenza virus, an Ebola virus, or a Marburg virus. In some embodiments, the influenza virus is more than one strain of influenza virus. In other embodiments, the virus is Newcastle disease virus, vesicular stomatitis virus, a DNA virus, or mouse cytomegalovirus.

The invention further relates to viruses which are obtainable by a process according to the invention. These can be formulated by known methods to give a vaccine for administration to humans or animals. The immunogenicity or efficacy of the influenza viruses obtained as vaccine can be determined by methods known to the person skilled in the art, e.g. by means of the protection imparted in the loading experiment or as antibody titers of neutralizing antibodies. The determination of the amount of virus or antigen produced can be carried out, for example, by the determination of the amount of hemagglutinin according to methods known to the person skilled in the art. It is known, for example, that cleaved hemagglutinin binds to erythrocytes of various species, e.g. to hens' erythrocytes. This makes possible a simple and rapid quantification of the viruses produced or of the antigen formed.

Thus the invention also relates to vaccines which contain viruses obtainable from the process according to the invention. Vaccines of this type can optionally contain the additives customary for vaccines, in particular substances which increase the immune response, i.e. so-called adjuvants, e.g. hydroxide of various metals, constituents of bacterial cell walls, oils or saponins, and moreover customary pharmaceutically tolerable excipients.

The viruses can be present in the vaccines as intact virus particles, in particular as live attenuated viruses. For this purpose, virus concentrates are adjusted to the desired titer and either lyophilized or stabilized in liquid form.

In a further embodiment, the vaccines according to the invention can contain disintegrated, i.e. inactivated, or intact, but inactivated viruses. For this purpose, the infectiousness of the viruses is destroyed by means of chemical and/or physical methods (e.g. by detergents or formaldehyde). The vaccine is then adjusted to the desired amount of antigen and after possible admixture of adjuvants or after possible vaccine formulation, dispensed, for example, as liposomes, microspheres or "slow release" formulations.

In a further preferred embodiment, the vaccines according to the invention can finally be present as subunit vaccine, i.e. they can contain defined, isolated virus constituents, preferably isolated proteins of the influenza virus. These constituents can be isolated from the influenza viruses by methods known to the person skilled in the art.

Furthermore, the viruses obtained by the process according to the invention can be used for diagnostic purposes. Thus the present invention also relates to diagnostic compositions which contain influenza viruses according to the invention or constituents of such viruses, if appropriate in combination with additives customary in this field and suitable detection agents.

DEFINITIONS

As used herein, the terms "cell" "cell line" "strain," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included. Where distinct designations are intended, it will be clear from the context The term "host cell" means a cell that contains a heterologous nucleic acid, such as a vector, and supports the replication and/or expression of the nucleic acid. Host cells can be prokaryotic cells such as *E. coli*, or eukaryotic cells such as yeast, insect, amphibian, avian or mammalian cells, including human cells. Exemplary host cells in the context of the invention include Vero (African green monkey kidney) cells, BHK (baby hamster kidney) cells, primary chick kidney (PCK) cells, Madin-Darby Canine Kidney (MDCK) cells, Madin-Darby Bovine Kidney (MDBK) cells, 293 cells (e.g., 293T cells), and COS cells (e.g., COS1, COS7 cells).

The term "disruption" as used herein in the context of gene or genetic construct encoding a polypeptide means any action at the nucleic acid level that results in; a) a decrease in activity of an encoded polypeptide; b) elimination of the encoded polypeptide activity, c) transcription of an incomplete polypeptide sequence; d) incorrect folding of an encoded polypeptide; e) interference with the encoded RNA transcript, or any other activity resulting in a down-regulation of the gene. A gene may be disrupted for example by insertion of a foreign set of base pairs in a coding region, deletion of any portion of the gene, or by the presence of antisense sequences that interfere with transcription or translation of the gene. Disrupted genes are down-regulated. As used herein, the term "down-regulated" refers to a gene that has been mutated, altered, and/or disrupted such that the expression of the gene is less than that associated with the native gene sequence. In another aspect, the term down-regulated may include any mutation that decreases or eliminates the activity of the enzyme encoded by the mutant gene. In another embodiment, down-regulated includes elimination of the gene's expression (i.e. gene knockout). As used herein, the symbol "Δ" will be used to denote a mutation in the specified coding sequence and/or promoter wherein at least a portion (up to and including all) of said coding sequence and/or promoter has been disrupted by a deletion, mutation, or insertion. In another embodiment, the disruption can occur by optionally inserting a nucleic acid molecule into the native sequence whereby the expression of the mutated gene is down-regulated (either partially or completely). In yet another embodiment, down-regulation of expression can occur by down-regulating, altering, or disruption expression of one or more transcription factors influencing expression of the gene. At least 70%, 80%, 85%, 90%, 95%, 96%, 97% 98%, 99% or 100% of the genes expression is silenced.

The terms "nucleic acid," "polynucleotide," "polynucleotide sequence" and "nucleic acid sequence" refer to single-stranded or double-stranded deoxyribonucleotide or ribonucleotide polymers, or chimeras or analogues thereof. As used herein, the term optionally includes polymers of analogs of naturally occurring nucleotides having the essential nature of natural nucleotides in that they hybridize to single-stranded nucleic acids in a manner similar to naturally occurring nucleotides (e.g., peptide nucleic acids). Unless otherwise indicated, a particular nucleic acid sequence optionally encompasses complementary sequences, in addition to the sequence explicitly indicated.

The term "gene" is used broadly to refer to any nucleic acid associated with a biological function. Thus, genes include coding sequences and/or the regulatory sequences required for their expression. The term "gene" applies to a specific genomic sequence, as well as to a cDNA or an mRNA encoded by that genomic sequence.

Genes also include non-expressed nucleic acid segments that, for example, form recognition sequences for other proteins. Non-expressed regulatory sequences include "promoters" and "enhancers," to which regulatory proteins such as transcription factors bind, resulting in transcription of adjacent or nearby sequences. A "tissue specific" promoter or enhancer is one that regulates transcription in a specific tissue type or cell type or types.

The term "vector" refers to the means by which a nucleic acid can be propagated and/or transferred between organisms, cells, or cellular components. Vectors include plasmids, viruses, bacteriophage, pro-viruses, phagemids, transposons, and artificial chromosomes, and the like, that replicate autonomously or can integrate into a chromosome of a host cell. A vector can also be a naked RNA polynucleotide, a naked DNA polynucleotide, a polynucleotide composed of both DNA and RNA within the same strand, a poly-lysine-conjugated DNA or RNA, a peptide-conjugated DNA or RNA, a liposome-conjugated DNA, or the like, that are not autonomously replicating.

An "expression vector" is a vector, such as a plasmid, that is capable of promoting expression of, as well as replication of, a nucleic acid incorporated therein. Typically, the nucleic acid to be expressed is "operably linked" to a promoter and/or enhancer, and is subject to transcription regulatory control by the promoter and/or enhancer.

A "bi-directional expression vector" is characterized by two alternative promoters oriented in the opposite direction relative to a nucleic acid situated between the two promoters, such that expression can be initiated in both orientations resulting in, e.g., transcription of both plus (+) or sense strand, and negative (−) or antisense strand RNAs.

In the context herein, the term "isolated" refers to a biological material, such as a nucleic acid or a protein, which is substantially free from components that normally accompany or interact with it in its naturally occurring environment. The isolated material optionally comprises material not found with the material in its natural environment, e.g., a cell. For example, if the material is in its natural environment, such as a cell, the material has been placed at a location in the cell (e.g., genome or genetic element) not native to a material found in that environment. For example, a naturally occurring nucleic acid (e.g., a coding sequence, a promoter, an enhancer, etc.) becomes isolated if it is introduced by non-naturally occurring means to a locus of the genome (e.g., a vector, such as a plasmid or virus vector, or amplicon) not native to that nucleic acid. Such nucleic acids are also referred to as "heterologous" nucleic acids.

The term "recombinant" indicates that the material (e.g., a nucleic acid or protein) has been artificially or synthetically (non-naturally) altered. The alteration can be performed on the material within or removed from, its natural environment or state. Specifically, when referring to a virus, e.g., an influenza virus is recombinant when it is produced by the expression of a recombinant nucleic acid.

The term "reassortant," when referring to a virus, indicates that the virus includes genetic and/or polypeptide components derived from more than one parental viral strain or source. For example, a 7:1 reassortant includes 7 viral genomic segments (or gene segments) derived from a first parental virus, and a single complementary viral genomic segment, e.g., encoding hemagglutinin or neuraminidase, from a second parental virus. A 6:2 reassortant includes 6 genomic segments, most commonly the 6 internal genes from a first parental virus, and two complementary segments, e.g., hemagglutinin and neuraminidase, from a different parental virus.

The term "introduced" when referring to a heterologous or isolated nucleic acid refers to the incorporation of a nucleic acid into a eukaryotic or prokaryotic cell where the nucleic acid can be incorporated into the genome of the cell (e.g., chromosome, plasmid, plastid or mitochondrial DNA), converted into an autonomous replicon, or transiently expressed (e.g., transfected mRNA). The term includes such methods as "infection," "transfection," "transformation,"

and "transduction." In the context of the invention, a variety of methods can be employed to introduce nucleic acids into prokaryotic cells, including electroporation, calcium phosphate precipitation, lipid mediated transfection (lipofection), etc.

The terms "operably associated" or "operably linked," as used herein, refer to functionally coupled nucleic acid sequences.

"Decreased activity" "Reduced activity" or "inactivation" is defined herein to be at least a 75% reduction in protein activity, as compared with an appropriate control species. Preferably, at least 80, 85, 90, 95% reduction in activity is attained, and in the most preferred embodiment, the activity is eliminated (100%). Proteins can be inactivated with inhibitors, by mutation, or by suppression of expression or translation, and the like.

"Overexpression" or "overexpressed" is defined herein to be at least 150% of protein activity as compared with an appropriate control species. Overexpression can be achieved by mutating the protein to produce a more active form or a form that is resistant to inhibition, by removing inhibitors, or adding activators, and the like. Overexpression can also be achieved by removing repressors, adding multiple copies of the gene to the cell, or upregulating the endogenous gene, and the like As used herein "recombinant" is relating to, derived from, or containing genetically engineered material.

The term "RNA interference" or "RNAi" (also referred to in the art as "gene silencing" and/or "target silencing", e.g., "target mRNA silencing"), as used herein, refers generally to a sequence-specific or selective process by which a target molecule (e.g., a target gene, protein or RNA) is downregulated. In specific embodiments, the process of "RNA interference" or "RNAi" features degradation or post-transcriptional silencing of RNA molecules, e.g., RNA molecules within a cell, said degradation or silencing being triggered by an RNAi agent. Degradation and post-transcriptional silencing of target RNA is catalyzed by an enzymatic, RNA-induced silencing complex (RISC). RNAi occurs in cells naturally to remove foreign RNAs (e.g., viral RNAs). Natural RNAi proceeds via fragments cleaved from free dsRNA which direct the degradative mechanism to other similar RNA sequences. Alternatively, RNAi can be initiated by the hand of man, for example, to silence the expression of target genes.

The term "RNA silencing agent", as used herein, refers to an RNA (or analog thereof), having sufficient sequence complementarity to a target RNA (i.e., the RNA being degraded) to direct RNA silencing (e.g., RNAi). An RNA silencing agent having a "sequence sufficiently complementary to a target RNA sequence to direct RNA silencing" means that the RNA silencing agent has a sequence sufficient to trigger the destruction or post-transcriptional silencing of the target RNA by the RNA silencing machinery (e.g., the RISC) or process. An RNA silencing agent having a "sequence sufficiently complementary to a target RNA sequence to direct RNA silencing" is also intended to mean that the RNA silencing agent has a sequence sufficient to trigger the translational inhibition of the target RNA by the RNA silencing machinery or process. An RNA silencing agent having a "sequence sufficiently complementary to a target RNA encoded by the target DNA sequence such that the target DNA sequence is chromatically silenced" means that the RNA silencing agent has a sequence sufficient to induce transcriptional gene silencing, e.g., to down-modulate gene expression at or near the target DNA sequence, e.g., by inducing chromatin structural changes at or near the target DNA sequence.

An "RNA silencing inhibitory agent", as used herein, refers to any agent that is capable of interfering with the RNA silencing process. Such inhibitors might include, e.g., inhibitors of RISC assembly, inhibitors of siRNA or miRNA processing, 2'-O-methyl-oligonucleotides that are complementary to certain siRNA guide strands or miRNAs, small molecules and/or chemical compounds that interfere with RNA silencing, etc.

As used herein, the term "small interfering RNA" ("siRNA") (also referred to in the art as "short interfering RNAs") refers to an RNA (or RNA analog) comprising between about 10-50 nucleotides (or nucleotide analogs) which is capable of directing or mediating RNA interference.

As used herein, the term "microRNA" ("miRNA") refers to an RNA (or RNA analog) comprising the product of an endogenous, non-coding gene whose precursor RNA transcripts can form small stem-loops from which mature miRNAs are cleaved by Dicer (Lagos-Quintana et al., 2001; Lau et al., 2001; Lee and Ambros, 2001; Lagos-Quintana et al., 2002; Mourelatos et al., 2002; Reinhart et al., 2002; Ambros et al., 2003; Brennecke et al., 2003b; Lagos-Quintana et al., 2003; Lim et al., 2003a; Lim et al., 2003b). miRNAs are encoded in genes distinct from the mRNAs whose expression they control. Mature miRNAs represent the single stranded product of Dicer cleavage that then function as guide RNA fragments in mediating RNA silencing when incorporated into RISC.

The term "RNA" or "RNA molecule" or "ribonucleic acid molecule" refers to a polymer of ribonucleotides. The term "DNA" or "DNA molecule" or deoxyribonucleic acid molecule" refers to a polymer of deoxyribonucleotides. DNA and RNA can be synthesized naturally (e.g., by DNA replication or transcription of DNA, respectively). RNA can be post-transcriptionally modified. DNA and RNA can also be chemically synthesized. DNA and RNA can be single-stranded (i.e., ssRNA and ssDNA, respectively) or multi-stranded (e.g., double stranded, i.e., dsRNA and dsDNA, respectively). "mRNA" or "messenger RNA" is single-stranded RNA that specifies the amino acid sequence of one or more polypeptide chains. This information is translated during protein synthesis when ribosomes bind to the mRNA.

As used herein the term "transgenic animal" is meant to broadly describe an animal that has been manipulated to have altered activity of one or more specific gene/allele product(s) relative to the corresponding wild type animal. In some aspect, the animal has less or reduced activity of one or more specific gene/allele product(s) relative to the corresponding wild type animal. In another aspect, the animal has more or increased activity of one or more specific gene/allele product relative to the corresponding wild type animal. Preferably, the transgenic animal has been manipulated to be irreversibly missing all or "essentially all" of an activity of one or more specific gene/allele product(s) relative to the corresponding wild type animal, often referred to in the art as a "knockout animal". In a particular embodiment of this type, the transgenic animal contains within its genome a specific gene/allele that has been inactivated by a method such as gene targeting. Methods for making such a transgenic animal are well known in the art.

As used herein the term "transgenic animal" can therefore include the heterozygote animal (e.g., one defective allele and one wild-type allele), a homozygous animal (e.g., two defective alleles) or an animal having more than one gene having at least allele that has been inactivated.

A transgenic animal that is heterozygous for a particular gene product activity has been manipulated to be missing all or "essentially all" of the activity of at least one of the particular allele products relative to the corresponding wild type animal.

As used herein a transgenic animal or cell missing "essentially all" of an activity of a specific gene/allele product, is an animal or cell that has less than about 25% of the gene/allele product activity of the corresponding wild type animal or wild type cell. In a preferred embodiment the animal or cell has less than or equal to about 20% of the gene/allele product activity of the corresponding wild type animal or wild type cell respectively.

Vaccine Compositions

The present invention is directed to an immunogenic composition, e.g., a vaccine composition capable of raising a specific immune response. The vaccine composition comprises viruses produced by the methods described herein.

The vaccine composition can further comprise an adjuvant and/or a carrier. Examples of useful adjuvants and carriers are given herein below. The peptides and/or polypeptides in the composition can be associated with a carrier such as e.g. a protein or an antigen-presenting cell such as e.g. a dendritic cell (DC) capable of presenting the peptide to a T-cell.

Adjuvants are any substance whose admixture into the vaccine composition increases or otherwise modifies the immune response to the mutant peptide. Carriers are scaffold structures, for example a polypeptide or a polysaccharide, to which the neoantigenic peptides, is capable of being associated. Optionally, adjuvants are conjugated covalently or non-covalently to the peptides or polypeptides of the invention.

The ability of an adjuvant to increase the immune response to an antigen is typically manifested by a significant increase in immune-mediated reaction, or reduction in disease symptoms. For example, an increase in humoral immunity is typically manifested by a significant increase in the titer of antibodies raised to the antigen, and an increase in T-cell activity is typically manifested in increased cell proliferation, or cellular cytotoxicity, or cytokine secretion. An adjuvant may also alter an immune response, for example, by changing a primarily humoral or Th response into a primarily cellular, or Th response.

Suitable adjuvants include, but are not limited to 1018 ISS, aluminium salts, Amplivax, AS15, BCG, CP-870,893, CpG7909, CyaA, dSLIM, GM-CSF, IC30, IC31, Imiquimod, ImuFact IMP321, IS Patch, ISS, ISCOMATRIX, JuvImmune, LipoVac, MF59, monophosphoryl lipid A, Montanide IMS 1312, Montanide ISA 206, Montanide ISA 50V, Montanide ISA-51, OK-432, OM-174, OM-197-MP-EC, ONTAK, PepTel® vector system, PLG microparticles, resiquimod, SRL172, Virosomes and other Virus-like particles, YF-17D, VEGF trap, R848, beta-glucan, Pam3Cys, Aquila's QS21 stimulon (Aquila Biotech, Worcester, Mass., USA) which is derived from saponin, mycobacterial extracts and synthetic bacterial cell wall mimics, and other proprietary adjuvants such as Ribi's Detox. Quil or Superfos. Adjuvants such as incomplete Freund's or GM-CSF are preferred. Several immunological adjuvants (e.g., MF59) specific for dendritic cells and their preparation have been described previously (Dupuis M, et al., Cell Immunol. 1998; 186(1):18-27; Allison A C; Dev Biol Stand. 1998; 92:3-11). Also cytokines may be used. Several cytokines have been directly linked to influencing dendritic cell migration to lymphoid tissues (e.g., TNF-alpha), accelerating the maturation of dendritic cells into efficient antigen-presenting cells for T-lymphocytes (e.g., GM-CSF, IL-1 and IL-4) (U.S. Pat. No. 5,849,589, specifically incorporated herein by reference in its entirety) and acting as immunoadjuvants (e.g., IL-12) (Gabrilovich D I, et al., J Immunother Emphasis Tumor Immunol. 1996 (6):414-418).

CpG immunostimulatory oligonucleotides have also been reported to enhance the effects of adjuvants in a vaccine setting. Without being bound by theory, CpG oligonucleotides act by activating the innate (non-adaptive) immune system via Toll-like receptors (TLR), mainly TLR9. CpG triggered TLR9 activation enhances antigen-specific humoral and cellular responses to a wide variety of antigens, including peptide or protein antigens, live or killed viruses, dendritic cell vaccines, autologous cellular vaccines and polysaccharide conjugates in both prophylactic and therapeutic vaccines. More importantly, it enhances dendritic cell maturation and differentiation, resulting in enhanced activation of TH1 cells and strong cytotoxic T-lymphocyte (CTL) generation, even in the absence of CD4 T-cell help. The TH1 bias induced by TLR9 stimulation is maintained even in the presence of vaccine adjuvants such as alum or incomplete Freund's adjuvant (IFA) that normally promote a TH2 bias. CpG oligonucleotides show even greater adjuvant activity when formulated or co-administered with other adjuvants or in formulations such as microparticles, nano particles, lipid emulsions or similar formulations, which are especially necessary for inducing a strong response when the antigen is relatively weak. They also accelerate the immune response and enabled the antigen doses to be reduced by approximately two orders of magnitude, with comparable antibody responses to the full-dose vaccine without CpG in some experiments (Arthur M. Krieg, Nature Reviews, Drug Discovery, 5, Jun. 2006, 471-484). U.S. Pat. No. 6,406,705 B1 describes the combined use of CpG oligonucleotides, non-nucleic acid adjuvants and an antigen to induce an antigen-specific immune response. A commercially available CpG TLR9 antagonist is dSLIM (double Stem Loop Immunomodulator) by Mologen (Berlin, GERMANY), which is a preferred component of the pharmaceutical composition of the present invention. Other TLR binding molecules such as RNA binding TLR 7, TLR 8 and/or TLR 9 may also be used.

Other examples of useful adjuvants include, but are not limited to, chemically modified CpGs (e.g. CpR, Idera), Poly(I:C) (e.g. polyi:CI2U), non-CpG bacterial DNA or RNA as well as immunoactive small molecules and antibodies such as cyclophosphamide, sunitinib, bevacizumab, celebrex, NCX-4016, sildenafil, tadalafil, vardenafil, sorafinib, XL-999, CP-547632, pazopanib, ZD2171, AZD2171, ipilimumab, tremelimumab, and SC58175, which may act therapeutically and/or as an adjuvant. The amounts and concentrations of adjuvants and additives useful in the context of the present invention can readily be determined by the skilled artisan without undue experimentation. Additional adjuvants include colony-stimulating factors, such as Granulocyte Macrophage Colony Stimulating Factor (GM-CSF, sargramostim).

A vaccine composition according to the present invention may comprise more than one different adjuvants. Furthermore, the invention encompasses a therapeutic composition comprising any adjuvant substance including any of the above or combinations thereof. It is also contemplated that the peptide or polypeptide, and the adjuvant can be administered separately in any appropriate sequence.

A carrier may be present independently of an adjuvant. The function of a carrier can for example be to increase the molecular weight of in particular mutant in order to increase their activity or immunogenicity, to confer stability, to increase the biological activity, or to increase serum half-life. Furthermore, a carrier may aid presenting peptides to T-cells. The carrier may be any suitable carrier known to the person skilled in the art, for example a protein or an antigen presenting cell. A carrier protein could be but is not limited to keyhole limpet hemocyanin, serum proteins such as transferrin, bovine serum albumin, human serum albumin, thyroglobulin or ovalbumin, immunoglobulins, or hormones, such as insulin or palmitic acid. For immunization of humans, the carrier must be a physiologically acceptable carrier acceptable to humans and safe. However, tetanus toxoid and/or diphtheria toxoid are suitable carriers in one embodiment of the invention. Alternatively, the carrier may be dextrans for example sepharose.

EXAMPLES

Example 1: General Methods

Human Primary Cell Cultures and Virus Strains

Primary human bronchial epithelial cells (HBEC; Lonza, Basel, Switzerland) derived from normal human bronchial epithelium, were maintained in vented T225 tissue culture flasks and grown in bronchial epithelial cell basal medium (Lonza) containing hrEGF (25 ng/ml), bovine pituitary extract (65 ng/ml), 50 nM all trans-retinoic acid, BSA (1.5 µg/ml), nystatin (20 IU/ml; GIBCO), hydrocortisone (0.5 µg/ml), insulin (5 µg/ml), transferrin (10 µg/ml), epinephrine (0.5 µg/ml), triiodothyronine (6.5 ng/ml), gentamicin (50 µg/ml), and 50 µg/ml amphotericin-B (Cambrex). All experiments were performed with low passage (P) cells (P2-P6). Primary normal human lung fibroblasts (NHLF, Lonza, Basel, Switzerland) and primary HPS1 patient lung fibroblasts (a gift from Bernadette Gochuico) were maintained in vented tissue culture flasks and grown in mesenchymal stem cell growth medium (MSCGM, Lonza). All experiments were performed with P3-P6 cells. Both PR8 and dNS1 viral strains were grown in Vero cells (which allow efficient growth of the dNS1 virus) in serum-free DMEM with 10% BSA and 1 mg/ml TPCK trypsin. Viral titers were determined by standard MDCK plaque assays.

Cell Experiments for Transcriptional Profiling

To monitor transcriptional responses to relevant ligands, primary human bronchial epithelial cells (HBECs) or normal human lung fibroblasts (NHLFs) were either treated with IFNβ (500 U/ml) transfected (using LTX transfection reagent as per manufacturers protocol; Invitrogen; Carlsbad, Calif.) with vRNA (100 ng/ml), or infected with wildtype H1N1 influenza (PR8) or with NS1 deleted virus (in a PR8 parental strain, ΔNS1). Mock-treated cells were used as controls for stimulated cells. Virus infection was performed at a multiplicity of infection (MOI) of 1. Cells were lysed either with RLT (Qiagen) or TCL (Qiagen) lysis buffer for use in RNAeasy columns or Turbocapture plates, respectively, at 4, 6, or 8 hours post-treatment.

mRNA Isolation

Total RNA was extracted with RLT reagent following the RNeasy kit's procedure (Qiagen, Valencia, Calif.). RNA was reverse transcribed with the High Capacity cDNA Reverse Transcription kit (Applied Biosystems, Foster City, Calif.). For experiments with more than 12 samples, we harvested PolyA+ RNA in 96-well plates with the Turbocapture mRNA kit (Qiagen) and reverse transcribed with the Sensiscript RT kit (Qiagen).

siRNA Collection siGENOME SmartPools (Dharmacon) were acquired from a genome-wide library available at ICCB (Harvard Medical School). siRNA pools targeting X genes were picked manually from the larger library and used to transfect cells and determine gene function. For HPS1 knockdown in screen follow-up experiments, 3 distinct Silencer Select siRNAs (Ambion) were pooled before transfection into cells.

siRNA Assays in Primary HBECs

HBECs were added to each well of 96-well plates as described previously (Shapira). 24 hours later, 25 nM final concentration of siRNA along with Hiperfect transfection reagent was added to each well and incubated at 37° C. for 3 hours, after which the cell media was changed. Cells were treated with siRNA for 3 days at 37° C. with one media change at 24 h post-transfection. Following knockdown, we used Alamar Blue (Invitrogen, Carlsbad, Calif.) to determine cell numbers in treated wells (in some replicate plates). Cells were then washed 2 times (with complete media). To assess influenza virus replication, cells were then inoculated with an amount of PR8 virus corresponding to a multiplicity of infection (moi) of 1 and incubated at 37° C. At 2 days post-infection, HBEC supernatants were harvested and frozen with 5 µg/ml TPCK trypsin. To assess IFN production in response to vRNA and ΔNS1, cells were transfected with 100 ng/ml RNA or infected with ANSI virus at a multiplicity of infection of 5. At one day post-transfection or infection, HBEC supernatants were harvested. Three independent tests of the described gene set were performed. Cell numbers following each assay were determined using Cell-Titer-Glo (Promega, Madison, Wis.).

shRNAs and Assays in Primary HBECs

High titer lentiviruses encoding shRNAs targeting genes of interest were obtained from The RNAi Consortium (TRC; Broad Institute, Cambridge, Mass., USA). HBECs were infected with lentiviruses at MOI-5. Examples of shRNA sequences used are listed in Table 3.

Virus Titering of Cell Supernatant

T cells were seeded and transfected as described previously (Shapira et al). At 24 h post-transfection, the cells were re-seeded in white Costar plates at a density of $10^4$. HBEC supernatants frozen with trypsin were added to the re-seeded reporter cells and incubated for 24 hours. Reporter activity was measured with firefly luciferase substrate (Promega, Madison). Luminescence activity was quantified with the Envision Multilabel Reader (Perkin Elmer, Waltham, Mass.) fitted with an automatic plate stacker.

Determining Interferon Production from HBEC Supernatant.

To measure levels of human IFNb we generated a 293T cell line containing an ISRE-Luc promoter. Briefly, cells were infected with a commercially available lentiviral expression system (SA Biosystems, Frederick, Md. Following selection with puromycin, cells were cloned by limiting dilution and tested for responsiveness to human IFNb (PBL Biomedical Laboratories, Piscataway, N.J.). Clone selection is as previously described (Shapira et al) To measure IFNb in supernatants from experimental assays, ISRE-Luc reporter cells were seeded in flat bottom white Costar plates at a density of $3 \times 10^4$/well. 24 hours later, supernatants were added and assayed for ISRE-Luc inducing activity. To read luminescence in plates, we used the Envision Multilabel reader (Perkin Elmer, Waltham, Mass.) fitted with an automated plate stacker.

qPCR Measurements

Real time quantitative PCR reactions were performed on the LightCycler 480 system (Roche, Indianapolis, Ind.) with FastStart Universal SYBR Green Master Mix (Roche). Each reaction was run in triplicate and GAPDH or b-actin levels were used as an endogenous control for normalization.

Nanostring

The nCounter system has been previously described. HBE or NHLF cells were treated with lysis buffer and stored at −80 C. Total RNA from the lysates were allowed to hybridize to the capture and reporter probe by incubation overnight at 65 C, following the nCounter Gene Expression Assay Manual. The target/probe complexes were washed, eluted, and immobilized in a cartridge for data collection in the nCounter Digital Analyzer. Detailed sequence information for the target regions, capture probes, and reporter probes is listed in Mouse Cells Mouse lung fibroblasts were derived from lung tissue of Ap3b1−/− and C57BL/6 mice; all mice were purchased from JAX and were in the C57BL/6 background. Cells were derived from 4-8 wk old female mice using a previously described protocol (Tager A M Am J Respir Cell Mol Biol. 2004). Cells were grown in DC15 media (DMEM, 15% FBS). Cells were used between passages 2 and 5 for experiments.

Pseudovirus

Plasmids to produce pseudovirus were a gift from M. Farzan. H5-HA was a gift from Wayne Marasco. MLV-GFP pseudoviruses were produced using a modified protocol of Huang et al 2008. Briefly, gag-pol, GFP, and EBOV GP, MARV GP, MLV env, MACV GP, LASV GP or LCMV GP plasmids were transfected into 293Ts using Transit LT1 reagent. For influenza pseudoviruses PR8 NA and either H1, H3, H5 or H7 HA were transfected. Virus was harvested and filtered 48 h post-transfection. Pseudoviruses were introduced to NHLF cells by centrifugation at 4000 rpm for 30 min at 4 C and incubated at 37 C for 1 hr before a media change. GFP expression in NHLFs was analyzed 48 h post-infection using flow cytometry.

Influenza Virus Labeling

Influenza virus X-31 was purchased from Charles River Laboratories and labeled with lipophilic dye DiD (Invitrogen) or cyanine dye Alexa 647 (Invitrogen) (Lakadamyali et al, Chen et al). For labeling, 100 μl of the original virus stock was incubated with 3 μl of 25 mM DiD dissolved in DMSO, or 3 μg Alexa 647 at room temperature for 2 h or 1 h with gentle vortexing. Unincorporated dye was removed by buffer exchange into the Hepes 145 buffer (50 mM Hepes, pH 7.4, 145 mM NaCl) by using NAP-5 gel filtration columns (GE Healthcare). The labeled virus was aliquoted, snap-frozen with liquid nitrogen, and stored at −70° C. Immediately before experiments, the labeled virus was thawed and filtered through a 0.2 μm pore size syringe filter (Supor membrane, Pall) to remove viral aggregates.

Viral Fusion Assay

Influenza virus X-31 was labeled with lipophilic dye DiD and absorbed by cells on ice for 30 minutes. After washing away unbound virus with cold PBS twice, cells were incubated in pre-warmed culture medium at 37° C. for indicated times. DiD was initially self-quenched before viral fusion with endosomes. After viral fusion and spreading of DiD on endosomal membranes, there is a dramatic increase of DiD fluorescence intensity. Cells were either fixed and processed by flow cytometery analysis, or kept alive in imaging buffer (9 parts DMEM without phenol red, 1 part pH 8 0.5M Hepes buffer) supplemented with 20 mM ammonium chloride Ammonium chloride will increase the pH of endosomes instantly to prevent any further viral fusion from happening. Cells were immediately imaged by confocal microscopy.

Confocal Microscopy

Labeled influenza virus X-31 was absorbed by cells in the presence of 1 μM Lysosensor Green (Invitrogen) for 45 minutes. After washing away unbound virus with cold PBS twice, warm culture medium supplemented with 1 μM Lysosensor Green was added. Cells were subsequently incubated at 37° C. for indicated time before fixation with 4% PFA. For immunofluorescence, samples were prepared similarly except no Lysosensor Green was present. After fixation, cells were washed with PBS and permeabilized by 0.1% Triton for 5 minutes, followed by incubation with blocking buffer (PBS containing 3% BSA) for 30 minutes. Cells were then incubated with antibody against EEA1 (Abcam ab2900, 1:500 dilution in blocking buffer) at room temperature for 1 hour. Cells were washed with PBS and incubated with secondary antibodies (Alexa 488 chicken anti-rabbit IgG, Invitrogen) diluted in PBS at room temperature for 45 minutes. Unbound secondary antibodies were removed by washing with PBS before imaging. Octadecyl Rhodamine B Chloride (R18, Invitrogen) was used to outline the plasma membrane. For confocal imaging, a 488 nm argon ion laser (Coherent) was used to excite Alexa 488 or Lysosensor Green; a 561 nm solid state laser (Crystalaser) was used to excite R18; a 647 nm krypton laser (Coherent) was used to excite Alexa 647 or DiD. The fluorescence emission was collected by an oil-immersed objective (60×) with numerical aperture 1.35 (Olympus).

Genome-Scale Pooled Lentivirus shRNA Screening $7 \times 10^6$ HBEs were infected with a pooled library of 54,000 distinct shRNA-expressing lentiviruses targeting 11,000 genes. 24 hours post-infection, cells were selected in puromycin at 0.5 μg/ml for 72 hours to ensure that all cells were infected. Cells were then treated with 1,000 units/ml of IFNB1 (PBL Interferon Resources) for 24 hours once they reached 80% confluence. IFNB1-treated cells were infected with influenza A virus PR8 at moi 5 for 16 hours. Cells were then collected for HA immunostaining using a monoclonal antibody to HA that was incubated with cells for 30 minutes at RT, followed by Alexa Fluor 488-conjugated goat anti-mouse IgG for 30 min Propidium iodide (PI) was added before cell sorting with a BD FACSAria III cell sorter. Viable (PI negative) PR8 influenza-infected (HA+) or uninfected (HA−) cells were collected and subjected to shRNA representation analysis. Briefly, DNA was isolated, shRNA sequences were PCR-amplified and hybridized to a custom Affymetrix microarray to quantify hairpin abundance. Data were preprocessed with modified Dchip software, and analyzed with the RIGER algorithm using the weighted second best metric to cluster ranked shRNAs into a ranked gene list.

Plasmids and Lentivirus Production

To create a plasmid for expressing SC35, SC35 ORF was amplified and cloned into the expression vector pIRES-V5. For the doxycycline inducible SC35 plasmid (dox-SC35-Flag), amplified SC35-Flag was cloned into a Tet-on lentivirus vector (pCW57d-P2AR). To create the siRNA-resistant SC35 plasmid (Dox-SC35-Flag (resistant)), silent mutations in the SC35 siRNA targeting site were introduced into Dox-SC35-Flag by using QuickChange lightning site-directed mutagenesis kit (Agilent). Primers used for mutagenesis are summarized in Supplementary Table 3. All constructs were verified by DNA sequencing. Lentivirus was produced in 293T cell using the packaging constructs psPAX2 and pCMV-VSVG.

siRNA and vRNA Transfection

HBEs or A549 cells were transfected with the Hiperfect transfection reagent combined with 25 nM pooled SC35 siRNAs (Dharmacon Cat# L-019711-00-0005), single SC35 siRNAs #1 and #2 (Ambion Cat# S12730), negative control siRNA (Ambion Cat#4390843) or Cell death siRNA (Qiagen Cat#1027298) for 3 hours at 37° C., followed by a media change. To achieve efficient knockdown in A549 cells, cells were transfected with siRNA again on the next day. Further experiments were performed 72 hours post-transfection. To study innate immune responses to RNA, cells in a 12-well plate were transfected with 500 ng of influenza vRNA using the transfection reagent LTX (Invitrogen).

PR8 Replication

To test PR8 replication by PR8 HA (Takara Bio) staining, knockdown cells were infected with PR8 at multiplicity of infection (moi) 2 for 16 hours. Cells were fixed with 4% formaldehyde and permeabilized with 0.1% Triton-X100. Cells were then incubated with monoclonal antibody to HA, followed by secondary antibody (Alexa Fluor 488 goat anti-mouse IgG). Immunofluorescence was detected by TTP LabTech Acumen eX3. To assess PR8 replication by vRNA-luciferase reporter that we developed in previous study (3), knockdown cells were infected with PR8 at moi 2 for 48 hours and then the cell supernatants were collected and treated with trypsin 5 µg/ml. 293T cells were transfected with vRNA-luciferase reporter plasmid and re-seeded in white Costar plates at a density of $2\times10^4$ each well of 96-well plate. Supernatants treated with 5 µg/ml trypsin were added to the re-seeded reporter cells and incubated for 24 hours. Reporter activity was measured with firefly luciferase substrate (Promega, Madison, Wis.), and luminescence was quantified with the Envision Multilabel Reader (Perkin Elmer, Waltham, Mass.).

RNA Isolation, RT-PCR and qRT-PCR

Collected cells were lysed with RLT (Qiagen) lysis buffer, and RNA was isolated with RNeasy mini columns, and reverse transcribed with the High Capacity cDNA Reverse Transcription kit (Applied Biosystems, Foster City, Calif.). To detect spliced isoforms, regular PCR was performed with Herculase II fusion DNA polymerases (Agilent) and PCR products were run on a 2.0% agarose gel. To quantify mRNA levels, real-time quantitative PCR reactions were performed on the LightCycler 480 system (Roche, Indianapolis, Ind.) with FastStart Universal SYBR Green Master Mix (Roche). Each reaction was run in triplicate and Gapdh or Hprtl levels were used as endogenous controls for normalization. Cycle thresholds were normalized to Gapdh levels and fold enrichments were set to the normalized unstimulated value where applicable.

Figure 1A:
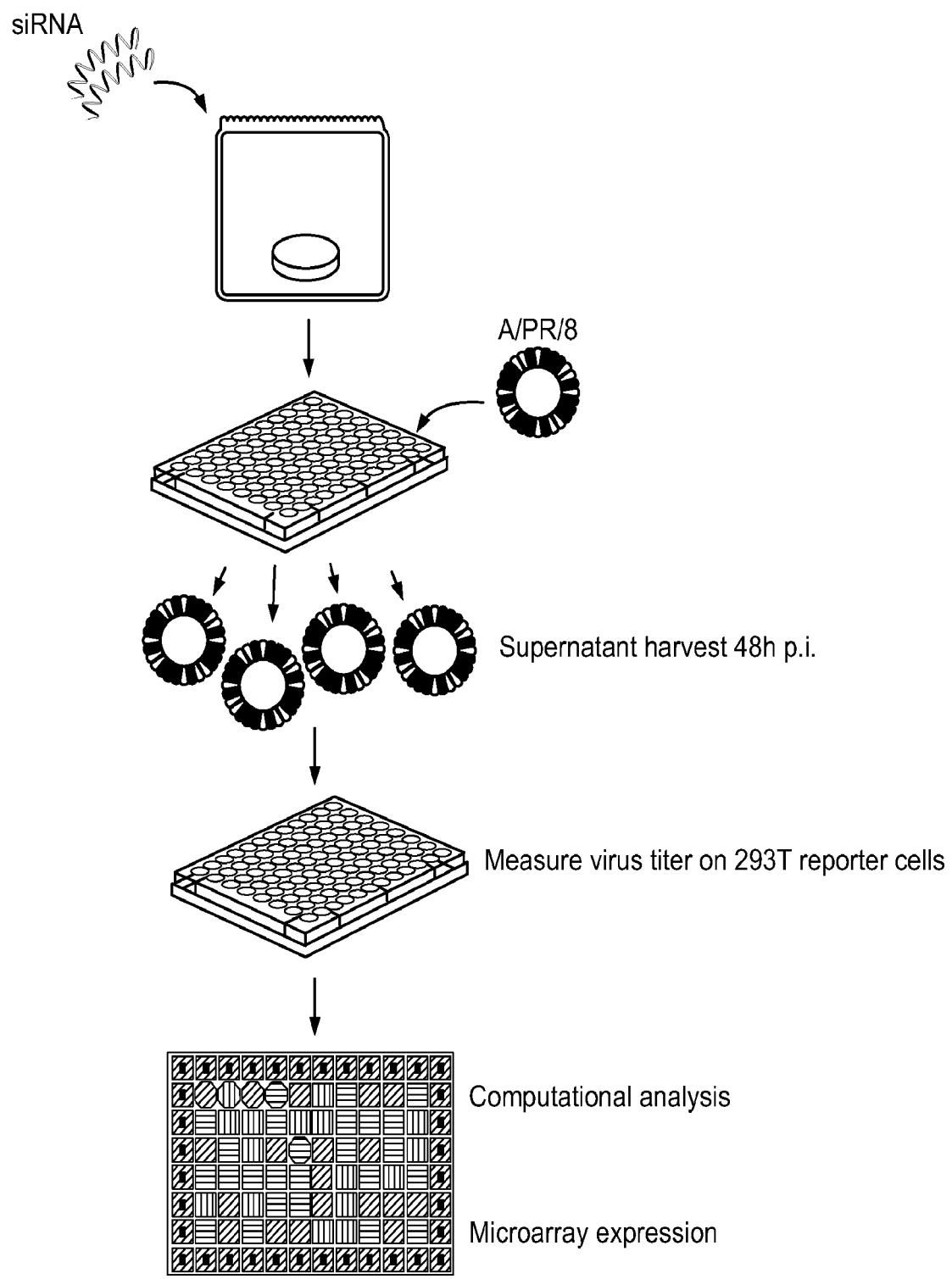
FIG. 1. Identification of cellular trafficking factors affecting influenza virus production. (A) Outline of the screening procedure. Primary human bronchial epithelial cells (HBECs) were transfected with siRNA pools and then infected with influenza (MOI=1). Infectious virus titer in cell media was measured 48 hours later using a 293T vRNA-luciferase reporter. Data normalization and robust-z-scores were determined using RNAeyes (A. Derr, Broad Institute). Non-expressed genes were eliminated using previously curated microarray data (Shapira et al., 2009) (B) Functional classes of genes targeted in the screen with annotations based on the DAVID database (NIAID). (C) Distribution of robust Z-scores representing influenza viral titer readings from cells transfected with different siRNAs. Candidate pro- and anti-viral genes are shown. Cutoffs for candidates are denoted with arrowhead. (D) Cellular map of trafficking factors that affect the influenza life cycle. The location of candidate proteins on the map was determined using information in the Gene Ontology and KEGG databases. Virus life cycle is not shown. Physical interactions (black lines) are shown for human-human (Ingenuity) and human-virus (Shapira et al., 2009) networks. Previously identified host factors are underlined. Green, pro-viral; red, anti-viral; grey, not significant; purple hexagon, viral protein.
Figure 1B:
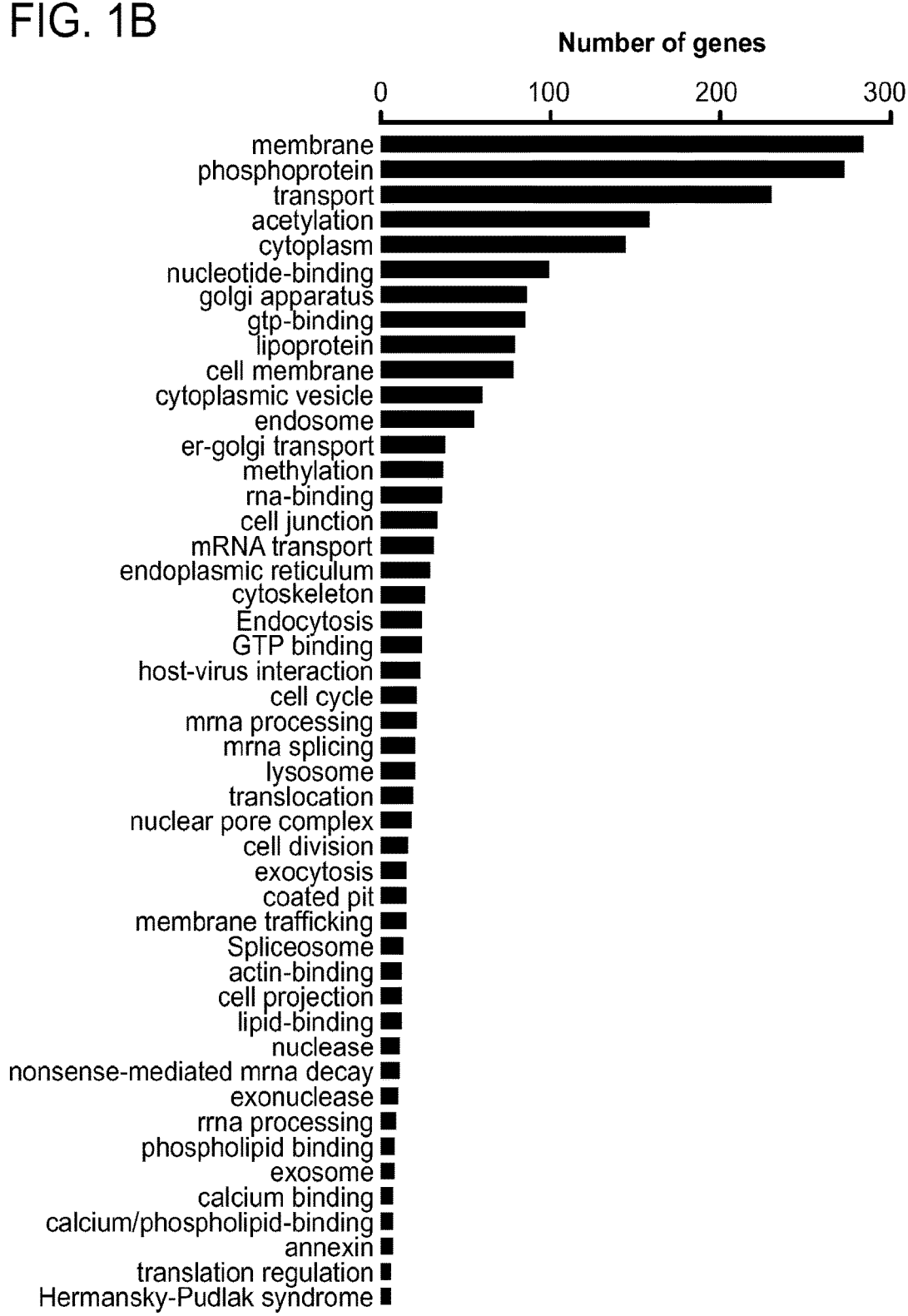

Example 2: Identification of Host Genes that Participate in Transport of Influenza Virus Components To identify host genes that participate in transport of influenza virus components during the viral life cycle, 437 manually curated genes implicated in vesicle trafficking and 52 genes implicated in nuclear transport were screened (FIG. 1B). Each candidate gene was perturbed in primary human bronchial epithelial cells (HBECs), a major target of influenza infection in humans, through the delivery of small interfering RNAs (siRNA). To assess the affect of gene silencing on virus replication, a luciferase reporter cell that detects infectious virus in cell supernatants 48 hours post-infection was utilized (described previously; Shapira 2009). Measuring infectious A/PR/8/34 viral particles allowed us to identify genes that affect any stage of the viral life cycle.

Figure 1D:
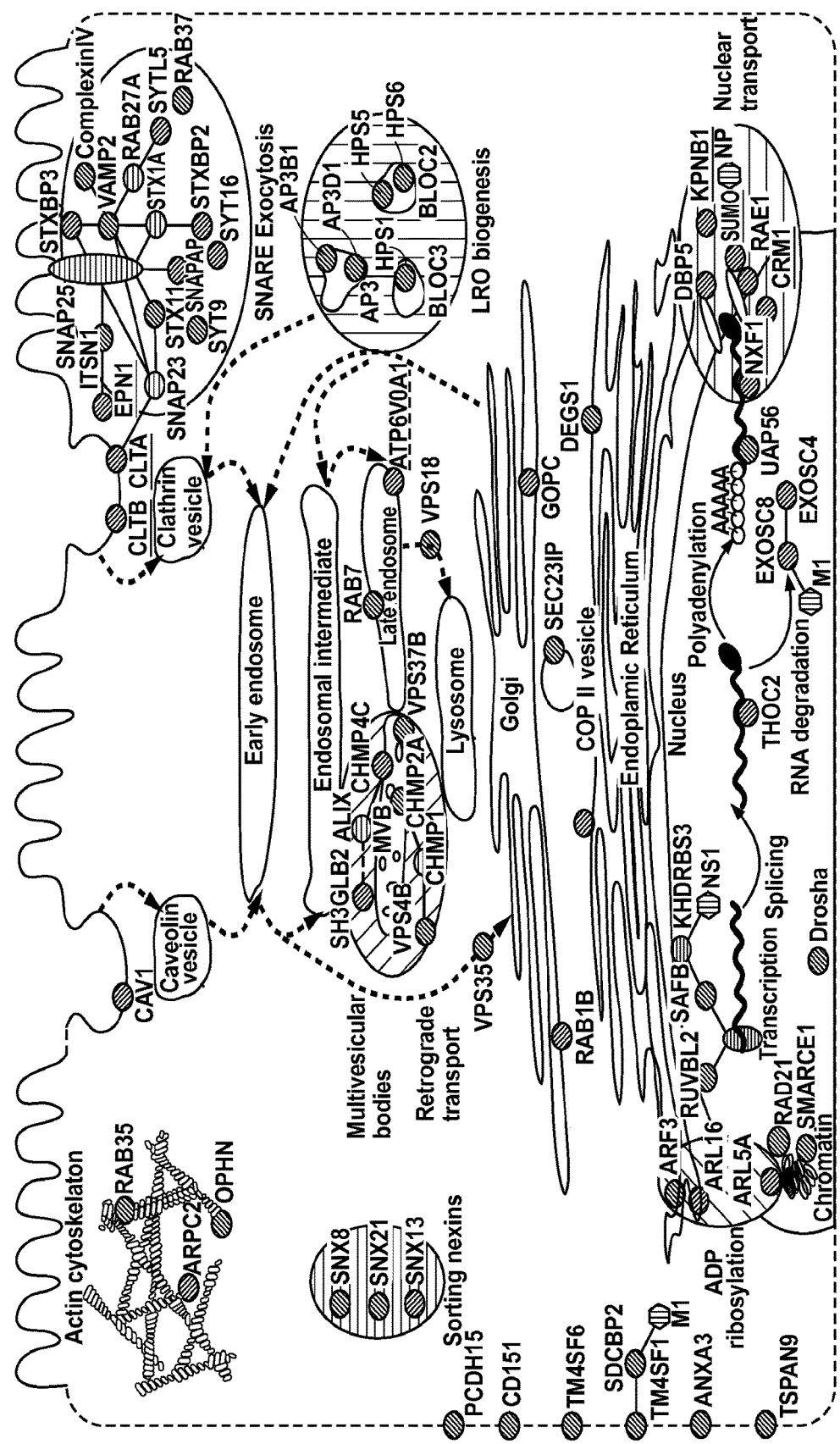

Silencing of 24 genes led to decreased viral replication (pro-viral) while silencing of 36 others increased it (anti-viral) (FIG. 1C) Importantly, a previously undetermined role for cellular processes such as SNARE-mediated exocytosis and sorting nexins in the influenza life cycle was elucidated (FIG. 1D). Additionally, phenotypes for multiple genes previously shown to have a role in influenza replication were confirmed, including NXF1, XPO1, SUMO1 and GOPC (pro-viral) as well as RUVBL2 (anti-viral) (Konig 2009; Kawaoka paper).

Four genes were found to be associated with one disease, Hermansky-Pudlak syndrome (HPS; AP3B1 HPS1, AP3D1 and HPS5) as anti-viral factors. Furthermore, a fifth gene, HPS6, was identified in our previous RNAi screen and had a phenotypic score comparable to the IRF3 and IFITM2 restriction factors. HPS is a rare disorder characterized by occutaneous albinism, platelet defects, neural defects, and pulmonary fibrosis. The genes coding these proteins have little homology and proteins encoded by these genes form four distinct complexes: BLOC-1, BLOC-2, BLOC-3, and the AP-3 complex, which are all believed to be involved in the biogenesis of lysosome related organelles. Some HPS mutations are also associated with immunodeficiency and severe respiratory infections in humans. Several hypotheses suggest how AP3B1 mutations result in a reduced capacity to fight infection, including through AP3B1's regulation of the formation of lytic granules in CTLs and NK cells and its role in TLR7 and TLR9 localization plasmacytoid dendritic cells (pDCs) (Iwasaki, Beutler).

Example 3: Knockdown of Genes Results in Higher Virus Production

Figure 2A:
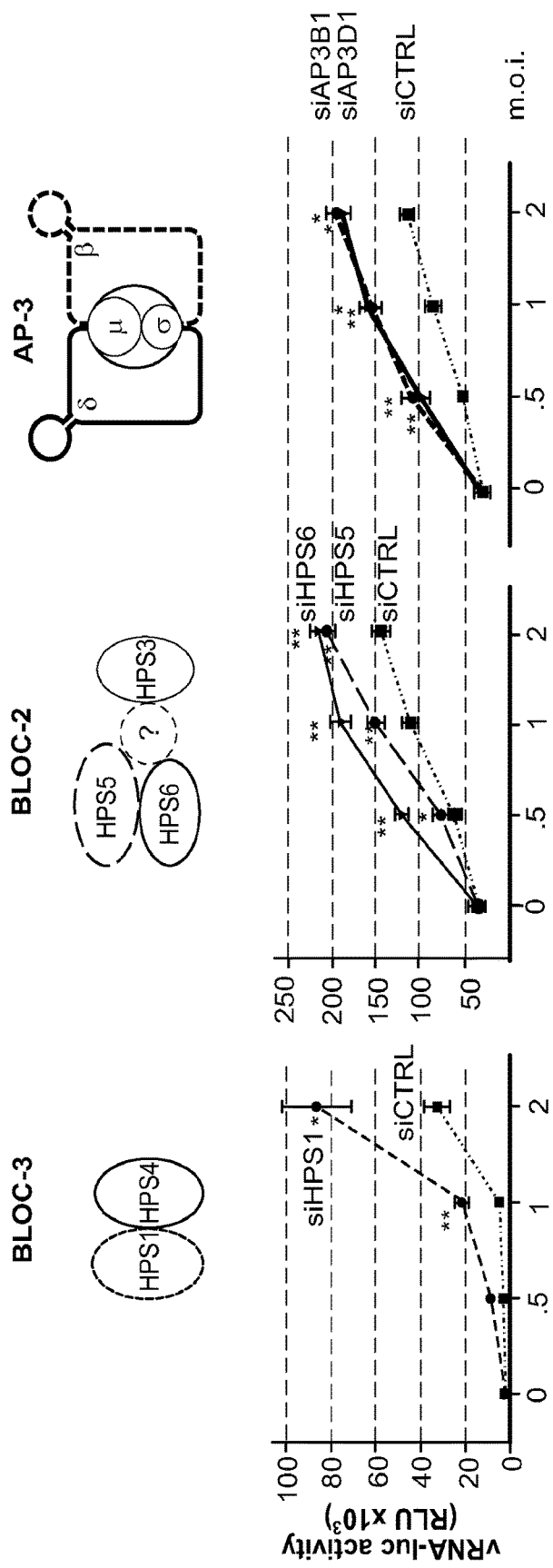
FIG. 2. HPS proteins have shared and unique roles in inhibiting influenza production. (A) Depletion of components from BLOC complexes leads to higher viral production in HBECs. HBECs were transfected with the indicated siRNAs (targeting one or more factors in 3 distinct complexes) and then infected with influenza strain PR8. Infection was allowed to proceed for 24 hours. Medium from infected cells was added to 293T vRNA reporter cells and viral titer was assessed based on reporter luminescence (RLU, relative luminescence units). Values represent mean+/−SEM, n=5 replicates. Diagram of the BLOC-3 (left), BLOC-2 (center), and AP-3 (right) complexes (top). (B) Depletion of multiple components within the same complex is equivalent to depletion of a single component. (C) Depletion of components from different complexes enhances influenza production more than depletion of a single complex component. ^ $p<0.05$ compared to AP3B1 alone, ^^ $p<0.01$. * $p<0.05$, ** $p<0.01$.
Figure 2B:
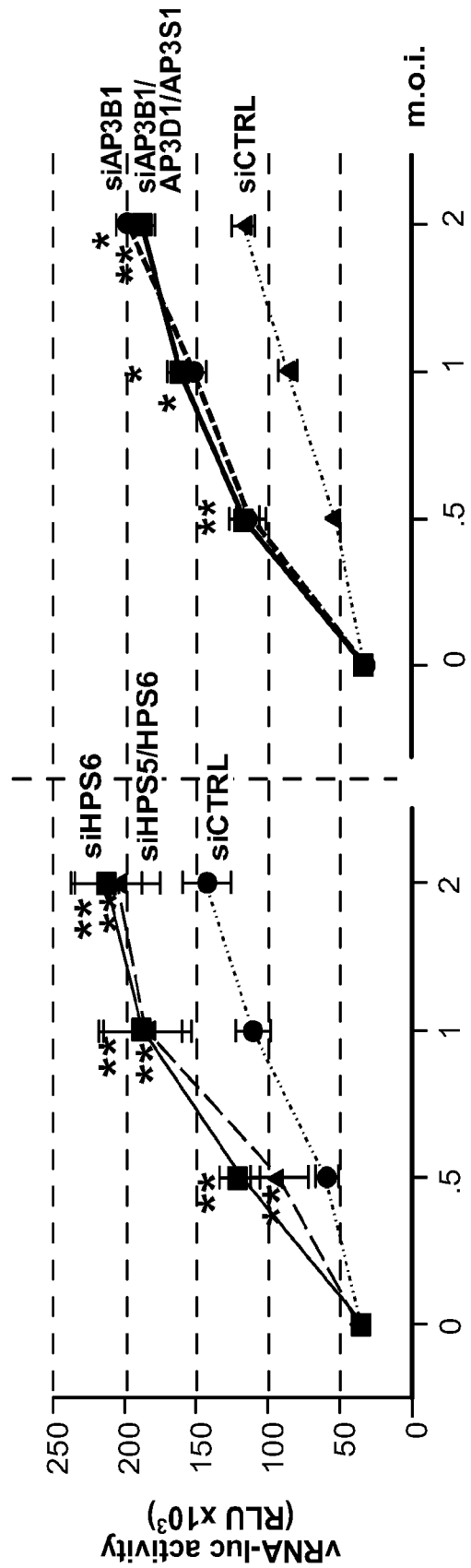
Figure 2C:
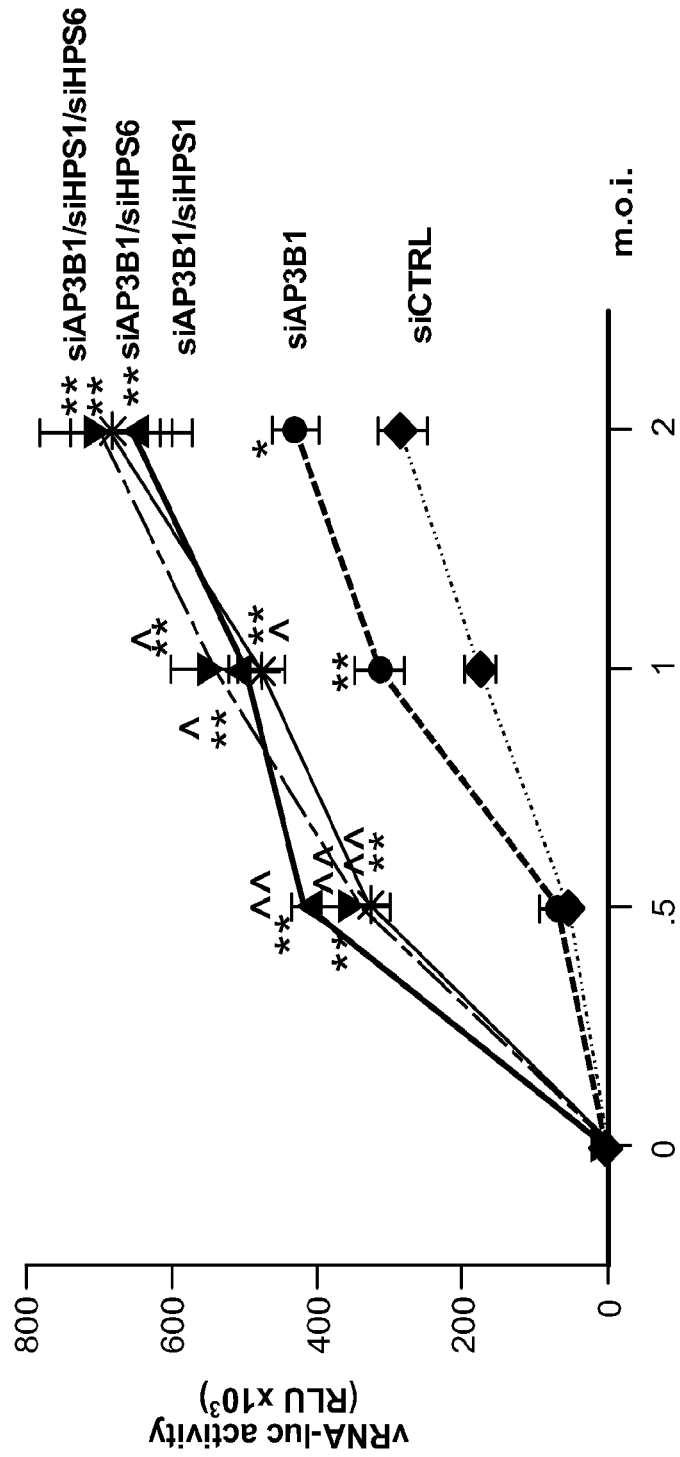
Figure 3A:
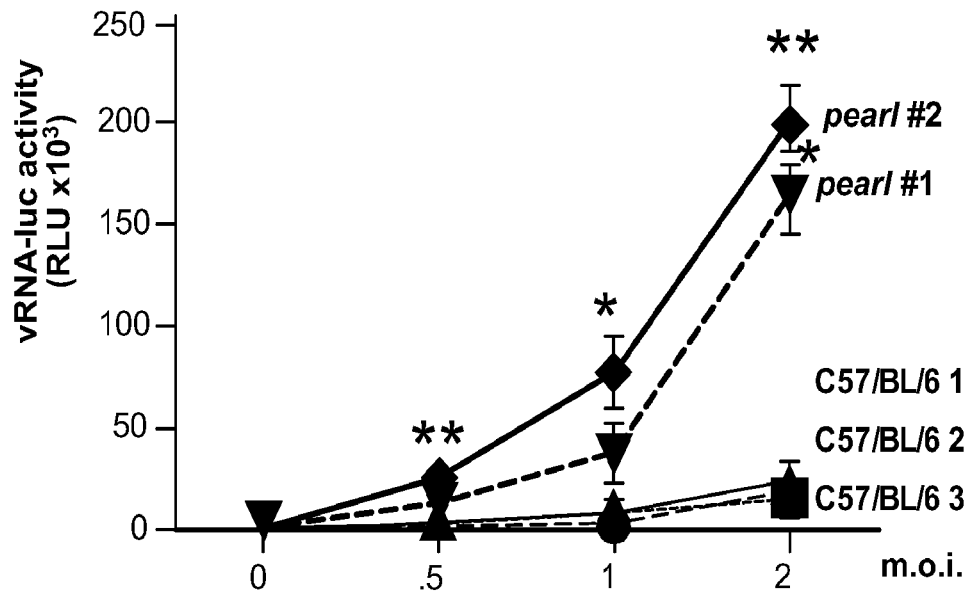
FIG. 3. Mouse and patient cells with HPS mutations exhibit enhanced influenza susceptibility. (A) Cells from Ap3b1 and Hps1 mutant mice produce more virus than control cells. Primary mouse lung fibroblasts from C57BL/6 mice and Ap3b1 mutant (pearl, pe/pe) mice (top panel, N=5) or from mutant and heterozygote Hps1 mice (pale-ear, ep/ep and ep/+, respectively) (bottom panel, 2 mice, N=9) were infected with influenza strain PR8 for 24 hours. Medium from infected cells was added to 293T vRNA reporter cells and viral titer was assessed. (B) HPS-1 patient cells exhibit enhanced influenza susceptibility and production. Normal human lung fibroblasts (NHLFs) from three healthy patients and one HPS1 patient were infected with PR8 virus for 24 hours. Medium from infected cells was added to 293T vRNA reporter cells and viral titer was assessed, N=8. (C) Overexpression of HPS1 in HPS1-mutant lung fibroblasts rescues their influenza susceptibility. NHLF and HPS1-mutant cells were transduced with lentivirus containing either GFP or HPS1. 48 hours later, cells were infected with PR8 virus for 24 hours, and viral titer was assessed using vRNA reporter cells. N=3. (D) Monocytes from HPS-1 patients exhibit enhanced influenza susceptibility and viral production. CD14+ monocytes were isolated from peripheral blood of two HPS-1 patients (HPS1.284 and HPS1.101) and two matched healthy controls per patient. Cells were infected with PR8 virus for 8 hours, and viral RNA load was assessed using qPCR, N=3. Values represent mean+/−SEM. *, $p<0.05$; **, $p<0.01$.
Figure 3A:
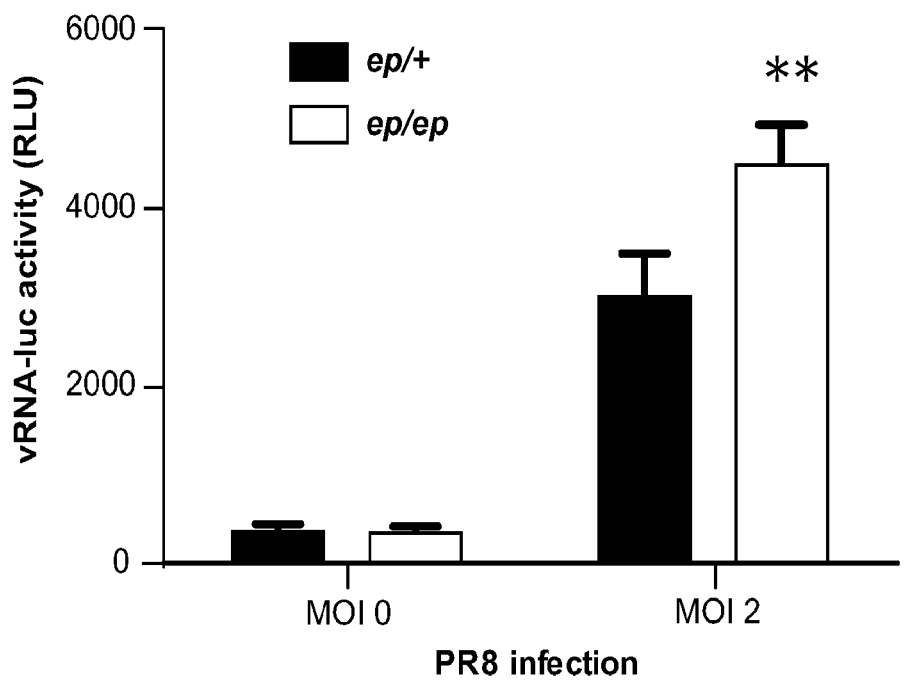
Figure 3B:
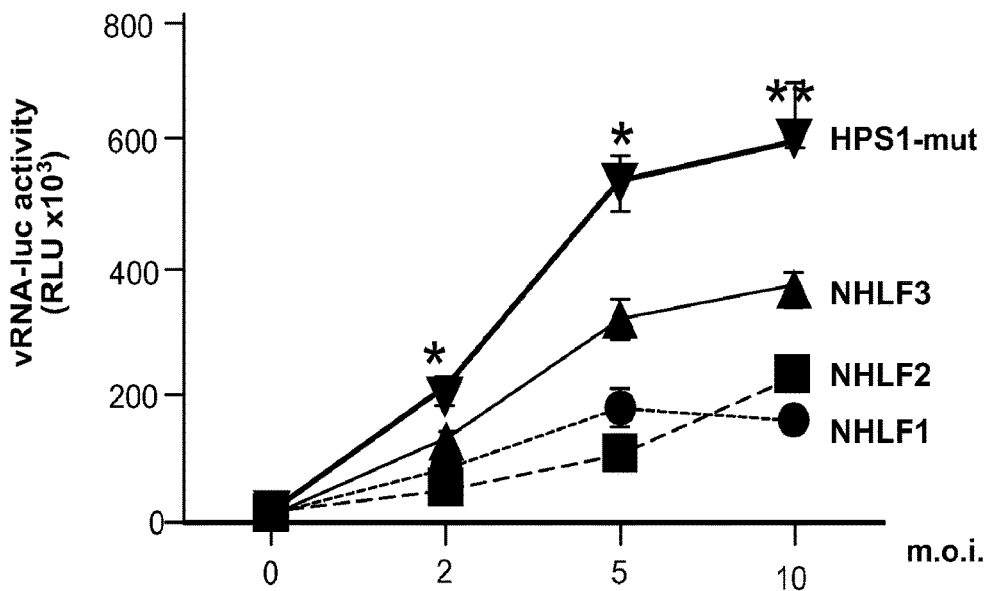
Figure 3C:
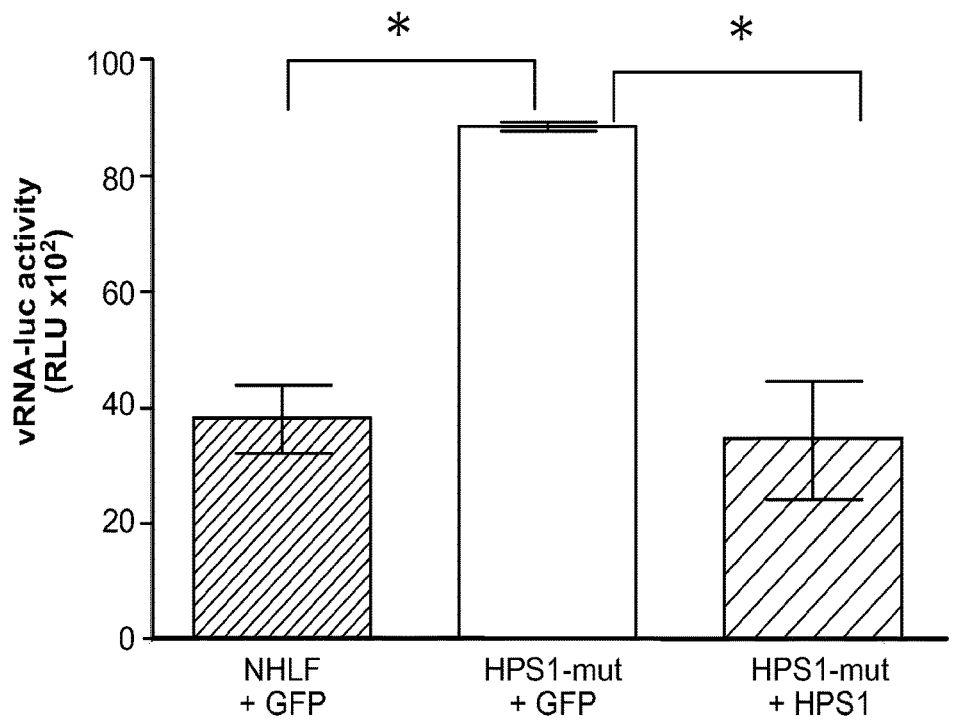
Figure 3D:
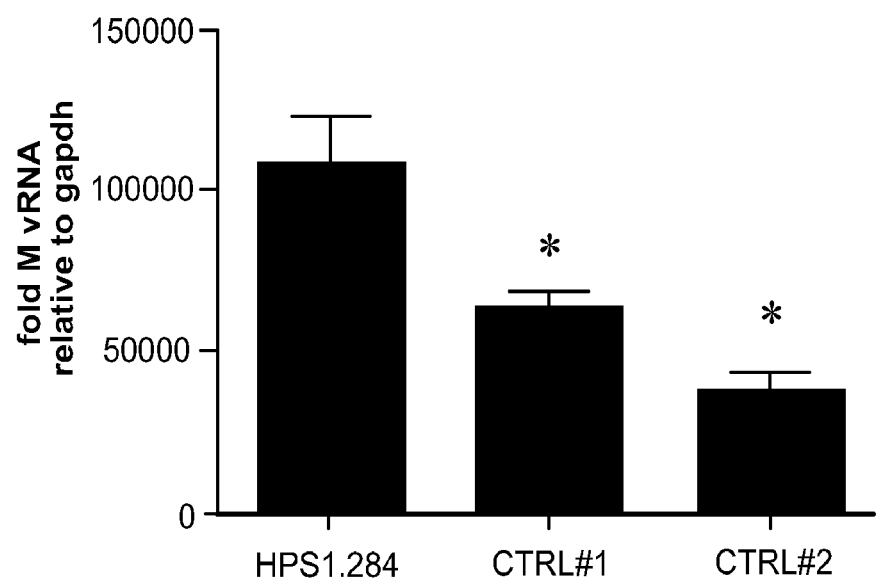
Figure 3D:
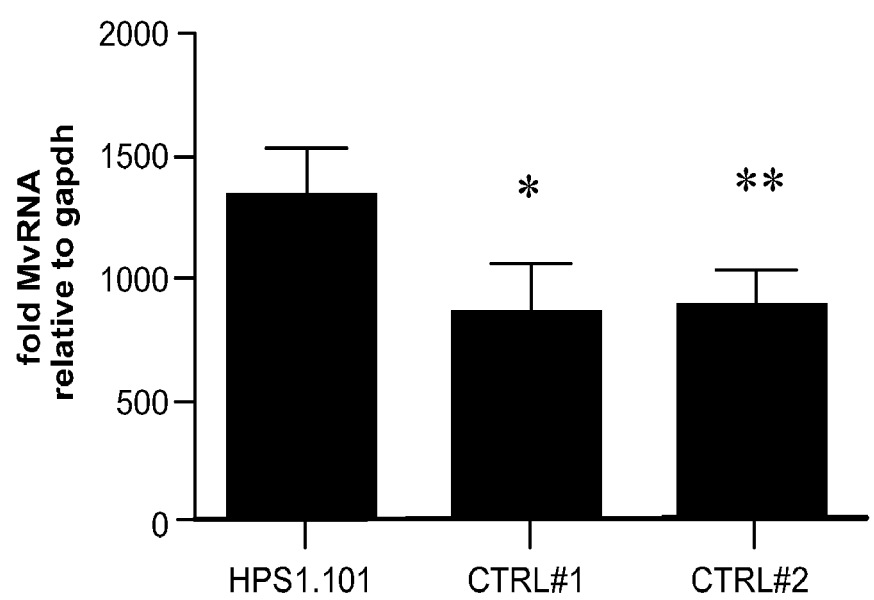
Figure 10A:
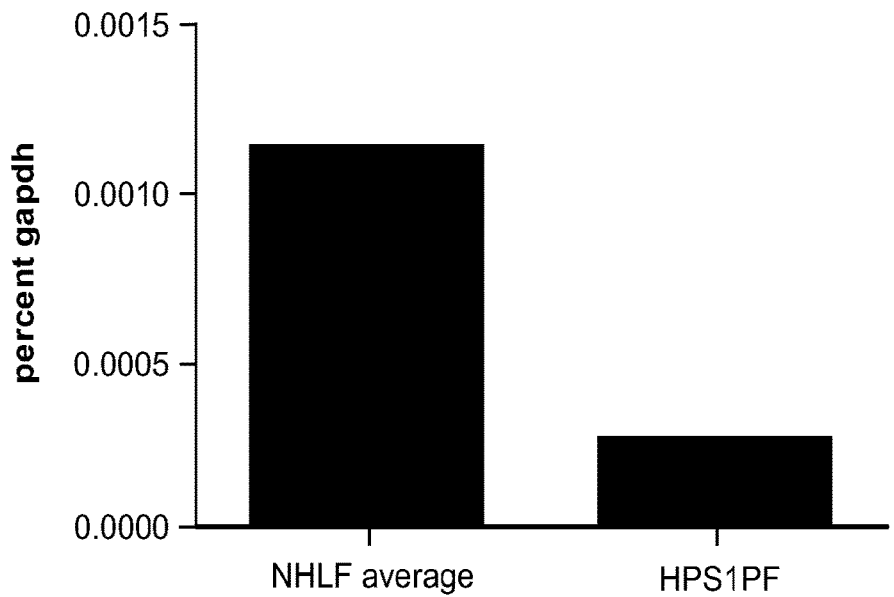
Figure 10B:
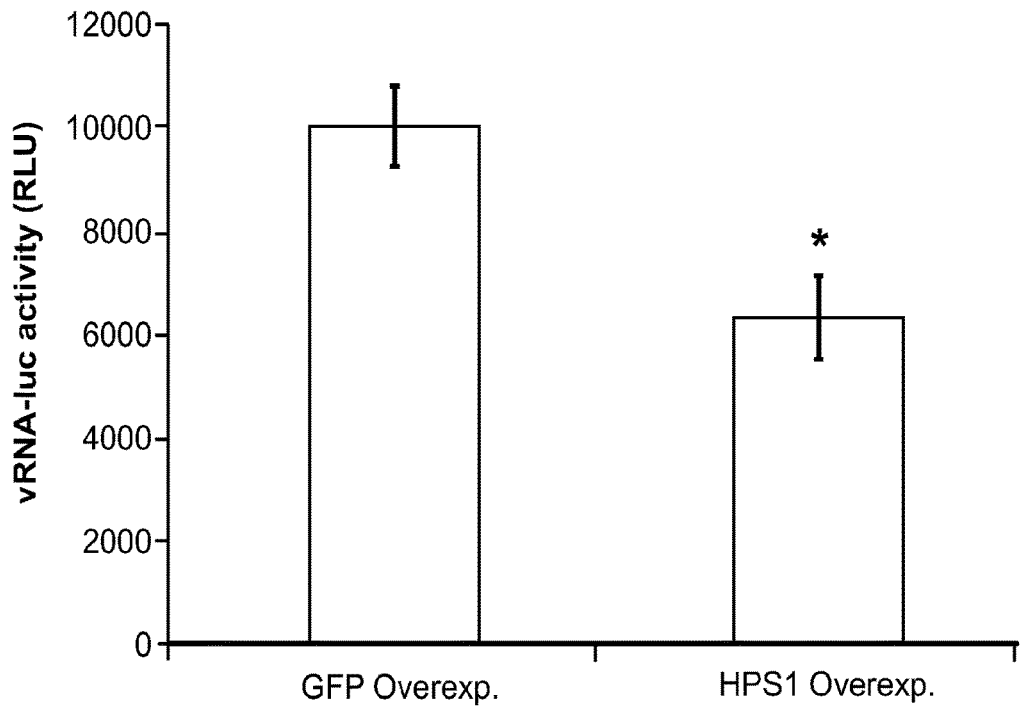
Figure 10C:
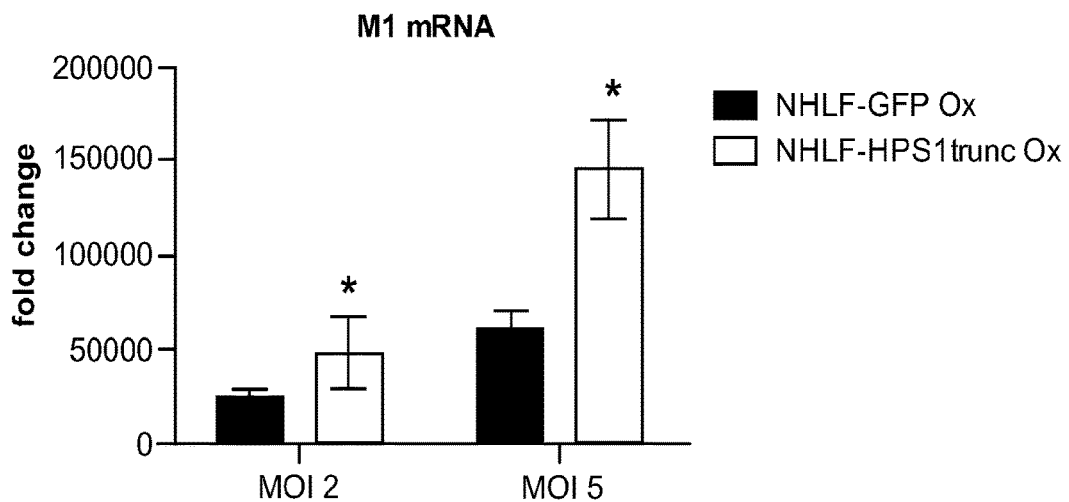
Figure 10C:
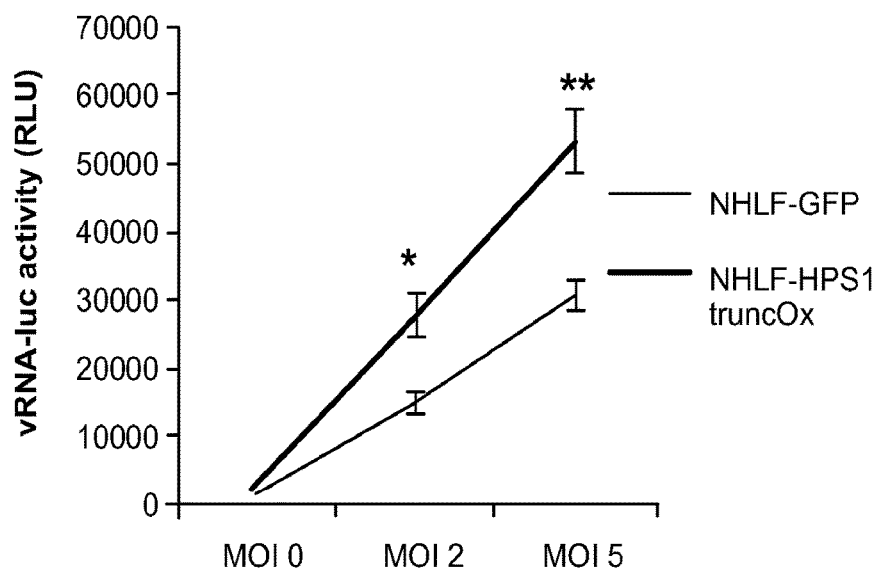

Infection of HBECs depleted of AP-3, BLOC 2, and BLOC3 complex proteins resulted in a consistent increase in virus production across multiple MOIs and timepoints (FIGS. 2 and 9A). Furthermore, primary murine lung fibroblasts (pMLFs) from AP-3 deficient pearl mice and HPS1 deficient pale ear mice had a marked increase in influenza virus production as compared to C57BL6 controls (FIGS. 3A and 9B). Although human HPS patients are exceedingly rare, primary normal human lung fibroblasts (NHLFs) were obtained from an HPS1 human patient with a 16 bp duplication in exon 15 of HPS1 and reduced expression in HPS1 by qPCR (FIG. 10A). Infection of HPS1$^{mut}$ patient cells with WT influenza virus resulted in enhanced viral production as compared to three NHLF controls (FIG. 3B). Primary human monocytes from two additional HPS1 patients also produced higher influenza titers than matched control patients (FIG. 3D). In addition, overexpression of HPS1 could restore normal viral production in HPS1$^{mut}$ patient cells (FIG. 3C). Overall, these data validate a role for BLOC proteins as antiviral factors in lung epithelial cells and demonstrate a potential mechanism by which HPS patients develop immunodeficiency.

Given that multiple BLOC proteins restrict influenza production, yet have some distinct functions in the biogenesis of lysosomal organelles, it was of interest to determine whether the contribution of each complex to restricting influenza replication was distinct or overlapping. While siRNA knockdown of multiple components from the same complex had no additive effect on virus production (FIG. 2B), knockdown of components across different complexes enhanced the virus replication phenotype (FIG. 2C). Together, these results indicate that HPS proteins act to restrict viral replication and that each complex likely has distinct and non-overlapping functions.

Example 4: BLOC Genes Act to Restrict Viral Replication

Figure 4A:
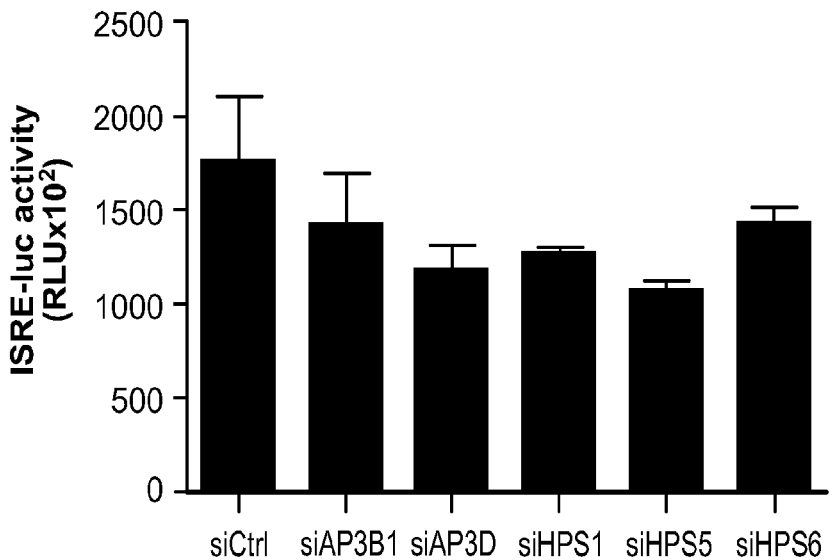
FIG. 4. HPS proteins restrict influenza virus replication through a mechanism not involving interferon production or responsiveness. (A) Interferon (IFN) production is unaffected in HBECs treated with siRNAs targeting HPS genes. Cells were stimulated with ANSI influenza for 24 hrs. Supernatants were placed on a 293T ISRE-luciferase reporter cell line to measure IFNa/b activity. (B) IFN production is unaffected in HPS1-mutant fibroblasts. Cells were treated with either ANSI virus or viral RNA for 24 hours. Supernatants were placed on a 293T ISRE-luciferase cell line to measure IFN production. (C) IFN b pretreatment diminishes overall PR8 replication but does not alter the relative replication enhancement caused by HPS gene depletion. HBECs were transfected with the indicated siRNAs, treated with IFN b for 18 hours and then infected with PR8 virus. Viral titer was assessed using the vRNA-luciferase reporter. (D) HPS1 does not affect interferon-related transcriptional responses. NHLF or HPS1-mutant fibroblasts were treated for 8 hours with IFN b, viral RNA, ANSI virus, or 3 MOIs of PR8 virus. Cell lysates were analyzed for RNA levels using Nanostring. * $p<0.05$, ** $p<01$.
Figure 4B:
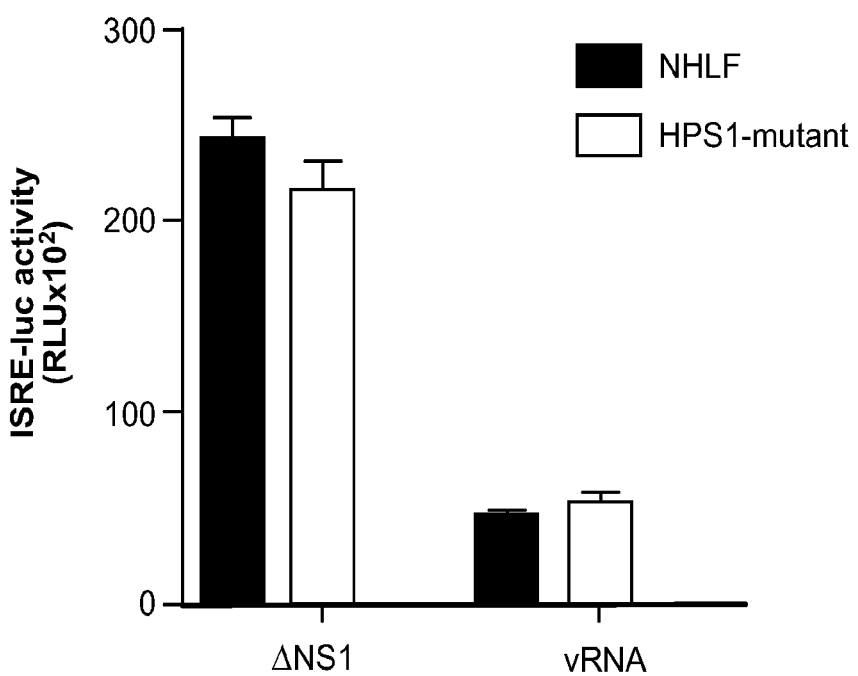
Figure 4D:
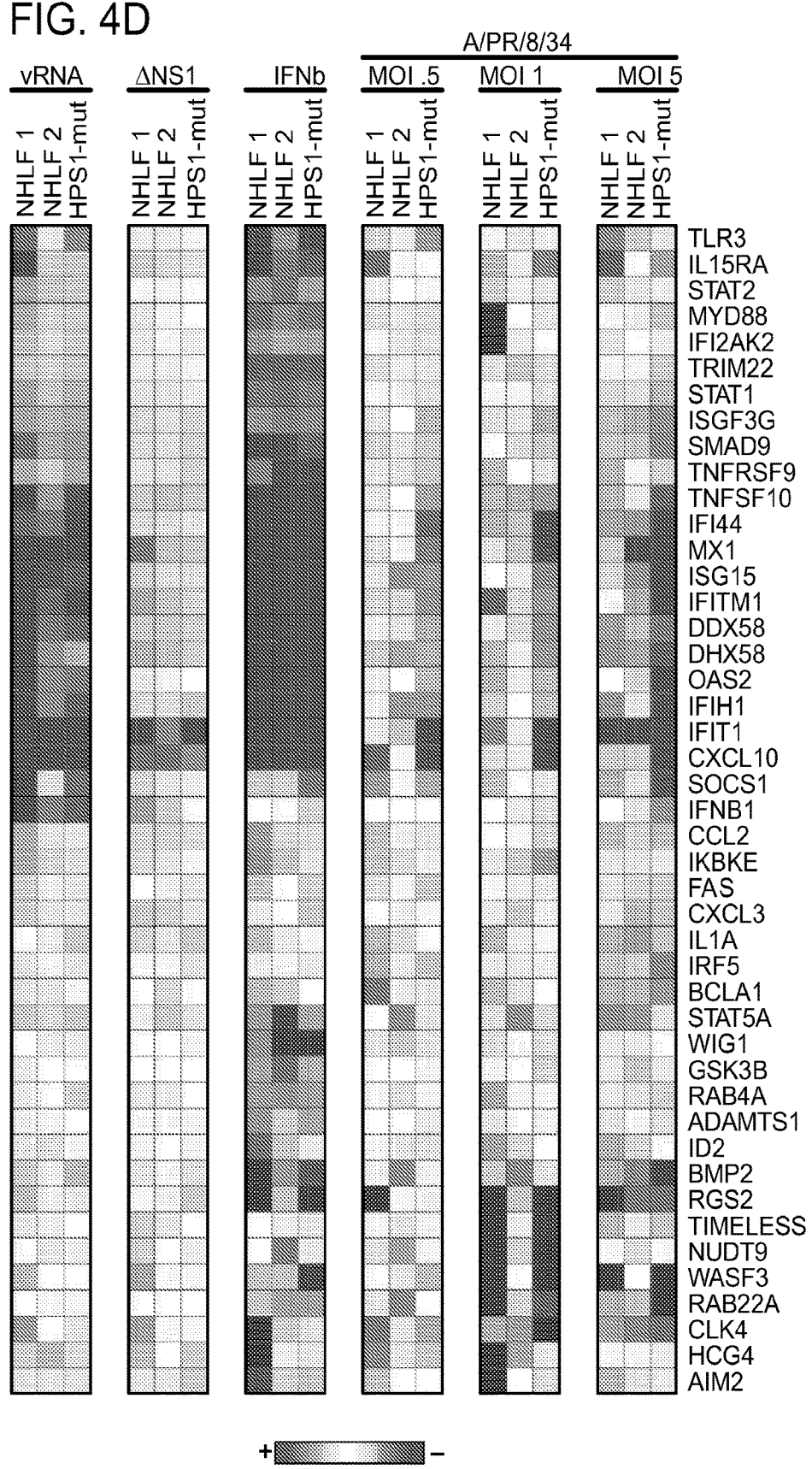

An indispensable component of cellular control of influenza virus infection is the initiation of innate immune responses and the production of Type I interferons, which include IFNβ. While pDCs are major producers of IFNβ, these sources of interferon are not sufficient for control of viral replication; activation of RNA sensing pathways in epithelial cells and their production of interferon is critical for initiating an anti-viral state and resistance to influenza. To test if BLOC components participate in the epithelial cell IFN response circuit, interferon-primed WT and HPS gene knockdown cells were infected with influenza at multiple MOI and monitored viral replication. While interferon pretreatment reduced overall viral replication, knockdown of AP3B1, AP3D1, HPS1, HPS5 and HPS6 still resulted in enhanced viral replication (FIG. 4C). In fact, interferon pretreatment may enhance the viral replication phenotype in HPS6 depleted HBECs. The ability of HBECs depleted of BLOC components to respond to ANSI influenza virus infection was also monitored, and no significant difference was found from control cells (FIG. 4A). In addition, HPS1$^{mut}$ cells responded normally to both ΔNS1 and transfected viral RNA (vRNA) (FIG. 4B), illustrating that while BLOC proteins complement the anti-viral effect of IFNβ, these proteins do not control the sensing of viral infection or the production and secretion of this cytokine. While the above findings suggest that BLOC genes act to restrict viral replication even in the presence of IFNβ, they do not exclude the possibility that BLOC proteins participate in regulating a more generalized IFNβ response signature. The transcriptional responses to IFNβ stimulation were similar between control NHLF and HPS1$^{mut}$ cells (FIG. 4D). Furthermore, HPS1$^{mut}$ cells exhibited transcriptional responses to viral RNA, NS1 deleted virus (ΔNS1) that were comparable to NHLF controls (FIG. 4D). Though recent reports propose a role for HPS and AP-3 complex genes in TLR signaling in pDCs, these results suggest that BLOC proteins have a distinct role in epithelia. In addition, these findings illustrate that HPS1 is dispensable for the interferon response pathway and restricts influenza replication independently of epithelial cell responses to this cytokine.

Figure 5A:
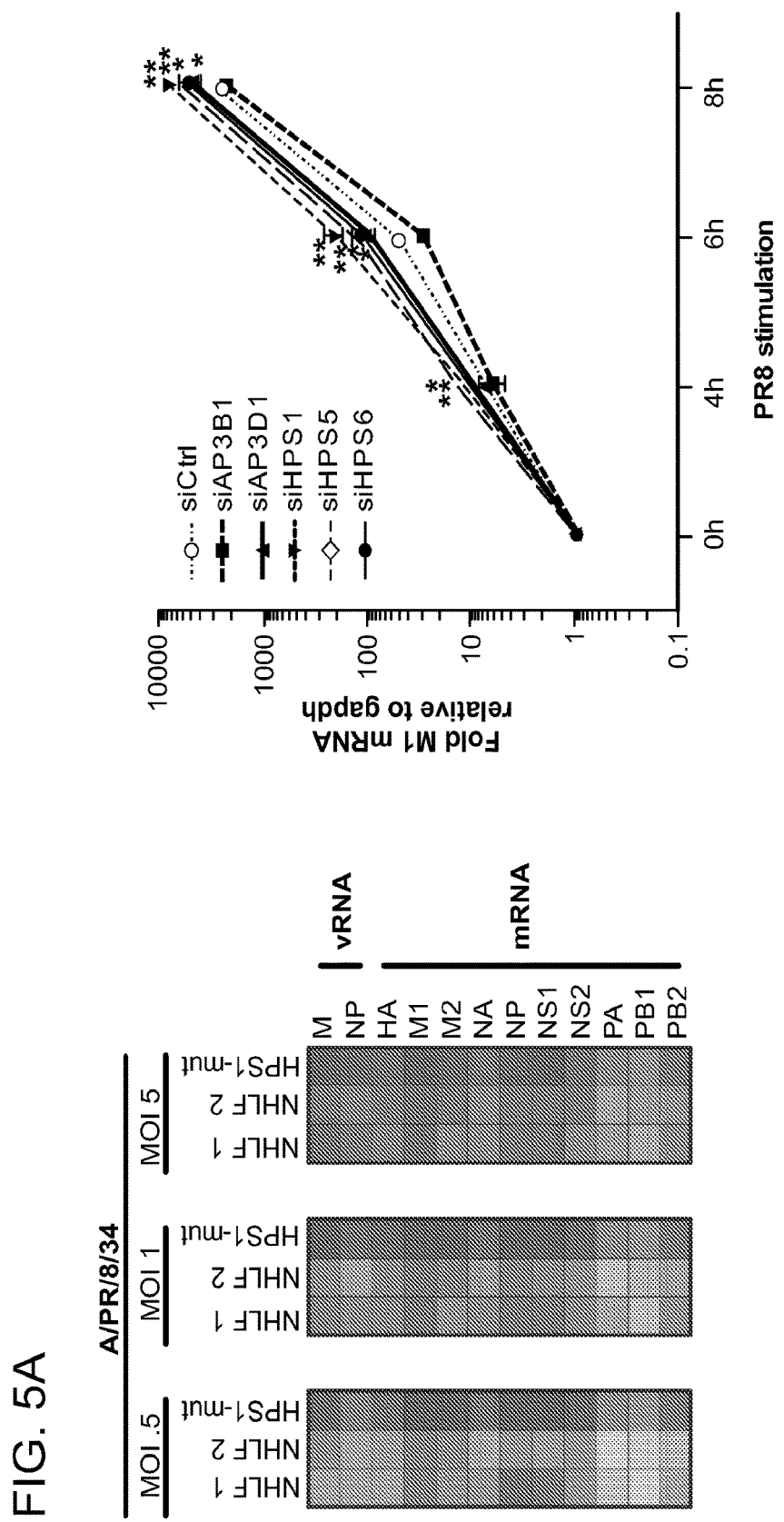
FIG. 5. HPS1 depletion affects a post-internalization, envelope-dependent stage of the viral life cycle. (A) Depletion of HPS genes leads to higher levels of viral RNAs. NHLF or HPS1-mutant fibroblasts were infected with PR8 virus (left panel) for 8 hours viral RNA levels were measured using Nanostring. siRNAs were used to silence HPS genes in HBECs (right panel) and the expression of the M transcript (mRNA) relative to b-actin was assessed post-infection at 4, 6, 8 hours. Levels were normalized to t=0. (B) Binding of virus to the cell surface is unchanged in NHLF or HPS1-mutant fibroblasts. DiD-labeled X31 (H3N2) influenza virus was bound to NHLF and HPS1-mutant cells at 4°

Despite normal transcriptional responses to transfected vRNA, infection with ΔNS1 influenza or stimulation with IFNβ, HPS1$^{mut}$ cells display enhanced transcription of interferon-stimulated genes (ISG) in response to WT influenza infection (FIG. 4D). HPS1$^{mut}$ cells had a significant increase in viral genomic and mRNA transcripts that may serve as ligands for cellular sensing machinery like RIG-I (FIG. 5A, left panel). Viral mRNA expression in HBECs depleted of BLOC components was also monitored and an increase in viral transcripts was found as early as 4 h post-infection, indicating that they act at an early stage of viral infection (FIG. 5A, right panel).

Example 5: Effect of BLOC Complexes on Viral Entry

Figure 5B:
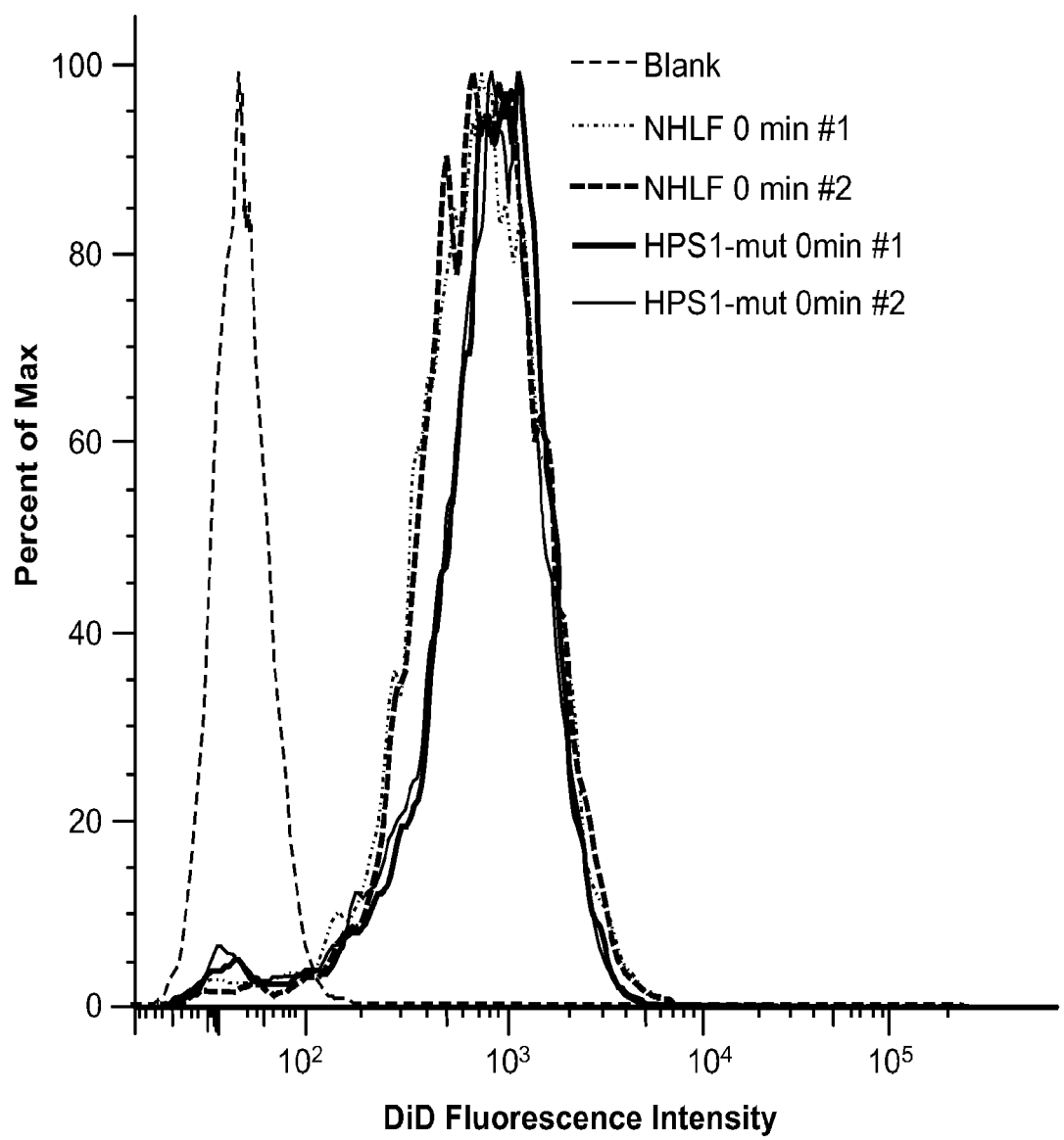
Figure 5C:
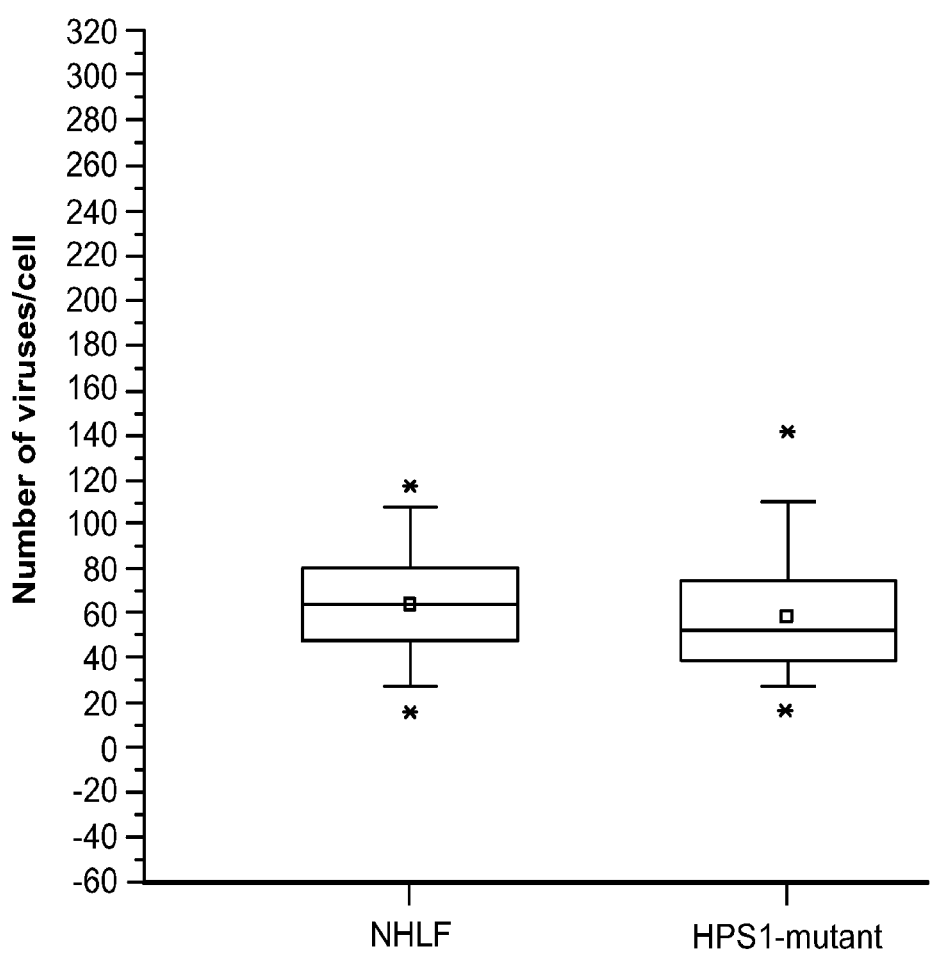
Figure 5E:
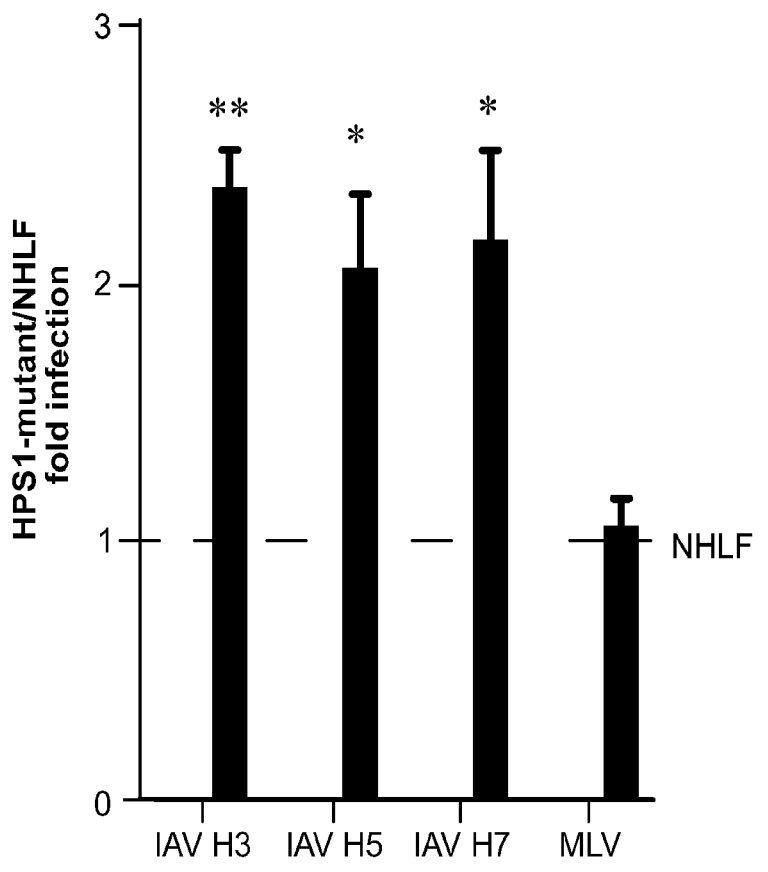

Given this early effect on viral replication and the cytosolic localization of HPS proteins, it was hypothesized that BLOC complexes affect viral entry. A critical step in viral replication is the entry of particles into cells. To monitor the entry steps that require the viral envelope proteins, the uptake of pseudo-virus particles was assessed that contain a murine leukemia virus (MLV) genome encoding EGFP and are coated with the envelope proteins (HA and NA) from A/PR/8/34. A 2.6-fold increase in GFP+ cells was observed in HPS1$^{mut}$ cells as compared to three NHLF control cell lines (FIG. 5D). To determine if HPS1 affects other influenza subtypes, pseudo-virus containing H3, H5 and H7 coats were also tested and a 2-fold or greater increase in GFP+ HPS1$^{mut}$ cells was observed, indicating a general effect of HPS1 on influenza entry (FIG. 5E). These effects were not due to steps in MLV entry or integration, as amphotrophic MLV entry was not affected by the absence of HPS1 (FIG. 5B, 5C). Next, pseudoviruses were tested for new and old world arenaviruses and filoviruses to determine if HPS1 restricts viruses utilizing distinct entry pathways. Filoviruses and influenza A viruses traffic from early to intermediate and late endosomes post-entry and require low pH for fusion, while arenaviruses reach acidified late endosomes either through sorting endosome intermediates (MACV) or directly through an unknown mechanism (LASV, LCMV). It was found that filoviruses, specifically Marburg (MARV) and Ebola (EBOV), are restricted by HPS1 but that old and new world arenavirus entry, specifically Lassa virus (LASV), Lymphocytic choriomeningitis virus (LCMV) and Machupo virus (MACV), were unaffected by the absence of HPS1 (FIG. 6C). The restriction pattern also narrowed down the potential mechanisms of HPS1 viral restriction, and together, these results indicate that HPS1 restricts viral entry during the endosomal maturation process to an acidified late endosomal compartment.

Figure 6B:
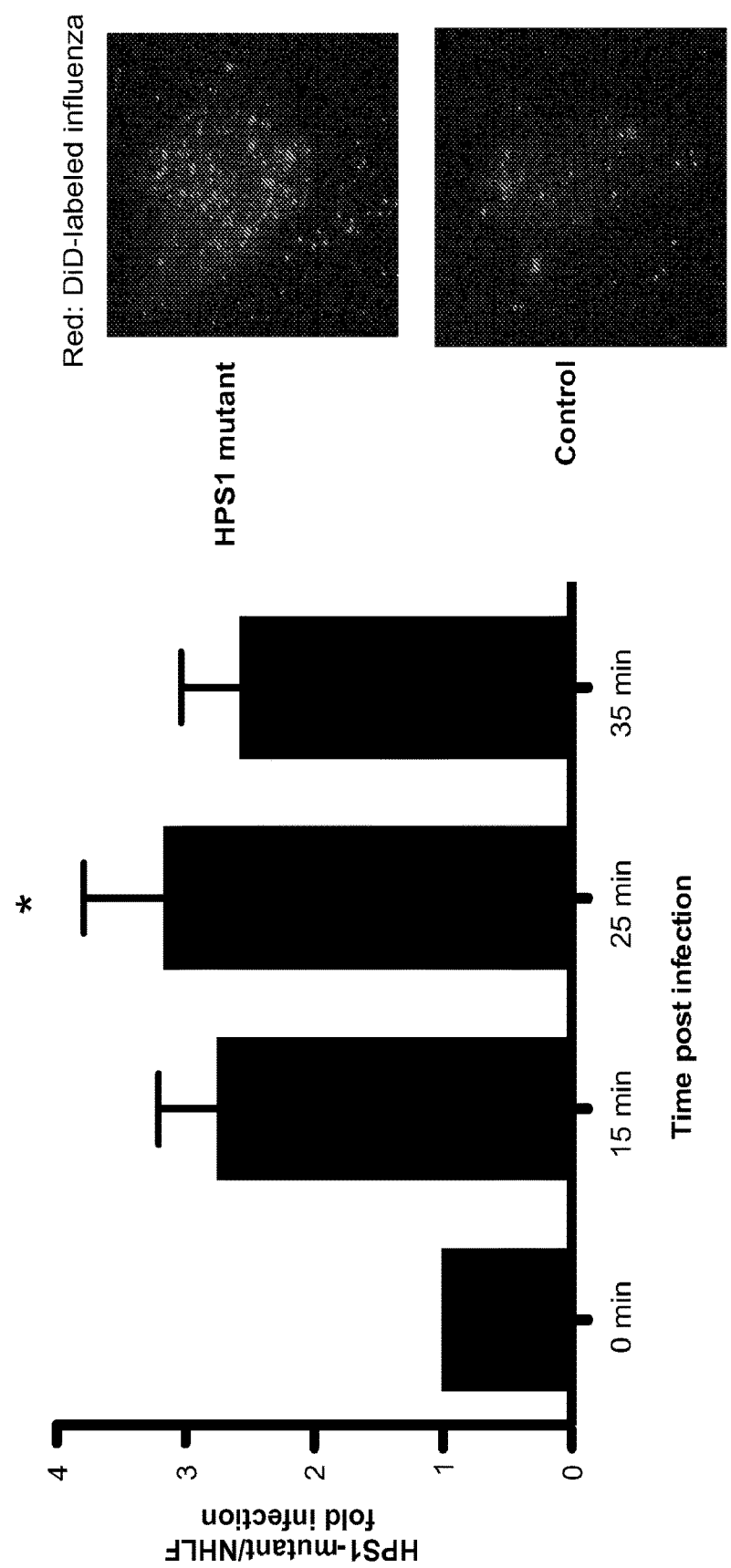
Figure 6C:
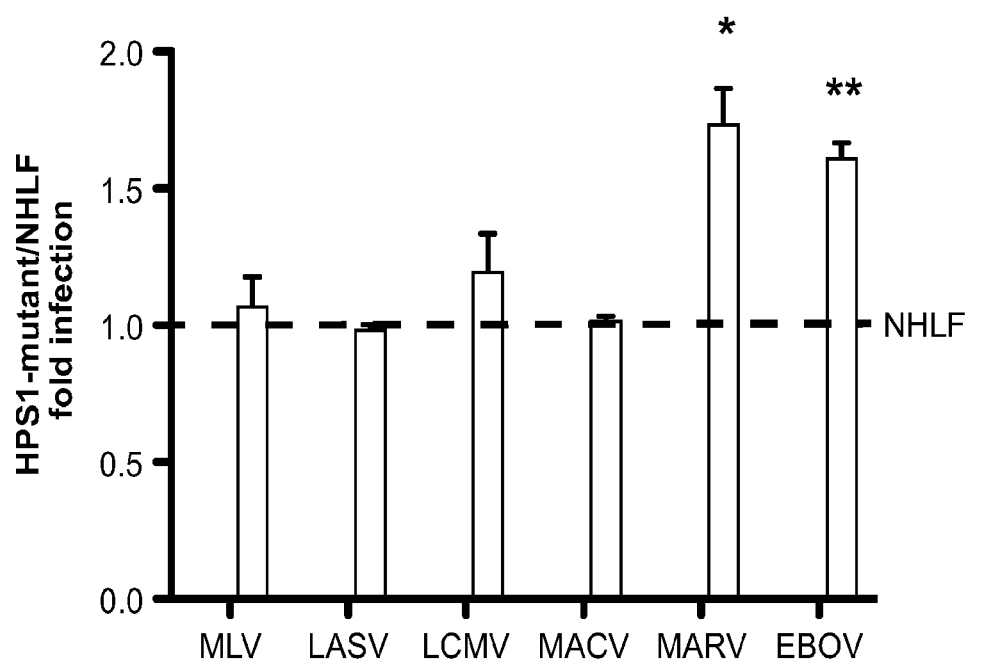
Figure 6D:
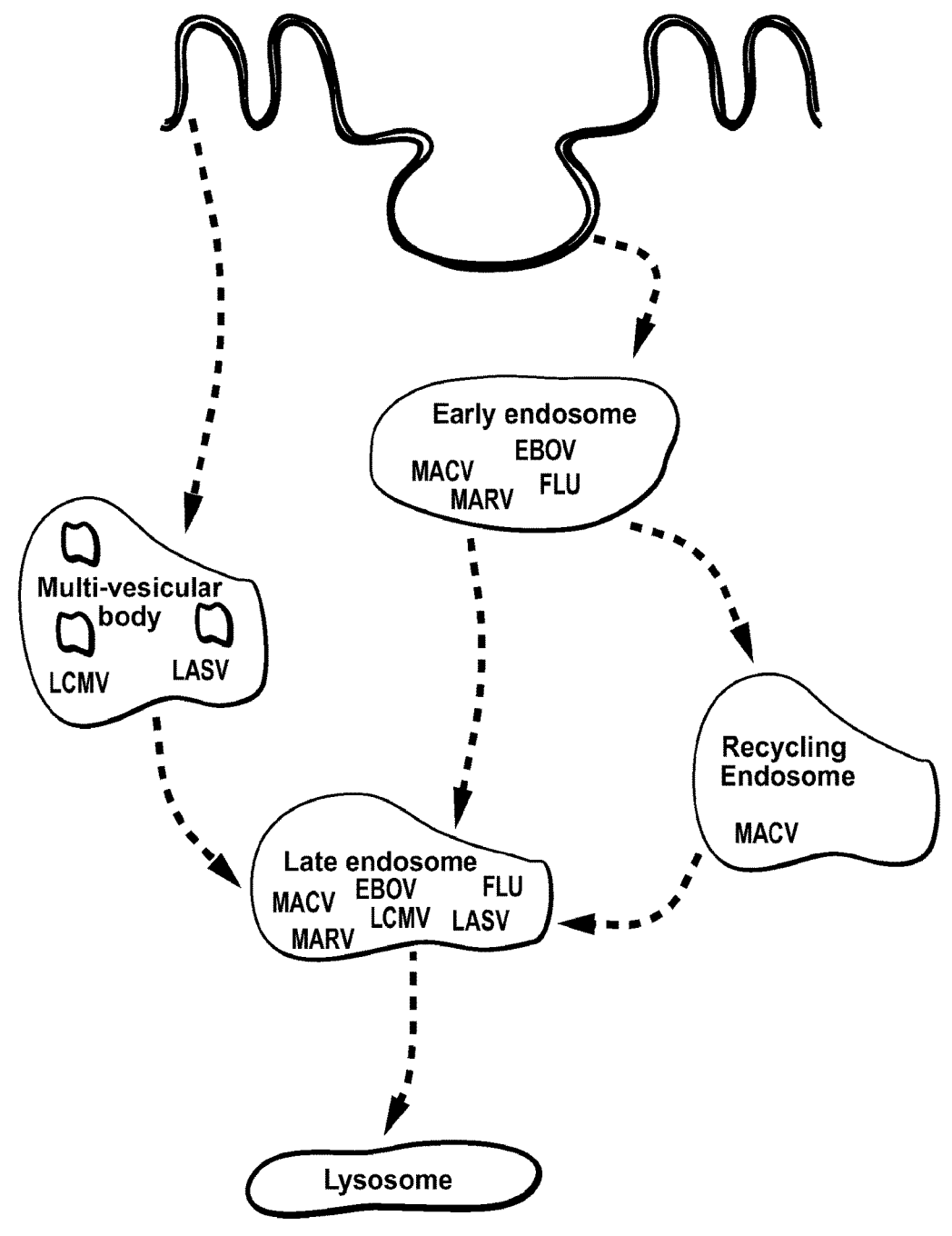

To confirm and further explore the role of HPS1 in viral entry, HPS1 function in regulating viral fusion was probed with endolysosomal compartments. DiD labeled influenza virus, which increases in fluorescence intensity upon fusion endosomal compartments, were tracked in HPS1$^{mut}$ and healthy control cells. Flow cytometry data showed increased fluorescence intensity in HPS1$^{mut}$ cells as early as 15 minutes post-infection, and a 4.4 fold increase in fusion in HPS1$^{mut}$ cells as compared to controls at 25 minutes post-infection (FIG. 6B). Live cell confocal confirmed the increased number of fusion events in HPS1$^{mut}$ cells, suggesting that the absence of HPS1 allows more viruses to enter vesicles that can support productive viral fusion.

To further dissect the role of HPS1 in virus-endolysosomal pathway interaction, the virus localization was assessed with various endosomal markers in HPS1$^{mut}$ and normal cells. Interestingly, there was no change in the amount of influenza co-localized with EEA1 or M6PR, early and late endosomal markers, respectively, by confocal microscopy. This suggests that HPS1 restriction occurs in intermediate endosomal compartments upstream of viral membrane fusion.

Example 6: Genome-Scale Pooled Lentivirus SHRNA Screening

To identify additional host restriction factors that prevent influenza replication in primary human bronchial epithelial cells (HBEs), shRNA library-transduced cells were pretreated with interferon β (IFNB1) to block influenza A virus (strain A/PR8/34) infection, and it was determined which of 54,000 lentiviral shRNAs restored viral infectivity to cells. A number of shRNAs were identified that could rescue influenza infection based on restored surface expression of influenza hemagglutinin (HA), an influenza protein localized to the plasma membrane (Table 1b). SC35/SRSF2, a known splicing factor, was selected for further studies because silencing of this factor fully restored influenza infection in an independent secondary screen (Table 1b). Examples of shRNAs used are listed in Table 3.

Example 7: Validation of SC35 Knockdown on Viral Replication

Figure 11A:
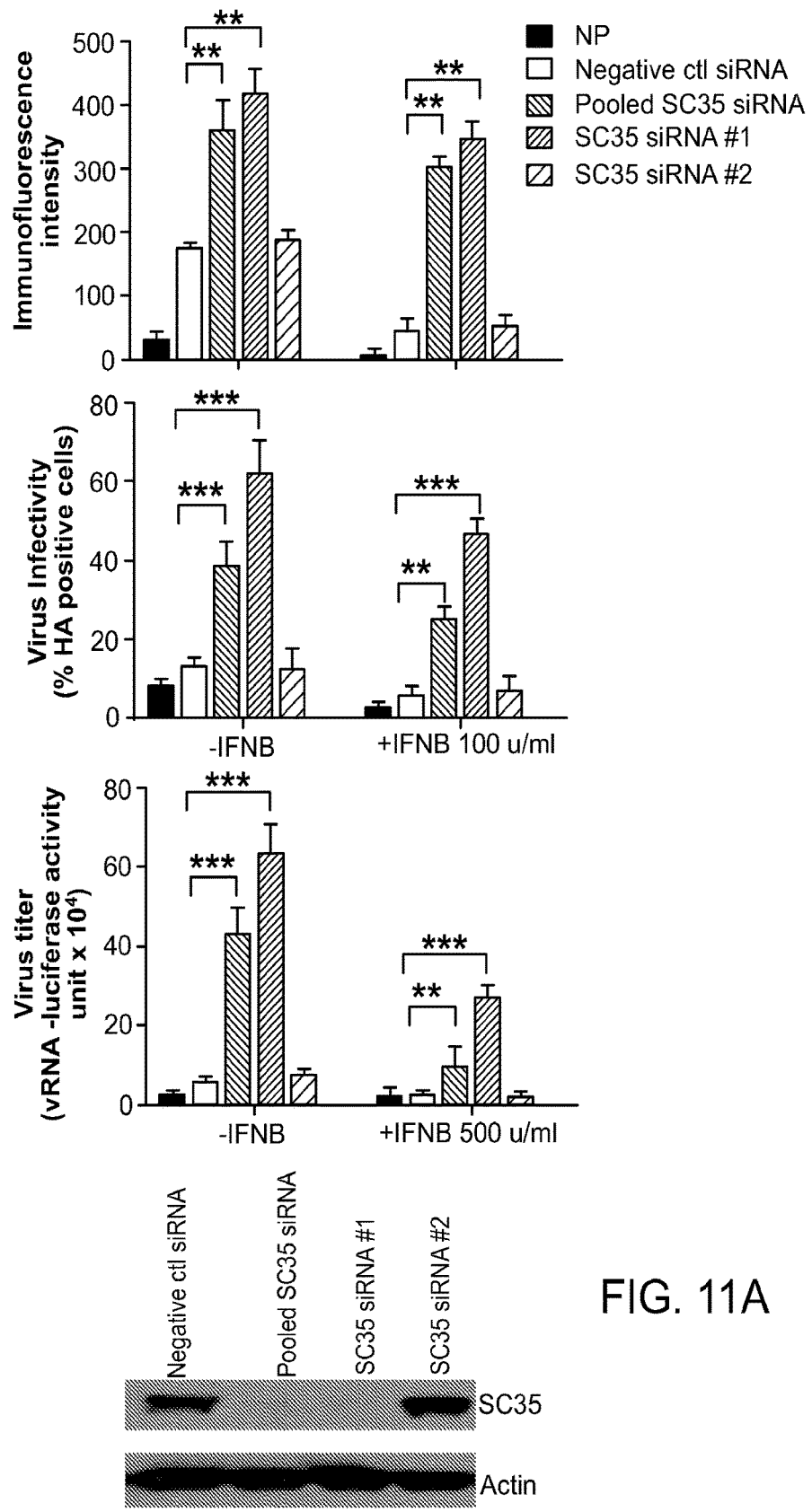
Figure 11B:
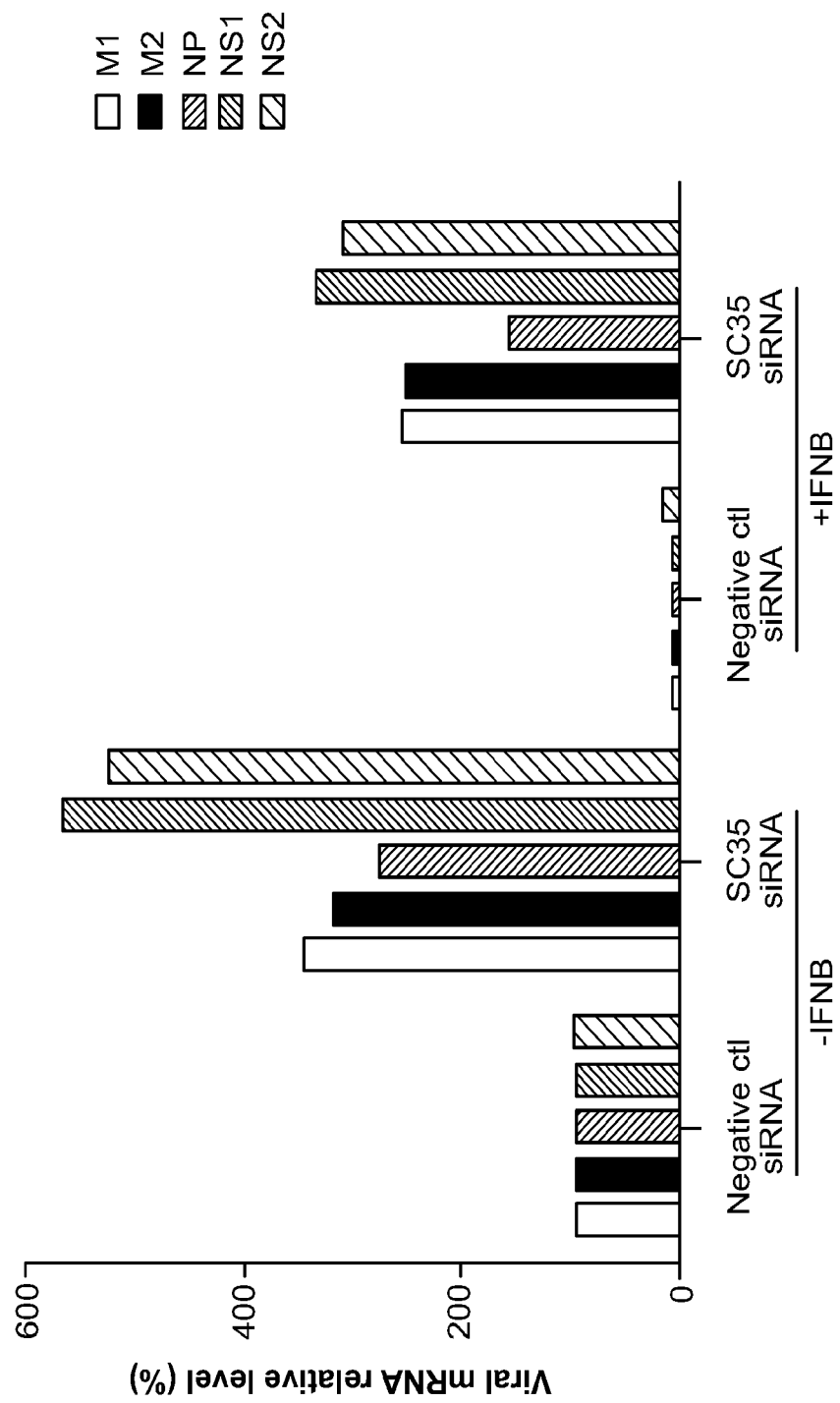
Figure 11D:
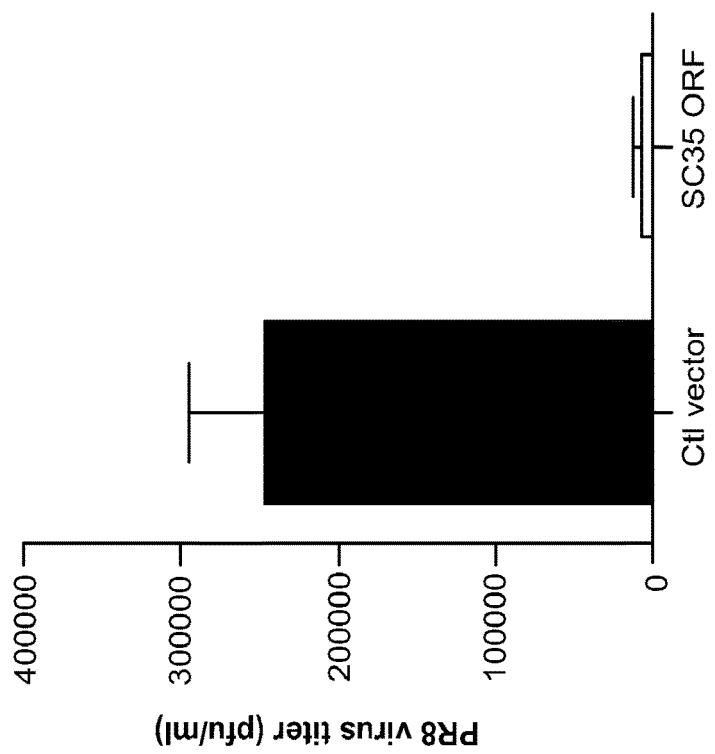
Figure 11C:
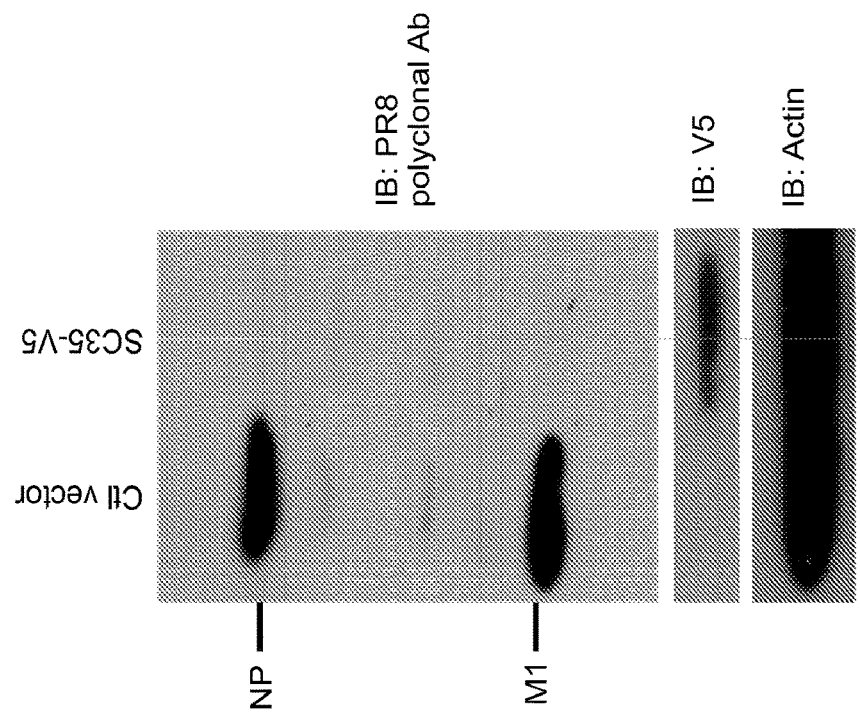
Figure 11E:
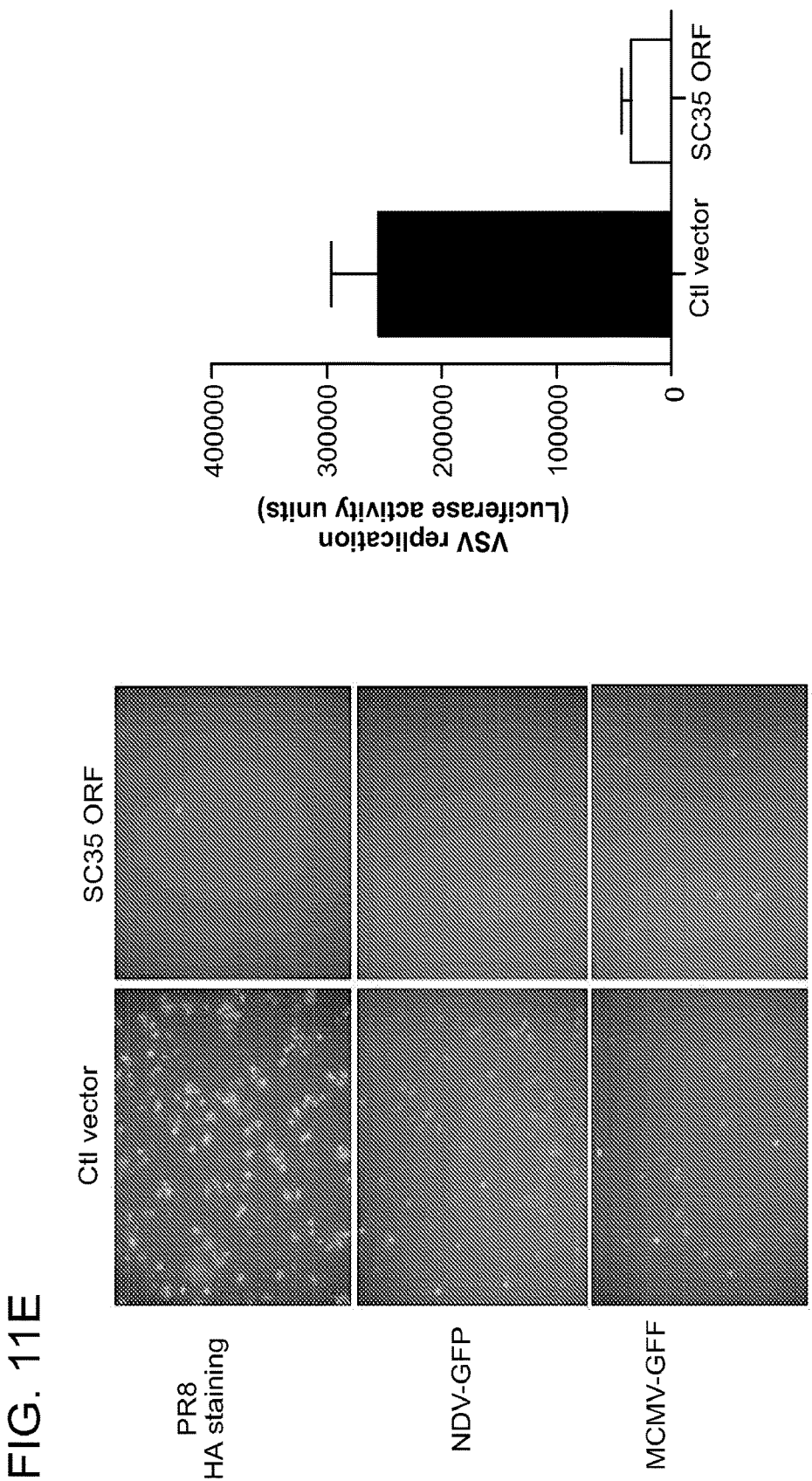

To confirm the finding from the shRNA screening, we measured the replication of PR8 in HBEs transfected with independent siRNA oligonucleotides to knockdown SC35. Influenza replication was first identified by quantifying the levels of the viral HA protein using automated microscopy, and observed a significant increase in HA levels in SC35-knockdown ('SC35-KD') cells relative to control cells ($p<0.01$), with or without IFNB1 ($p<0.01$) (FIG. 1A upper panel and middle panel). Then viral titers were quantified in the supernatants of cells using a vRNA-luciferase reporter cell (that expresses luciferase in proportion to infectious virus). Consistent with HA staining, there was increased virus in the supernatant of SC35-KD cells (FIG. 11A lower panel), even in the presence of highly suppressive IFNB1 treatment ($p<0.01$). As expected, transcripts of viral genes (M1, M2, NS1, NS2 and NP) were also more abundant in SC35-KD cells than in control cells (FIG. 11B). When SC35 was overexpressed, PR8 replication was inhibited, as detected by a polyclonal serum against viral proteins (FIG. 11C) or by traditional plaque assay (FIG. 11D). Given that splicing is required for influenza to produce the viral M1, M2, NS1 and NS2 transcripts from the M and NS segments, it was investigated whether SC35 may be responsible for viral RNA splicing. To exclude the effects of viral infection on the cell, the negative-sense vRNA for M together were expressed with the proteins (i.e., viral nucleoprotein NP and polymerases PA, PB1 and PB2, also known as '3P') required for synthesizing its complementary mRNA, which is normally spliced by host machinery to produce M1 and M2 transcripts. Using this system, overexpression of SC35 did not alter the mRNA levels or the protein levels of M1 and M2, suggesting that SC35 does not inhibit viral replication by altering the splicing of viral genes.

The influence of SC35 expression on other viruses was examined and it was found that SC35 overexpression inhibited replication of a broad range of RNA viruses, including Newcastle disease virus and vesicular stomatitis virus, and a DNA virus, mouse cytomegalovirus (FIG. 11E), therefore strongly suggesting that disruption of SC35 expression in a cell infected with a virus will increase viral replication.

Genes listed in Table 1b, marked with a 'V', were also validated in an independent secondary screen by silencing of those by siRNA oligonucleotides resulted in fully restored influenza invection. These genes include APPBP1, CEBPB, NFE2L2, NUP98, PDGFRL, PPP1R1c, SNAI2, TAF5L, TJP2, TMEM14C, ZNF331 and ZNF498.

TABLE 3 shRNA sequences for select genes that affect viral replication

| Clone ID | Clone Name | Target Taxon | Target Gene | Match Pos. | Match Region | KD: % Exp | Target Sequence | SEQ ID NO: | Forward Oligo Sequence | SEQ ID NO: | Reverse Oligo Sequence | SEQ ID NO: |
|---|---|---|---|---|---|---|---|---|---|---|---|---|
| TRCN0000 190736 | NM_ 019424. 1- 794s1c1 | mouse | Hps1 | 794 | CDS | 6% | GCAAGCT GTTGGCT TTCTACT | 1 | CCGGGCAAGCTG TTGGCTTTCTA CTCTCGAGAGTA GAAAGCCAACA GCTTGCTTTTTG | 37 | AATTCAAAAA GCAAGCTGTT GGCTTTCTAC TCTCGAGAGTA GAAAGCCAAC AGCTTGC | 73 |
| TRCN0000 292556 | NM_ 019424. 2- 845s21c1 | mouse | Hps1 | 845 | CDS | 6% | GCAAGCT GTTGGCT TTCTACT | 2 | CCGGGCAAGCTG TTGGCTTTCTA CTCTCGAGAGTA GAAAGCCAACA GCTTGCTTTTTG | 38 | AATTCAAAAA GCAAGCTGTT GGCTTTCTAC TCTCGAGAGTA GAAAGCCAACA GCTTGC | 74 |
| TRCN0000 192821 | NM_ 019424. 1- 1448s1c1 | mouse | Hps1 | 1448 | CDS | 7% | GCCAGAA GATGGAC AAGTTTA | 3 | CCGGGCCAGAAGA TGGACAAGTT TACTCGAGTAAA CTTGTCCATCTT CTGGCTTTTTG | 39 | AATTCAAAAA GCCAGAAGAT GGACAAGTTT ACTCGAGTAA ACTTGTCCAT CTTCTGGC | 75 |
| TRCN0000 298011 | NM_ 019424. 2- 1499s21c1 | mouse | Hps1 | 1499 | CDS | 7% | GCCAGAA GATGGAC AAGTTTA | 4 | CCGGGCCAGAAGA TGGACAAGTT TACTCGAGTAAA CTTGTCCATCTT CTGGCTTTTTG | 40 | AATTCAAAAA GCCAGAAGAT GGACAAGTTT ACTCGAGTAA ACTTGTCCAT CTTCTGGC | 76 |
| TRCN0000 380402 | NM_ 009680. 3- 439s21c1 | mouse | Ap3b1 | 439 | CDS | 10% | TACGTTT ACCTTGT CCGATAT | 5 | CCGGTACGTTTA CCTTGTCCGATA TCTCGAGATATC GGACAAGGTAA ACGTATTTTG | 41 | AATTCAAAAAT ACGTTTACCT TGTCCGATATC TCGAGATATC GGACAAGGTA AACGTA | 77 |
| TRCN0000 304937 | NM_ 009680. 3- 1637s21c1 | mouse | Ap3b1 | 1637 | CDS | 12% | CAAGCAT CCTTTGG CTAATTG | 6 | CCGGCAAGCATC CTTTGGCTAATT GCTCGAGCAATT AGCCAAAGGAT GCTTGTTTTTG | 42 | AATTCAAAAAC AAGCATCCTT TGGCTAATTG CTCGAGCAAT TAGCCAAAGG ATGCTTG | 78 |

TABLE 3-continued shRNA sequences for select genes that affect viral replication

| Clone ID | Clone Name | Target Taxon | Target Gene | Match Pos. | Match Region | KD: % Exp | Target Sequence | SEQ ID NO: | Forward Oligo Sequence | SEQ ID NO: | Reverse Oligo Sequence | SEQ ID NO: |
|---|---|---|---|---|---|---|---|---|---|---|---|---|
| TRCN0000 190490 | NM_ 019424. 1- 399s1c1 | mouse | Hps1 | 399 | CDS | 13% | GCATCTG TTTGGGA GTACCT | 7 | CCGGGCATCTGT TTGGAGAGTAC CTCTCGAGAGGT ACTCTCCAAAC AGATGCTTTTTG | 43 | AATTCAAAAAG CATCTGTTTG GAGAGTACCT CTCGAGAGGT ACTCTCCAAA CAGATGC | 79 |
| TRCN0000 292557 | NM_ 019424. 2- 1777s21c1 | mouse | Hps1 | 1777 | CDS | 13% | TTGGTGA AGAGCCG GAGAAAT | 8 | CCGGTTGGTGAA GAGCCGGAGA AATCTCGAGATT TCTCCGGCTCTT CACCAATTTTTG | 44 | AATTCAAAAA TTGGTGAAGA GCCGGAGAAA TCTCGAGATT TCTCCGGCTC TTCACCAA | 80 |
| TRCN0000 292555 | NM_ 019424. 2- 450s21c1 | mouse | Hps1 | 450 | CDS | 13% | GCATCTG TTTGGAG AGTACCT | 9 | CCGGGCATCTGT TTGGAGAGTAC CTCTCGAGAGGT ACTCTCCAAAC AGATGCTTTTTG | 45 | AATTCAAAAAG CATCTGTTTG GAGAGTACCT CTCGAGAGGT ACTCTCCAAA CAGATGC | 81 |
| TRCN0000 380055 | NM_ 009680. 3- 2883s21c1 | mouse | Ap3b1 | 2883 | CDS | 13% | ACAGATC ACCCTGA CTAATAC | 10 | CCGGACAGATCA CCCTGACTAAT ACCTCGAGGTAT TAGTCAGGGTG ATCTGTTTTTG | 46 | AATTCAAAAA ACAGATCACC CTGACTAATAC CTCGAGGTAT TAGTCAGGGT GATCTGT | 82 |
| TRCN0000 311174 | NM_ 009680. 3- 1097s21c1 | mouse | Ap3b1 | 1097 | CDS | 16% | TGGCTGT CGCTCAG CTATATT | 11 | CCGGTGGCTGTC GCTCAGCTATA TTCTCGAGAATA TAGCTGAGCGA CAGCCATTTTTG | 47 | AATTCAAAAA TGGCTGTCGC TCAGCTATATT CTCGAGAATA TAGCTGAGC GACAGCCA | 83 |
| TRCN0000 302757 | NM_ 009680. 3- 3782s21c1 | mouse | Ap3b1 | 3782 | 3UTR | 17% | GCTTGGC AATCGTC CTTCTTA | 12 | CCGGGCTTGGCA ATCGTCCTTCTT ACTCGAGTAAGA AGGACGATTGC CAAGCTTTTTG | 48 | AATTCAAAAA GCTTGGCAAT CGTCCTTCTTA CTCGAGTAAG AAGGACGATT GCAAGC | 84 |
| TRCN0000 100440 | NM_ 009680. 2- 3719s1c1 | mouse | Ap3b1 | 3719 | 3UTR | 17% | GCTTGGC AATCGTC CTTCTTA | 13 | CCGGGCTTGGCA ATCGTCCTTCTT ACTCGAGTAAGA AGGACGATTGC CAAGCTTTTTG | 49 | AATTCAAAAA GCTTGGCAAT CGTCCTTCTTA CTCGAGTAAG AAGGACGATT GCCAAGC | 85 |
| TRCN0000 000082 | NM_ 003016. x- 872s1c1 | human | SRSF2 (SC35) | 872 | 3UTR | 2% | ACCACAT AGTCCAT CGAAGAA | 14 | CCGGACCACATA GTCCATCGAAG AACTCGAGTTCT TCGATGGACTAT GTGGTTTTTG | 50 | AATTCAAAAA ACCACATAGT CCATCGAAGA ACTCGAGTTC TTCGATGGA CTATGTGGT | 86 |
| TRCN0000 000090 | NM_ 003016. x- 876s1c1 | human | SRSF2 (SC35) | 876 | 3UTR | 2% | CATAGTC CATCGAA GAAGAGT | 15 | CCGGCATAGTCC ATCGAAGAAGA GTCTCGAGACTC TTCTTCGATGGA CTATGTTTTTG | 51 | AATTCAAAAAC ATAGTCCATC GAAGAAGAGT CTCGAGACTC TTCTTCGATG GACTATG | 87 |
| TRCN0000 000096 | NM_ 003016. x- 831s1c1 | human | SRSF2 (SC35) | 831 | 3UTR | 6% | GTATCGG CAAGCAG TGTAAAC | 16 | CCGGGTATCGGC AAGCAGTGTAA ACCTCGAGGTTT ACACTGCTTGCC GATACTTTTTG | 52 | AATTCAAAAA GTATCGGCAA GCAGTGTAAA CCTCGAGGTT TACACTGCTT GCCGATAC | 88 |

TABLE 3-continued shRNA sequences for select genes that affect viral replication

| Clone ID | Clone Name | Target Taxon | Target Gene | Match Pos. | Match Region | KD: % Exp | Target Sequence | SEQ ID NO: | Forward Oligo Sequence | SEQ ID NO: | Reverse Oligo Sequence | SEQ ID NO: |
|---|---|---|---|---|---|---|---|---|---|---|---|---|
| TRCN0000000083 | NM_003016.x-1427s1c1 | human | SRSF2 (SC35) | 1427 | 3UTR | 7% | CAGTTGTGTAGCAGTTGAGTA | 17 | CCGGCAGTTGTGTAGCAGTTGAGTACTCGAGTACTCAACTGCTACACAACTGTTTTTG | 53 | AATTCAAAAACAGTTGTGTAGCAGTTGAGTACTCGAGTACTCAACTGCTACACAACTG | 89 |
| TRCN0000000081 | NM_003016.x-1428s1c1 | human | SRSF2 (SC35) | 1428 | 3UTR | 8% | AGTTGTGTAGCAGTTGAGTAA | 18 | CCGGAGTTGTGTAGCAGTTGAGTAACTCGAGTTACTCAACTGCTACACAACTTTTTTG | 54 | AATTCAAAAAAGTTGTGTAGCAGTTGAGTAACTCGAGTTACTCAACTGCTACACAACT | 90 |
| TRCN0000000084 | NM_003016.x-1508s1c1 | human | SRSF2 (SC35) | 1508 | 3UTR | 8% | TCTCCCGATTGCTCCTGTGTA | 19 | CCGGTCTCCCGATTGCTCCTGTGTACTCGAGTACACAGGAGCAATCGGGAGATTTTTG | 55 | AATTCAAAAATCTCCCGATTGCTCCTGTGTACTCGAGTACACAGGAGCAATCGGGAGA | 91 |
| TRCN0000000098 | NM_003016.x-1485s1c1 | human | SRSF2 (SC35) | 1485 | 3UTR | 8% | GAGTGCTTGGCTGTTTCCTGT | 20 | CCGGGAGTGCTTGGCTGTTTCCTGTCTCGAGACAGGAAACAGCCAAGCACTCTTTTTG | 56 | AATTCAAAAAGAGTGCTTGGCTGTTTCCTGTCTCGAGACAGGAAACAGCCAAGCACTC | 92 |
| TRCN0000065062 | NM_003664.3-1614s1c1 | human | AP3B1 (SC35) | 1614 | CDS | 8% | GCAAGTATTCTTTGGCTAATT | 21 | CCGGGCAAGTATTCTTTGGCTAATTCTCGAGAATTAGCCAAAGAATACTTGCTTTTTG | 57 | AATTCAAAAAGCAAGTATTCTTTGGCTAATTCTCGAGAATTAGCCAAAGAATACTTGC | 93 |
| TRCN0000286136 | NM_003664.3-1614s21c1 | human | AP3B1 (SC35) | 1614 | CDS | 8% | GCAAGTATTCTTTGGCTAATT | 22 | CCGGGCAAGTATTCTTTGGCTAATTCTCGAGAATTAGCCAAAGAATACTTGCTTTTTG | 58 | AATTCAAAAAGCAAGTATTCTTTGGCTAATTCTCGAGAATTAGCCAAAGAATACTTGC | 94 |
| TRCN0000000089 | NM_003016.x-874s1c1 | human | SRSF2 (SC35) | 874 | 3UTR | 10% | CACATAGTCCATCGAAGAAGA | 23 | CCGGCACATAGTCCATCGAAGAAGACTCGAGTCTTCTTCGATGGACTATGTGTTTTTG | 59 | AATTCAAAAACACATAGTCCATCGAAGAAGACTCGAGTCTTCTTCGATGGACTATGTG | 95 |
| TRCN0000000085 | NM_003016.x-1539s1c1 | human | SRSF2 (SC35) | 1539 | 3UTR | 13% | GTCGTGCAGAAACAAATGGCT | 24 | CCGGGTCGTGCAGAAACAAATGGCTCTCGAGAGCCATTTGTTTCTGCACGACTTTTTG | 60 | AATTCAAAAAGTCGTGCAGAAACAAATGGCTCTCGAGAGCCATTTGTTTCTGCACGAC | 96 |
| TRCN0000293216 | NM_003664.3-2765s21c1 | human | AP3B1 | 2765 | CDS | 13% | AGGACTAGCTGCCCATTATTT | 25 | CCGGAGGACTAGCTGCCCATTATTTCTCGAGAAATAATGGGCAGCTAGTCCTTTTTTG | 61 | AATTCAAAAAAGGACTAGCTGCCCATTATTTCTCGAGAAATAATGGGCAGCTAGTCCT | 97 |
| TRCN0000000099 | NM_003016.x-873s1c1 | human | SRSF2 (SC35) | 873 | 3UTR | 14% | CCACATAGTCCATCGAAGAAG | 26 | CCGGCCACATAGTCCATCGAAGAAGCTCGAGCTTCTTCGATGGACTATGTGGTTTTTG | 62 | AATTCAAAAACCACATAGTCCATCGAAGAAGCTCGAGCTTCTTCGATGGACTATGTGG | 98 |

TABLE 3-continued shRNA sequences for select genes that affect viral replication

| Clone ID | Clone Name | Target Taxon | Target Gene | Match Pos. | Match Region | KD: % Exp | Target Sequence | SEQ ID NO: | Forward Oligo Sequence | SEQ ID NO: | Reverse Oligo Sequence | SEQ ID NO: |
|---|---|---|---|---|---|---|---|---|---|---|---|---|
| TRCN0000000107 | NM_003016.x-1516s1c1 | human | SRSF2 (SC35) | 1516 | 3UTR | 14% | TTGCTCCTGTGTAAAGATGCC | 27 | CCGGTTGCTCCTGTGTAAAGATGCCCCTCGAGGGCATCTTTACACAGGAGCAATTTTTG | 63 | AATTCAAAAATTGCTCCTGTGTAAAGATGCCCTCGAGGGCATCTTTACACAGGAGCAA | 99 |
| TRCN0000065059 | NM_003664.3-2712s1c1 | human | AP3B1 | 2712 | CDS | 15% | CCTGCATTTGTACCAACGAAA | 28 | CCGGCCTGCATTTGTACCAACGAAACTCGAGTTTCGTTGGTACAAATGCAGGTTTTTG | 64 | AATTCAAAAACCTGCATTTGTACCAACGAAACTCGAGTTTCGTTGGTACAAATGCAGG | 100 |
| TRCN0000065060 | NM_003664.3-1389s1c1 | human | AP3B1 | 1389 | CDS | 15% | GCAGCCACCTATTCAGACTATA | 29 | CCGGGCAGCCACCTATTCAGACTATACTCGAGTATAGTCTGAATAGTGGCTGCTTTTTG | 65 | AATTCAAAAAGCAGCCACCTATTCAGACTATACTCGAGTATAGTCTGAATAGTGGCTGC | 101 |
| TRCN0000286138 | NM_003664.3-1389s21c1 | human | AP3B1 | 1389 | CDS | 15% | GCAGCCACCTATTCAGACTATA | 30 | CCGGGCAGCCACCTATTCAGACTATAGTCTGAATAGTGGCTGCTTTTTG | 66 | AATTCAAAAAGCAGCCACCTATTCAGACTATACTCGAGTATAGTCTGAATAGTGGCTGC | 102 |
| TRCN0000286137 | NM_003664.3-2712s21c1 | human | AP3B1 | 2712 | CDS | 15% | CCTGCATTTGTACCAACGAAA | 31 | CCGGCCTGCATTTGTACCAACGAAACTCGAGTTTCGTTGGTACAAATGCAGGTTTTTG | 67 | AATTCAAAAACCTGCATTTGTACCAACGAAACTCGAGTTTCGTTGGTACAAATGCAGG | 103 |
| TRCN0000000086 | NM_003016.x-829s1c1 | human | SRSF2 (SC35) | 829 | 3UTR | 16% | ATGTATCGGCAAGCAGTGTAA | 32 | CCGGATGTATCGGCAAGCAGTGTAACTCGAGTTACACTGCTTGCCGATACATTTTTTG | 68 | AATTCAAAAAATGTATCGGCAAGCAGTGTAACTCGAGTTACACTGCTTGCCGATACAT | 104 |
| TRCN0000000094 | NM_003016.x-875s1c1 | human | SRSF2 (SC35) | 875 | 3UTR | 16% | ACATAGTCCATCGAAGAAGAG | 33 | CCGGACATAGTCCATCGAAGAAGAGCTCGAGCTCTTCTTCGATGGACTATGTTTTTTG | 69 | AATTCAAAAAACATAGTCCATCGAAGAAGAGCTCGAGCTCTTCTTCGATGGACTATGT | 105 |
| TRCN0000000109 | NM_003016.x-832s1c1 | human | SRSF2 (SC35) | 832 | 3UTR | 16% | TATCGGCAAGCAGTGTAAACG | 34 | CCGGTATCGGCAAGCAGTGTAAACGCTCGAGCGTTTACACTGCTTGCCGATATTTTTG | 70 | AATTCAAAAATATCGGCAAGCAGTGTAAACGCTCGAGCGTTTACACTGCTTGCCGATA | 106 |
| TRCN0000293164 | NM_003664.3-3604s21c1 | human | AP3B1 | 3604 | 3UTR | 17% | TGCTAACCAAAGAGCATATAT | 35 | CCGGTGCTAACCAAAGAGCATATATCTCGAGATATATGCTCTTTGGTTAGCATTTTTG | 71 | AATTCAAAAATGCTAACCAAAGAGCATATATCTCGAGATATATGCTCTTTGGTTAGCA | 107 |
| TRCN0000000106 | NM_003016.x-836s1c1 | human | SRSF2 (SC35) | 836 | 3UTR | 18% | GGCAAGACGTGTAACGGAGG | 36 | CCGGGGCAAGCAGTGTAAACGGAGGCTCGAGCCTCCGTTTACACTGCTTGCCTTTTTG | 72 | AATTCAAAAAGGCAAGCAGTGTAAACGGAGGCTCGAGCCTCCGTTTACACTGCTTGCC | 108 |

We claim:

1. A virus-infected cell selected from the group consisting of Vero cells, baby hamster kidney (BHK) cells, primary chick kidney (PCK) cells, Madin-Darby Canine Kidney (MDCK) cells, Madin-Darby Bovine Kidney cells, 293 cells, COS cells and Human Embryonic Kidney (HEK) 293T cells, which cell produces an increased amount of virus relative to a wild-type cell infected with the same virus and which cell comprises one or more genes selected from the group consisting of HPS5, HPS1, AP3B1, AP3D, SC35, APPBP1, CEBPB, NFE2L2, PDGFRL, PPPIRIC, SFRS2, SNAI2, TAF5L, TJP2, TMEM14C, ZNFF331 and ZNF498 whose expression or activity is reduced or inhibited in said virus-infected cell.

2. The cell of claim 1, wherein the virus is an influenza virus, an Ebola virus, or a Marburg virus.

3. The cell of claim 1, wherein the cell is mammalian cell.

4. The cell of claim 3, wherein the mammalian cell is from a hamster, cattle, monkey, dog or human.

5. A method for replicating a virus comprising: a) providing a cell culture comprising cells selected from the group consisting of Vero cells, baby hamster kidney (BHK) cells, primary chick kidney (PCK) cells, Madin-Darby Canine Kidney (MDCK) cells, Madin-Darby Bovine Kidney cells, 293 cells, COS cells, and Human Embryonic Kidney (HEK) 293T cell, said cells comprising one or more genes selected from the group consisting of HPS5, HPS1, AP3B1, AP3D, SC35, APPBP1, CEBPB, NFE2L2, PDGFRL, PPPIRIC, SFRS2, SNAI2, TAF5L, TJP2, TMEM14C, ZNFF331 and ZNF498, whose expression or activity is reduced or inhibited in said cells;

b) infecting the cells with a virus selected from influenza virus, Ebola virus, Marburg virus, Moloney leukemia virus, Machupo virus, Lassa virus, Lymphocytic choriomeningitis virus, Newcastle disease virus, Vesicular stomatitis virus, or cytomegalovirus virus; and c) culturing the cells infected in step (b) to replicate the virus; wherein the virus exhibits increased viral replication relative to a wild-type cell.

6. The method of claim 5, further comprising isolating the virus replicated in step (c).

7. A process of replicating a virus comprising:

a) injecting a fertilized egg with a virus selected from influenza virus, Ebola virus, Marburg virus, Moloney leukemia virus, Machupo virus, Lassa virus, Lymphocytic choriomeningitis virus, Newcastle disease virus, Vesicular stomatitis virus, or cytomegalovirus virus and a compound that inhibits the expression or activity of one or more genes selected from the group consisting of HPS5, HPS1, AP3B1, AP3D, SC35, APPBP1, CEBPB, NFE2L2, PDGFRL, PPPIRIC, SFRS2, SNAI2, TAF5L, TJP2, TMEM14C, ZNFF331 and ZNF498; and b) incubating the egg for a predetermined period of time to replicate the virus.

8. A process of replicating a virus comprising:

a) injecting a cell with a virus selected from influenza virus, Ebola virus, Marburg virus, Moloney leukemia virus, Machupo virus, Lassa virus, Lymphocytic choriomeningitis virus, Newcastle disease virus, Vesicular stomatitis virus, or cytomegalovirus virus and a compound that inhibits the expression or activity of one or more genes selected from the group consisting of HPS5, HPS1, AP3B1, AP3D, SC35, APPBP1, CEBPB, NFE2L2, PDGFRL, PPPIRIC, SFRS2, SNAI2, TAF5L, TJP2, TMEM14C, ZNFF331 and ZNF498; and b) incubating the cell for a predetermined period of time to replicate the virus.

9. The process of claim 7, further comprising isolating the replicated virus in step (b).

10. The process of claim 7, wherein said compound is a nucleic acid.

11. The process of claim 7, wherein said compound is a siRNA.

12. The process of claim 8, wherein the cell comprises a disruption of one or more genes selected from the group consisting of HPS5, HPS1, AP3B1, AP3D, SC35, APPBP1, CEBPB, NFE2L2, PDGFRL, PPPIRIC, SFRS2, SNAI2, TAF5L, TJP2, TMEM14C, ZNFF331 and ZNF498, wherein the disruption results in decreased expression or activity of the one or more genes in the cell.

13. The process of claim 8, wherein the cell is a vertebrate cell.

14. The process of claim 8, wherein the cell is a mammalian cell.

15. The process of claim 14, wherein the mammalian cell is from a hamster, cattle, monkey, dog or human.

* * * * *